(12) United States Patent
Morejohn et al.

(10) Patent No.: US 11,229,479 B2
(45) Date of Patent: Jan. 25, 2022

(54) ADJUSTABLE CLAMP SYSTEMS AND METHODS

(71) Applicant: AtriCure, Inc., Mason, OH (US)

(72) Inventors: Dwight P. Morejohn, Davis, CA (US); Tamer Ibrahim, Danville, CA (US); Michael J. Banchieri, Discovery Bay, CA (US); Ara Stephanian, Davis, CA (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 16/514,783

(22) Filed: Jul. 17, 2019

(65) Prior Publication Data

US 2020/0000511 A1    Jan. 2, 2020

Related U.S. Application Data

(63) Continuation of application No. 15/271,078, filed on Sep. 20, 2016, now Pat. No. 10,398,495, which is a
(Continued)

(51) Int. Cl.
*A61B 18/18* (2006.01)
*A61B 18/14* (2006.01)
(Continued)

(52) U.S. Cl.
CPC ...... *A61B 18/1442* (2013.01); *A61B 18/0206* (2013.01); *A61B 18/06* (2013.01); *A61B 18/085* (2013.01); *A61B 18/1206* (2013.01); *A61B 18/1815* (2013.01); *A61B 18/20* (2013.01); *A61B 2018/00023* (2013.01);
(Continued)

(58) Field of Classification Search
CPC ... A61B 18/0206; A61B 18/06; A61B 18/085; A61B 18/1206; A61B 18/1442; A61B 18/1815; A61B 18/20; A61B 2018/00023; A61B 2018/00273; A61B 2018/00351; A61B 2018/00577; A61B 2018/00702;
(Continued)

(56) References Cited

U.S. PATENT DOCUMENTS 5,536,251 A * 7/1996 Evard .............. A61B 17/00234
                                                    128/DIG. 26
5,626,607 A * 5/1997 Malecki .......... A61B 17/00234
                                                           606/205
(Continued)

OTHER PUBLICATIONS

U.S. Appl. No. 15/271,078, filed Sep. 20, 2016.
U.S. Appl. No. 14/740,514, filed Jun. 16, 2015.
U.S. Appl. No. 12/971,774, filed Dec. 17, 2010.

*Primary Examiner* — Michael F Peffley
*Assistant Examiner* — Amanda L Zink
(74) *Attorney, Agent, or Firm* — Levine Bagade Han LLP

(57) ABSTRACT

Tissue treatment systems include an actuator handle assembly coupled with a clamp assembly having a first jaw mechanism and a second jaw mechanism. A first jaw mechanism includes a first flexible boot, a first flexible ablation member coupled with the first flexible boot, and a first rotatable jawbone disposed within the first flexible boot. A second jaw mechanism comprises a second flexible boot, a
(Continued)

second flexible ablation member coupled with the second flexible boot, and a second rotatable jawbone disposed within the second flexible boot.

11 Claims, 51 Drawing Sheets

Related U.S. Application Data continuation of application No. 14/740,514, filed on Jun. 16, 2015, now Pat. No. 9,445,864, which is a continuation of application No. 12/971,774, filed on Dec. 17, 2010, now Pat. No. 9,072,522.

(60) Provisional application No. 61/288,031, filed on Dec. 18, 2009.

(51) Int. Cl.
*A61B 18/20* (2006.01)
*A61B 18/02* (2006.01)
*A61B 18/06* (2006.01)
*A61B 18/08* (2006.01)
*A61B 18/12* (2006.01)
*A61B 18/00* (2006.01)
*A61N 7/02* (2006.01)

(52) U.S. Cl.
CPC .............. *A61B 2018/00273* (2013.01); *A61B 2018/00351* (2013.01); *A61B 2018/00577* (2013.01); *A61B 2018/00702* (2013.01); *A61B 2018/00791* (2013.01); *A61B 2018/0225* (2013.01); *A61B 2018/145* (2013.01); *A61N 7/02* (2013.01)

(58) Field of Classification Search
CPC .. A61B 2018/00791; A61B 2018/0225; A61B 2018/145; A61N 7/02
See application file for complete search history.

(56) References Cited

U.S. PATENT DOCUMENTS

| | | | |
|---|---|---|---|
| 5,906,615 A * | 5/1999 | Thompson | A61B 18/1485 606/45 |
| 6,142,994 A | 11/2000 | Swanson et al. | |
| 6,849,075 B2 | 2/2005 | Bertolero et al. | |
| 7,226,448 B2 | 6/2007 | Bertolero et al. | |
| 7,674,258 B2 | 3/2010 | Swanson | |
| 7,749,157 B2 | 7/2010 | Bertolero | |
| 7,753,908 B2 | 7/2010 | Swanson | |
| 7,785,324 B2 | 8/2010 | Eberl | |
| 7,819,867 B2 | 10/2010 | Bertolero et al. | |
| 8,002,771 B2 * | 8/2011 | Cox | A61B 90/50 606/51 |
| 10,398,495 B2 | 9/2019 | Morejohn et al. | |
| 2003/0158549 A1 | 8/2003 | Swanson | |
| 2004/0059325 A1 | 3/2004 | Swanson | |
| 2004/0068274 A1* | 4/2004 | Hooven | A61B 18/1442 606/151 |
| 2005/0113828 A1* | 5/2005 | Shields | A61B 18/1445 606/51 |
| 2005/0240175 A1 | 10/2005 | Bertolero et al. | |
| 2006/0084974 A1* | 4/2006 | Privitera | A61B 18/1447 606/50 |
| 2006/0095031 A1 | 5/2006 | Ormsby | |
| 2007/0191714 A1* | 8/2007 | Cox | A61B 18/1482 600/471 |
| 2008/0294154 A1 | 11/2008 | Ibrahim et al. | |
| 2009/0048591 A1 | 2/2009 | Ibrahim et al. | |
| 2009/0076501 A1 | 3/2009 | Bertolero et al. | |
| 2009/0076537 A1 | 3/2009 | Bertolero | |
| 2009/0163768 A1 | 6/2009 | Ibrahim et al. | |
| 2009/0281541 A1 | 11/2009 | Ibrahim et al. | |
| 2010/0023004 A1* | 1/2010 | Francischelli | A61B 18/1442 606/41 |
| 2017/0354457 A1 | 12/2017 | Morejohn et al. | |

* cited by examiner

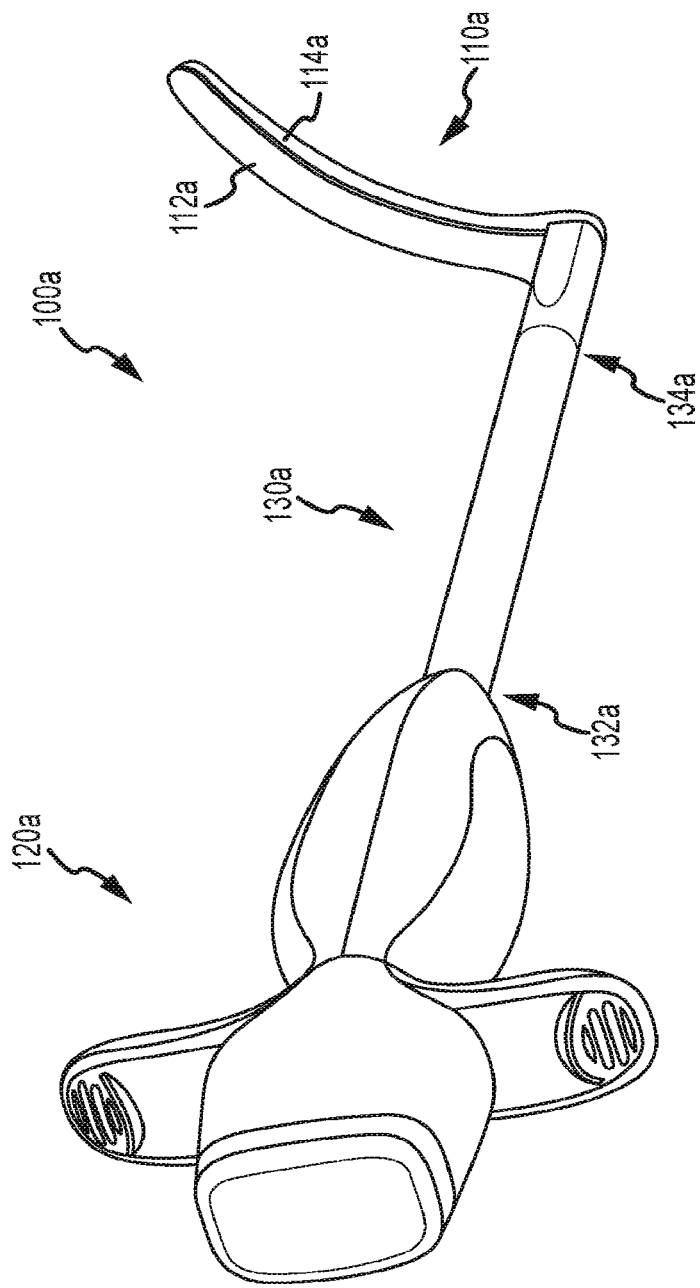

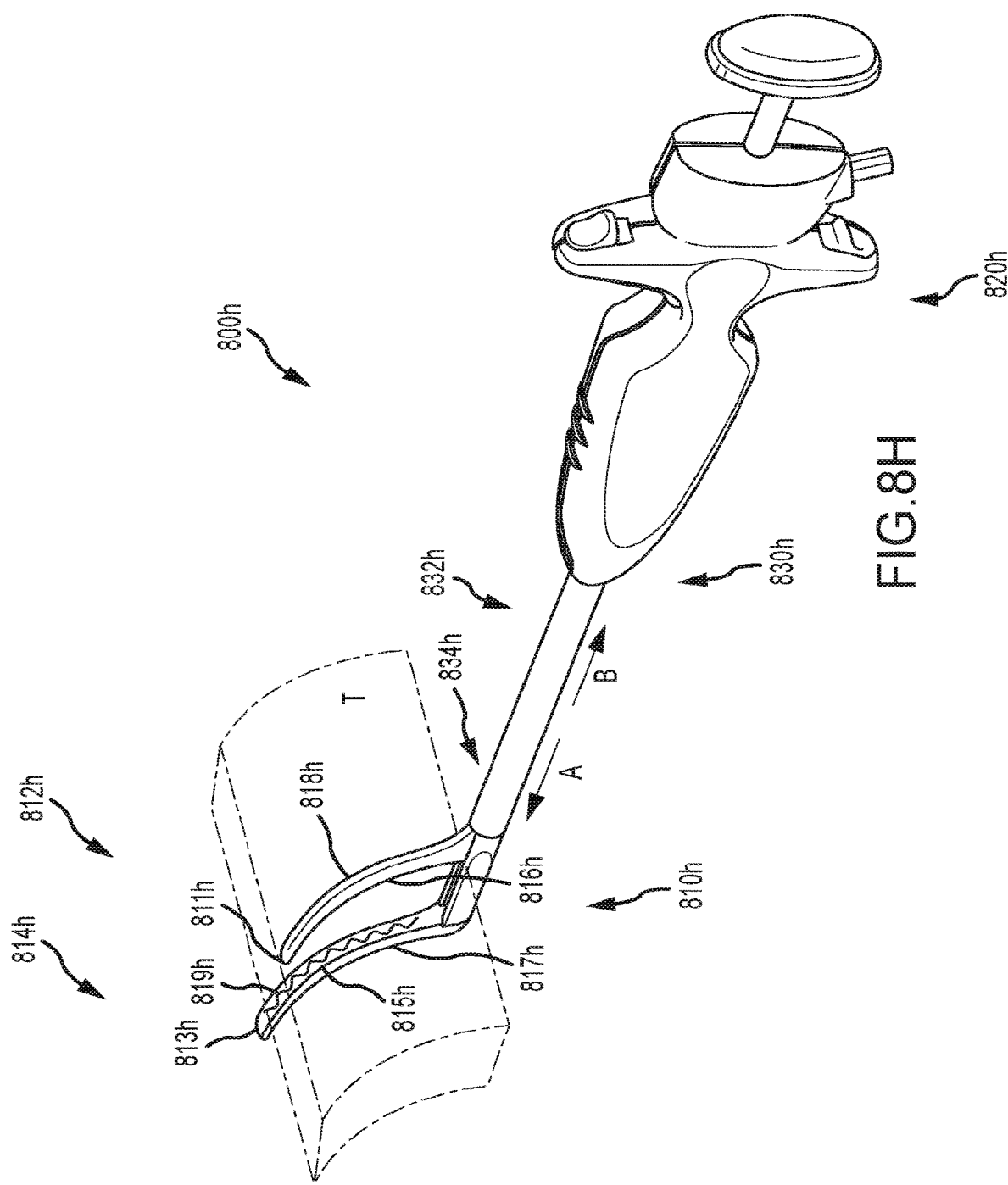

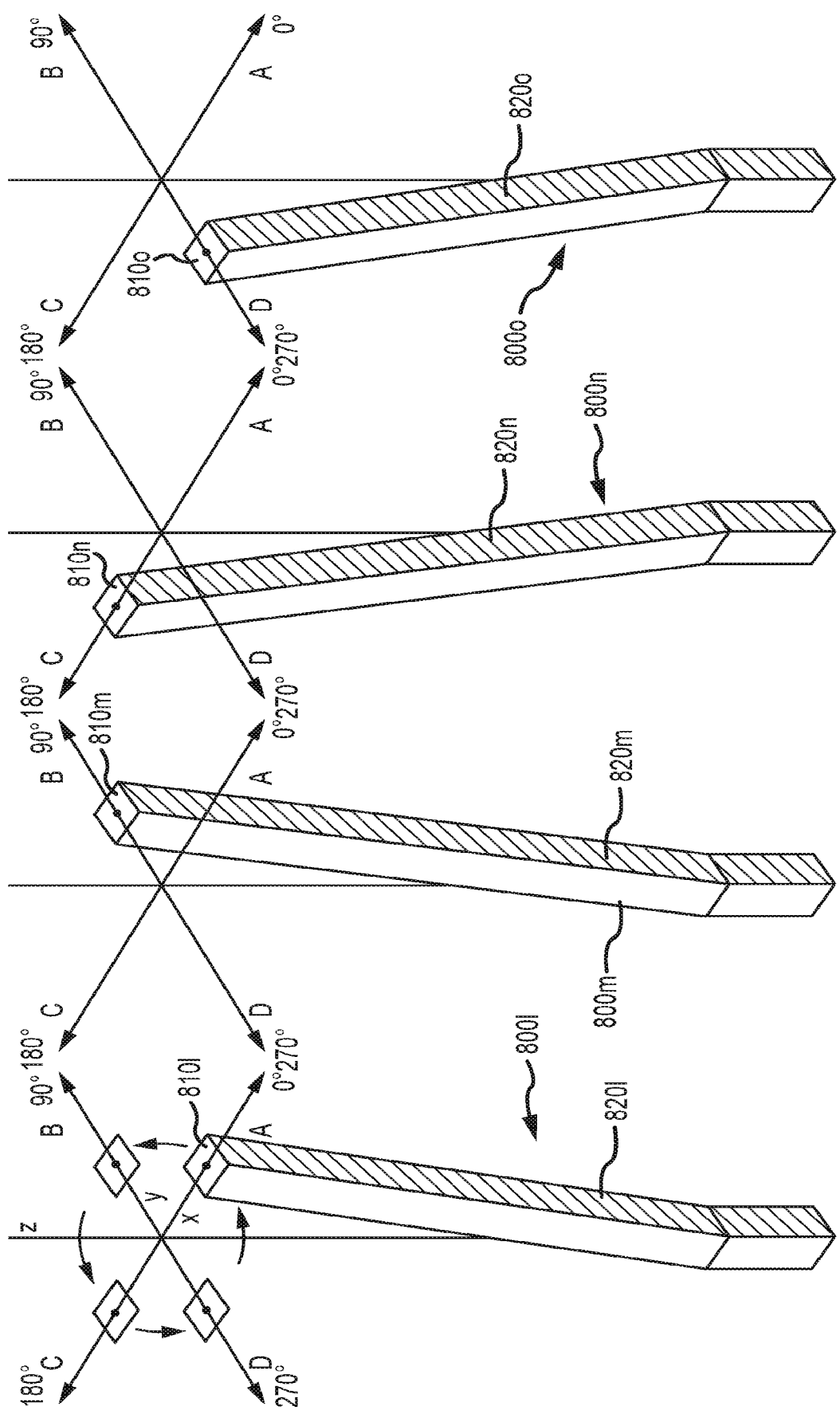

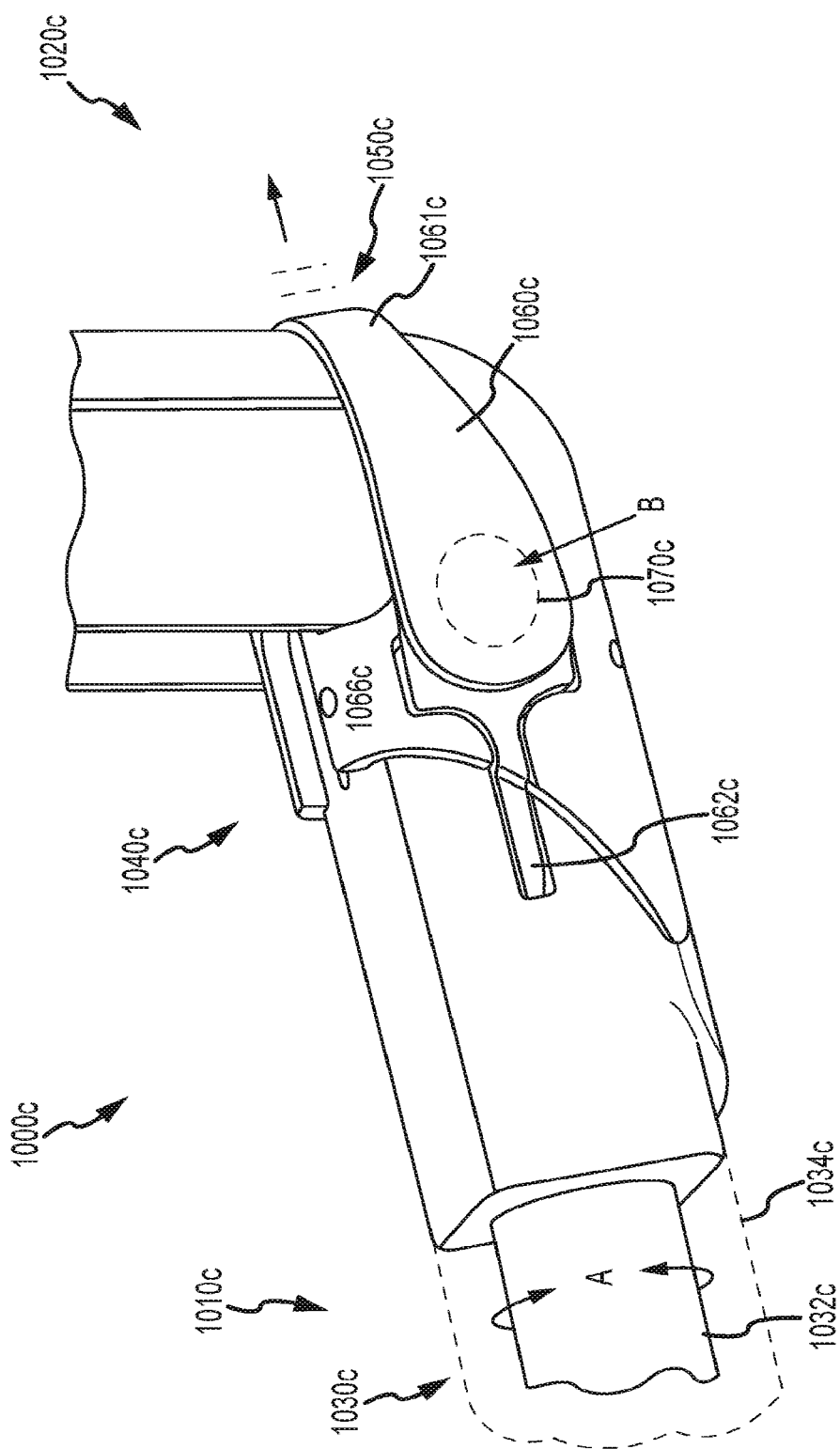

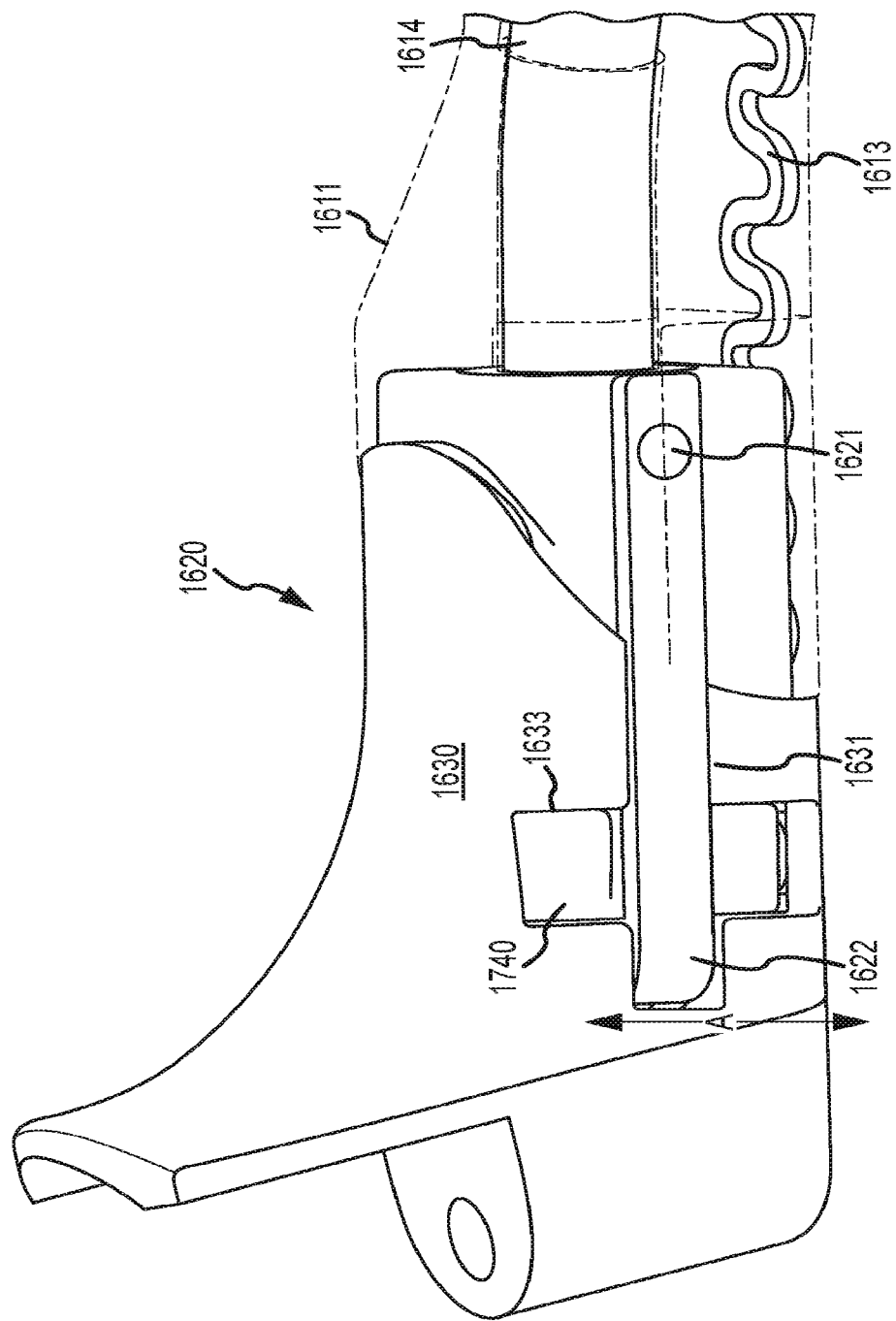

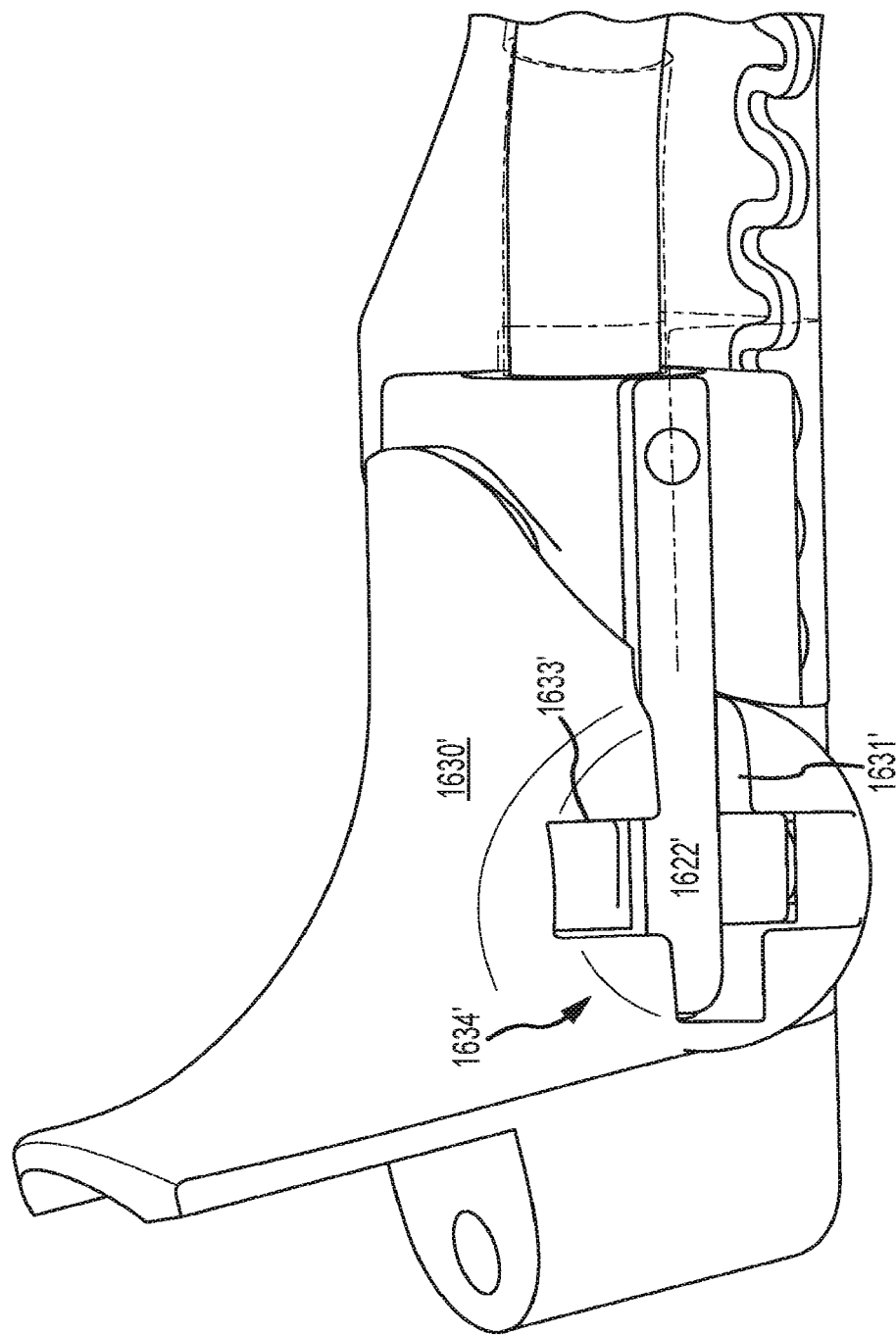

ADJUSTABLE CLAMP SYSTEMS AND METHODS

CROSS-REFERENCES TO RELATED APPLICATIONS

This application is a continuation of U.S. Nonprovisional patent application Ser. No. 15/271,078 filed Sep. 20, 2016, (now U.S. Pat. No. 10,398,495 issued Sep. 3, 2019), which is a continuation of U.S. Nonprovisional patent application Ser. No. 14/740,514, filed Jun. 16, 2015, (now U.S. Pat. No. 9,445,864 issued on Sep. 20, 2016), which is a continuation of U.S. Nonprovisional patent application Ser. No. 12/971,774, filed Dec. 17, 2010, (now U.S. Pat. No. 9,072,522 issued on Jul. 7, 2015), which is a nonprovisional of, and claims the benefit of the filing date of U.S. Provisional Patent Application No. 61/288,031, filed Dec. 18, 2009. This application is also related to U.S. Patent Application No. 60/337,070 filed Dec. 4, 2001; Ser. No. 10/080,374 filed Feb. 19, 2002 (now U.S. Pat. No. 7,753,908 issued Jul. 13, 2010); Ser. No. 10/255,025 filed Sep. 24, 2002; Ser. No. 10/272,446 filed Oct. 15, 2002 (now U.S. Pat. No. 6,849,075 issued Feb. 1, 2005); Ser. No. 10/410,618 filed Apr. 8, 2003 (now U.S. Pat. No. 7,226,448 issued Jun. 5, 2007); Ser. No. 11/067,535 filed Feb. 25, 2005 (now U.S. Pat. No. 7,785,324 issued Aug. 31, 2010); Ser. No. 11/148,611 filed Jun. 8, 2005 (now U.S. Pat. No. 7,819,867 issued Oct. 26, 2010); 61/051,975, filed May 9, 2008; Ser. No. 12/255,076 filed Oct. 21, 2008 (now U.S. Pat. No. 8,535,307 issued Sep. 17, 2013); and Ser. No. 12/463,760 filed May 11, 2009. The entire content of each of these filings is incorporated herein by reference for all purposes.

BACKGROUND OF THE INVENTION

Embodiments of the present invention relate generally to therapeutic systems and methods, and more particularly, to techniques that are well suited for the formation of lesions in body tissue.

There are many instances where it is beneficial to perform a therapeutic intervention in a patient, using a system that is inserted within the patient's body. One exemplary therapeutic intervention involves the formation of therapeutic lesions in the patient's heart tissue to treat cardiac conditions such as atrial fibrillation, atrial flutter, and arrhythmia. Therapeutic lesions may also be used to treat conditions in other regions of the body including, but not limited to, the prostate, liver, brain, gall bladder, uterus, and other solid organs. Typically, the lesions are formed by ablating tissue with one or more electrodes. Electromagnetic radio frequency ("RF") energy applied by the electrode heats and eventually kills or ablates the tissue to form a lesion. During the ablation of soft tissue (e.g. tissue other than blood, bone and connective tissue), tissue coagulation occurs, which leads to tissue death. Thus, references to the ablation of soft tissue are typically references to soft tissue coagulation. "Tissue coagulation" can refer to the process of cross-linking proteins in tissue to cause the tissue to jell. In soft tissue, it is the fluid within the tissue cell membranes that jells to kill the cells, thereby killing the tissue. Depending on the procedure, a variety of different electrophysiology devices may be used to position one or more electrodes at the target location. Electrodes can be connected to power supply lines and, in some instances, the power to the electrodes can be controlled on an electrode-by-electrode basis. Examples of electrophysiology devices include catheters, surgical probes, and clamps.

Currently known surgical probes which can be used to create lesions often include a handle, a relatively short shaft that is from 4 inches to 18 inches in length and either rigid or relatively stiff, and a distal section that is from 1 inch to 10 inches in length and either malleable or somewhat flexible. One or more electrodes are carried by the distal section. Surgical probes are used in epicardial and endocardial procedures, including open heart procedures and minimally invasive procedures where access to the heart is obtained via a thoracotomy, thoracostomy or median sternotomy. Exemplary surgical probes are disclosed in U.S. Pat. No. 6,142,994, the content of which is incorporated herein by reference.

Clamps, which have a pair of opposable clamp members that may be used to hold a bodily structure or a portion thereof, are used in many types of surgical procedures. Lesion-creating electrodes have also been secured to certain types of clamps. Examples of clamps which carry lesion creating electrodes are discussed in U.S. Pat. No. 6,142,994, and U.S. Patent Publication Nos. 2003/0158549, 2004/0059325, and 2004/024175, the contents of which are incorporated herein by reference. Such clamps can be useful when the physician intends to position electrodes on opposite sides of a body structure in a bipolar arrangement.

Although these and other proposed treatment devices and methods may provide real benefits to patients in need thereof, still further advances would be desirable. For example, there continues to be a need for improved ablation systems and methods that can be used by surgeons to treat patient tissue or anatomical features having various sizes, shapes, densities, and the like. Embodiments of the present invention provide solutions that address the problems which may be associated with known techniques, and hence provide answers to at least some of these outstanding needs.

BRIEF SUMMARY OF THE INVENTION

An electrode assembly in accordance with embodiments of the present invention includes an electrode that is connected to at least two power supply lines. An electrode assembly (or a plurality of electrode assemblies) may be used in electrophysiology devices including, but not limited to, catheters, surgical probes and clamps. In one exemplary bipolar clamp implementation, an electrode assembly is provided on one clamp member and a similar electrode assembly (e.g. with an electrode and a pair of power return lines) is provided on the other clamp member. In some cases, an electrode assembly may include a single power return line. Such a clamp may be used to form long, continuous lesions without the gaps that may sometimes occur when a plurality of spaced power transmitting electrodes are positioned opposite a plurality of spaced return electrodes. The individual clamp members may include rotatable jawbone members that can be adjusted to be set or fixed at desired angular degrees about their longitudinal axis, thereby enabling a surgeon to create lesion lines in any of a variety of three dimensional configurations.

Exemplary systems and methods are well suited for treating patients exhibiting atrial fibrillation, for example by performing tissue ablations and creating lesions at or near the pulmonary veins, as cardiac tissue near the base of the pulmonary veins may harbor sources of aberrant electrical signals that cause the left atrium to contract irregularly. By creating scar or burn tissue around these sources, which may be located at the base of the pulmonary veins, it is possible to restore the left atrium to sinus rhythm, so that the left atrium properly receives signals from the SA or AV node.

For example, treatments may involve forming a box lesion on cardiac tissue, so as to remove, diminish, or block off unwanted eddy currents and signals.

In some instances, jaw clamps are used to squeeze or "bite" into a portion of the left atrium, and to deliver a burning ablation to the tissue. The clamps can then be removed, leaving a circular or rounded scar. Ablation clamps can be used during a sternotomy or open chest procedure, for example which may involve a valve repair procedure. In some cases, ablation clamps can be used to deliver ablation during a bypass surgery. Hence, embodiments of the present invention encompass techniques for treating atrial fibrillation as part of a concomitant procedure.

Often, the jaw clamps will squeeze together two layers of tissue. When the tissue layers are pressed sufficiently tightly against one another, there may be no blood between the layers. One jaw clamp can include an active (−) electrode, and the opposing jaw clamp can include a ground/return (+) electrode. Application of energy through the electrodes operates to heat the tissue, thereby forming a lesion. Embodiments of the present invention provide convenient and efficient mechanisms to change the orientation of the jaw clamps throughout various degrees or rotation. This flexibility allows the surgeon to use a single clamp design to easily access or approach the patient anatomy from different directions. For example, the surgeon may choose to treat cardiac tissue using an inferior approach or using a superior approach. In some cases, the path through which the device is maneuvered may depend on the size of the patient. For example, a physician may elect a superior approach with a larger patient. In some cases, the path through which the device is maneuvered may depend on the patient's anatomy. For example, when approaching the heart, the physician may wish to pursue an inferior approach due to the location of branching great vessels and the conical shape of the rib cage. In some cases, the path through which the device is maneuvered may depend on the location of an access port or incision. For example, if an incision is made slightly high relative to the heart, the physician may chose a superior approach.

The clamp jaws can be oriented so that they form an ablation curve that intersects the curve of the atrium. This intersection allows the jaws to bite into the atrium and make an encircling lesion about the base of the pulmonary veins. When holding the device handle, with the distal jaw ends extending away from the user, if the jaws bend to the right they can be considered to be in a "right curve" orientation. Similarly, when holding the device handle, with the distal jaw ends extending away from the user, if the jaws bend to the left they can be considered to be in a "left curve" orientation. Embodiments of the present invention encompass reversible jaw clamps, that can be switched between right curve and left curve orientations. Hence, embodiments provide single devices that can be used for inferior approaches as well as for superior approaches. Similarly, embodiments provide single devices that can be used to deliver energy at or near the left pulmonary veins, as well as at or near the right pulmonary veins. Toward this end, embodiments provide click-jaw embodiments whereby the operator may rotate the orientation of a curved jaw clamp by engaging an actuation mechanism or button of the device. Such rotation or actuation can be performed using two fingers, such as the thumb and forefinger. In some cases, the physician may perform a squeeze-and-release motion to rotate a jaw clamp, for example by ninety degrees. For example, an instroke can rotate the jaw by forty five degrees, and an outstroke can rotate the jaw by another forty five degrees. During actuation, an internal jawbone may rotate within and relative to an external flexible boot to which an electrode is attached. During jawbone rotation, opposing electrodes of a clamp device may remain facing one another. Two squeeze-and-release motions may result in a one hundred and eighty degree rotation of the jaw clamp. These actuation motions can be performed without touching or engaging the jaw electrode itself. In some cases, the physician may rotate the jaw with one hand, while holding the device handle with the other hand.

In addition to the left curve and right curve orientations discussed above, surgeons may wish to use treatment devices of the present invention where the jaw clamps are disposed in an "up curve" orientation, which may be useful for performing a scooping motion when navigating down and underneath the patient's vessels. Such techniques may be useful where procedures benefit from special device positioning, or where procedures are performed in a smaller patient. Optionally, surgeons may wish to use treatment devices of the present invention where the jaw clamps are disposed in an "down curve" orientation, which may be useful for performing a dome procedure. For example, the physician may form a small cut in the atrial wall, slide one jaw inside of the atrium, and perform a superior dome lesion between the pulmonary vein pairs while one jaw clamp is inside the atrium, and one jaw clamp is on the outside.

Embodiments of the present invention may include temperature control features. For example, the amount of power delivered through one or more electrodes can be controlled based on the temperature of the tissue or an indicator of tissue temperature.

In one aspect, embodiments of the present invention encompass systems and methods for forming a lesion on a tissue of a patient. An exemplary system may include an actuator handle assembly, and a clamp assembly coupled with the actuator handle assembly. The clamp assembly may include a first jaw mechanism and a second jaw mechanism. The first jaw mechanism can have a first flexible boot, a first flexible ablation member coupled with the first flexible boot, and a first rotatable jawbone disposed within the first flexible boot. The second jaw mechanism can have a second flexible boot, a second flexible ablation member coupled with the second flexible boot, and a second rotatable jawbone disposed within the second flexible boot. In some cases, the first flexible ablation member includes a serpentine electrode. In some cases, the second flexible ablation member includes a serpentine electrode. Optionally, the first flexible ablation member can have a fishbone electrode. Similarly, the second flexible ablation member can have a fishbone electrode. The first and second flexible boots can be configured such that the first and second ablation members face toward each other upon rotation of the first jawbone, the second jawbone, or both. A treatment system may also include a cooling system having a fluid return lumen, and a fluid delivery lumen disposed within the fluid return lumen. In some cases, a treatment system includes a pull and rotate rotational assembly. In some cases, a treatment system includes a ball and detent rotational assembly. In some cases, a treatment system includes a side ratchet rotational assembly. In some cases, a treatment system includes a tuning fork rotational assembly. Optionally, a treatment system can include a radiofrequency generator capable of delivering a radiofrequency power signal to the clamp assembly. The first ablation element can include a member selected from the group consisting of a radiofrequency ablation element, an infrared laser ablation element, a high intensity focused ultrasound ablation element, a microwave ablation element, a cryoablation ablation element, a chemical agent ablation element, a biological agent ablation element, and a radiation ablation element. In some embodiments, the first and second jaw mechanisms are configured to provide an ablation zone shape that rotates as a result of rotation of the first and second jawbones.

In another aspect, embodiments of the present invention encompass treatment systems for forming a lesion on a tissue of a patient. Exemplary treatment systems may include an actuator handle assembly, and a clamp assembly coupled with the actuator handle assembly. The clamp assembly may include a first jaw mechanism and a second jaw mechanism. The first jaw mechanism may include a first flexible boot, a first flexible ablation member coupled with the first flexible boot, and a first rotatable jawbone disposed within the first flexible boot. The second jaw mechanism may include a second flexible boot, a second flexible ablation member coupled with the second flexible boot, and a second rotatable jawbone disposed within the second flexible boot. In some instances, the first flexible ablation member includes a serpentine electrode. In some instances, the second flexible ablation member includes a serpentine electrode. In some instances, the first flexible ablation member includes a fishbone electrode. In some instances, the second flexible ablation member includes a fishbone electrode. Optionally, the first and second flexible boots can be configured such that the first and second ablation members face toward each other upon rotation of the first jawbone, the second jawbone, or both. In some instances, a treatment system may include a cooling system having a fluid return lumen, and a fluid delivery lumen disposed within the fluid return lumen. In some instances, a treatment system may include a pull and rotate rotational assembly. In some instances, a treatment system may include a ball and detent rotational assembly. In some instances, a treatment system may include a side ratchet rotational assembly. In some instances, a treatment system may include a tuning fork rotational assembly. Optionally, a treatment system may include a radiofrequency generator capable of delivering a radiofrequency power signal to the clamp assembly.

According to some embodiments, an ablation element can include a radiofrequency ablation element, an infrared laser ablation element, a high intensity focused ultrasound ablation element, a microwave ablation element, a cryoablation ablation element, a chemical agent ablation element, a biological agent ablation element, a radiation ablation element, or the like. In some embodiments, the first and second jaw mechanisms can be configured to provide an ablation zone shape that rotates as a result of rotation of the first and second jawbones. In some instances, a treatment system may include a push and release rotational assembly.

In another aspect, embodiments of the present invention encompass methods of delivering an ablation to a tissue of a patient. An exemplary method may include engaging a patient with a treatment system having an actuator handle coupled with a clamp assembly, where the clamp assembly includes a first jaw mechanism and a second jaw mechanism, the first jaw mechanism includes a first flexible boot, a first flexible ablation member coupled with the first flexible boot, and a first rotatable jawbone disposed within the first flexible boot, and the second jaw mechanism includes a second flexible boot, a second flexible ablation member coupled with the second flexible boot, and a second rotatable jawbone disposed within the second flexible boot. Methods may also include delivering an ablation energy through the first flexible ablation member to the tissue of the patient. In some cases, the first flexible ablation member includes a serpentine electrode. In some cases, the second flexible ablation member includes a serpentine electrode. Optionally, the first flexible ablation member can have a fishbone electrode. Similarly, the second flexible ablation member can have a fishbone electrode. Optionally, the first and second flexible boots can be configured such that the first and second ablation members face toward each other throughout rotation of the first jawbone, the second jawbone, or both. Some methods may include cooling the treatment system with a cooling system. Some methods may include rotating the first rotatable jawbone with a pull and rotate rotational assembly. Some methods may include rotating the first rotatable jawbone with a ball and detent rotational assembly. Some methods may include rotating the first rotatable jawbone with a side ratchet rotational assembly. Some methods may include rotating the first rotatable jawbone with a tuning fork rotational assembly. Some methods may include rotating the first rotatable jawbone with a push and release rotational assembly.

In yet another aspect, embodiments of the present invention encompass treatment systems for forming a lesion on a tissue of a patient which may include, for example, an actuator handle assembly, a clamp assembly having a first jaw mechanism and a second jaw mechanism, a first push and release rotational assembly coupling the actuator handle with the first jaw mechanism, and a second push and release rotational assembly coupling the actuator handle assembly with the second jaw mechanism. The first jaw mechanism can include a first flexible boot, a first flexible ablation member coupled with the first flexible boot, and a first rotatable jawbone disposed within the first flexible boot. The second jaw mechanism can include a second flexible boot, a second flexible ablation member coupled with the second flexible boot, and a second rotatable jawbone disposed within the second flexible boot. In some instances, the first push and release rotational assembly comprises a first frame button and a first leaf spring. In some instances, the first frame button includes an engagement button, an upper horizontal arm having an upper tooth, a lower horizontal arm having a lower tooth, and a vertical arm having a vertical tooth. Optionally, the leaf spring can include an engagement tab, and the first push and release rotational assembly can include a jawbone base having an engagement aperture that receives the engagement tab. In some instances, the first push and release rotational assembly includes a jawbone base having a jawbone base tooth that can engage an upper tooth, a lower tooth, or a vertical tooth of the first frame button.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIGS. 1A and 1B illustrate aspects of treatment systems and methods according to embodiments of the present invention.

FIGS. 10A to 10C illustrate aspects of treatment systems and methods according to embodiments of the present invention.

DETAILED DESCRIPTION OF THE INVENTION

Figure 1B:
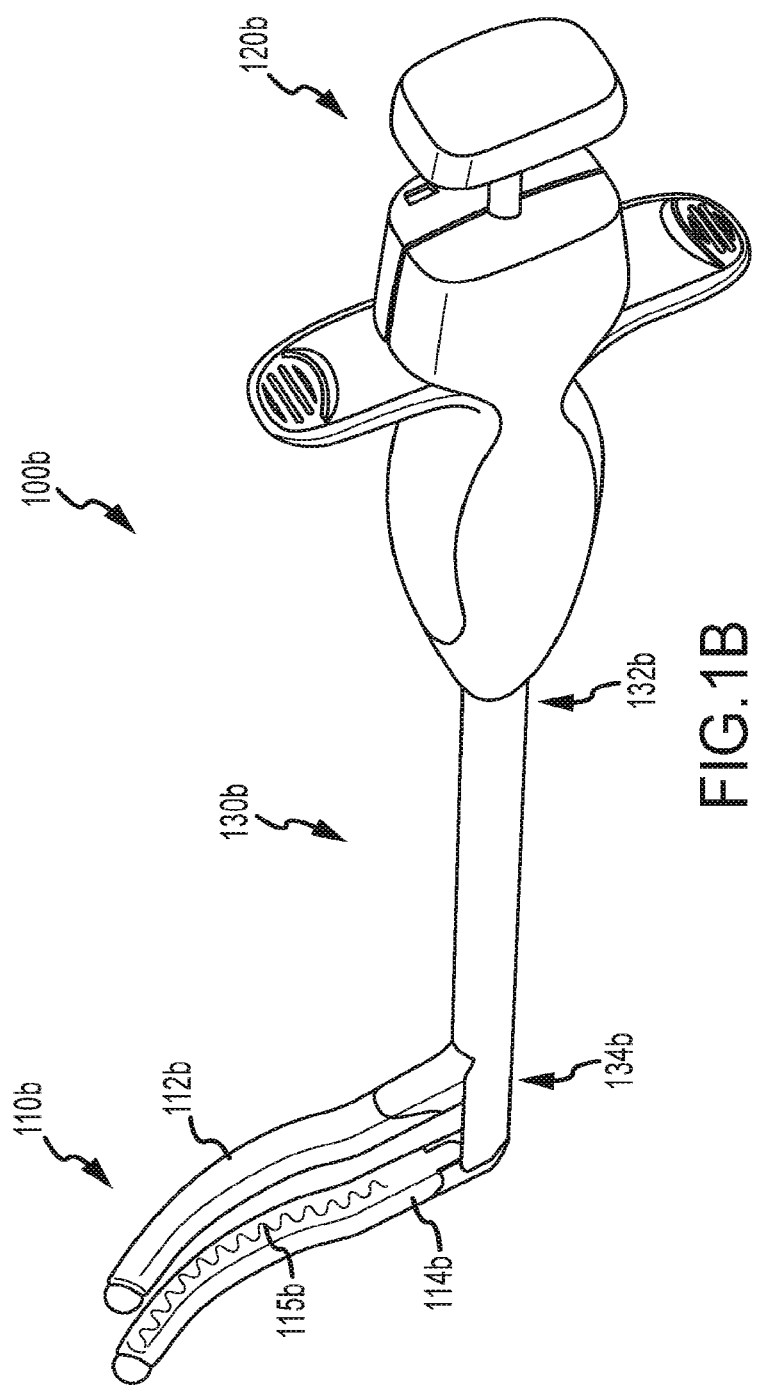

Embodiments of the present invention encompass systems and methods that involve a treatment system having a disposable dedicated bipolar clamp. In some cases, a bipolar clamp device may include cooled RF technology. Optionally, treatment devices may include a flexible serpentine plate electrode. Treatment devices may be adjustable for ease of use by the surgeon in any of a variety of configurations, including a right hand configuration, a left hand configuration, a jaws up configuration, and a jaws down configuration. The treatment device can adopt such configurations as the surgeon adjustably flips or rotates the jaws through various degrees of angular rotation. In some cases, a treatment device includes a symmetric, unified release trigger.

Turning now to the drawings, FIG. 1A illustrates aspects of a treatment system 100a according to embodiments of the present invention. Treatment system 100a includes a clamp assembly 110a, an actuator assembly 120a, and a coupling assembly 130a in operative association with both the clamp assembly and the actuator assembly. Clamp assembly 110a includes a first jaw mechanism 112a and a second jaw mechanism 114a. Coupling assembly 130a may include a shaft or other elongate member that allows the physician or operator to access or reach a surgical site with the clamp assembly, when the physician is holding actuator assembly 120a. Coupling assembly 130a includes a proximal end 132a and a distal end 134a. As shown here, clamp assembly 110a is coupled with distal end 134a of coupling assembly 130a, and actuator assembly 120a is coupled with proximal end 132a of coupling assembly 130a. Clamp assembly 110a is depicted in a generally closed configuration, such that first jaw mechanism 112a contacts or is situated near second jaw mechanism 114a. In some cases, a treatment system may present a disposable dedicated bipolar clamp having single-position jaws and a symmetric jaw-release on a plunger style body.

FIG. 1B illustrates aspects of a treatment system 100b according to embodiments of the present invention. Treatment system 100b includes a clamp assembly 110b, an actuator assembly 120b, and a coupling assembly 130b in operative association with both the clamp assembly and the actuator assembly. Clamp assembly 110b includes a first jaw mechanism 112b and a second jaw mechanism 114b. Coupling assembly 130b may include a shaft or other elongate member that allows the physician or operator to access or reach a surgical site with the clamp assembly, when the physician is holding actuator assembly 120b. Coupling assembly 130b includes a proximal end 132b and a distal end 134b. As shown here, clamp assembly 110b is coupled with distal end 134b of coupling assembly 130b, and actuator assembly 120b is coupled with proximal end 132b of coupling assembly 130b. Clamp assembly 110b is depicted in a generally open configuration, such that first jaw mechanism 112b does not contact or is situated at a distance from second jaw mechanism 114b. The treatment system includes a serpentine electrode or ablation member 115b disposed on second jaw mechanism 114b. The first jaw mechanism 112b includes a corresponding electrode or ablation member (not shown) that faces toward ablation member 115b. In some cases, a treatment system may present a disposable dedicated bipolar clamp having flip-jaws and a symmetric jaw-release on a plunger style body.

Figure 2:
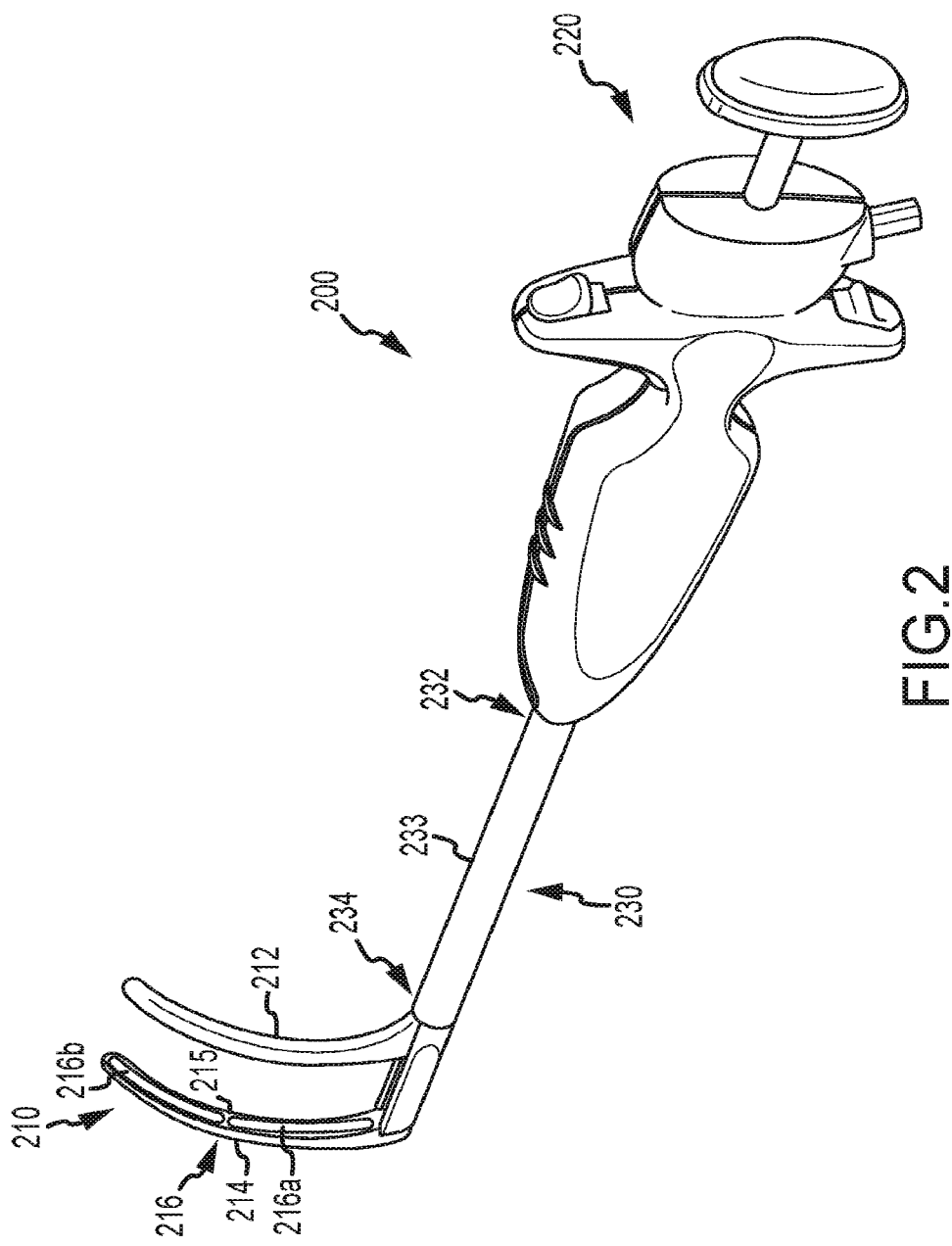
FIG. 2 illustrates aspects of treatment systems and methods according to embodiments of the present invention.

FIG. 2 shows aspects of a treatment system 200 according to embodiments of the present invention. Treatment system 200 includes a clamp assembly 210, an actuator assembly 220, and a coupling assembly 230 in operative association with both the clamp assembly and the actuator assembly. Clamp assembly 210 includes a first jaw mechanism 212 and a second jaw mechanism 214. First jaw mechanism 212 is disposed proximal to second jaw mechanism 214. The jaw mechanisms may include ablation assemblies, as well as support assemblies for holding the ablation assemblies. For example, as shown in FIG. 2, second jaw mechanism 214 includes an ablation assembly 216 having a proximal electrode 216a and a distal electrode 216b. The proximal and distal electrodes are coupled with a support assembly 215. First jaw mechanism 212 provides a similar configuration, and has one or more electrodes (not shown) that face toward electrodes 216a, 216b of distal jaw mechanism 214. In use, the surgeon or operator can use the handle or actuator assembly 220 for manipulating the treatment system, opening and closing the jaw mechanisms, activating ablation members such as electrodes 216a, 216b, and the like. Treatment system 200 can be generally configured to be introduced through a minimally invasive sheath, trocar, or incision. In some cases, treatment system 200 can be used in open surgical procedures. Coupling assembly 230 may include a shaft or other elongate member 233. In some embodiments, the shaft or elongate member may be malleable. Optionally, elongate member 233 may articulate about at least one joint and/or may be steerable for positioning the system 200. Elongate member may be made of any suitable material, such as metal, ceramic, polymers, or any combination thereof, and may be rigid along its entire length or rigid in one or more parts and flexible in one or more parts. In some embodiments, ablation assembly 216, support assembly 215, or both, are coupled with or otherwise in operative association with actuator assembly 220, optionally via coupling assembly 230. According to some embodiments, the jaw or tubular shaft elements may include a high strength material such as metal, carbon fiber, or the like.

Clamp assembly 210 may be disposed on or near a distal end 234 of coupling assembly 230, and can be generally configured to open and close to grasp epicardial or other tissue between the opposing jaw mechanisms 212, 214. As shown here, actuator assembly 220 is coupled with coupling assembly 230 via a proximal portion 232 of the coupling assembly. An ablation assembly 216 may use any suitable energy source for ablating tissue. In some embodiments, multiple ablation members may be used in a bipolar treatment technique. For example, one electrode (e.g electrode 216a) of a bipolar ablation member may be coupled with one opposing jaw (e.g. distal jaw 214) and another corresponding electrode (not shown) may be coupled with the other opposing jaw (e.g. proximal jaw 212).

Aspects of clamp assembly 210, such as jaw mechanisms 212, 214 or ablation assemblies 216, may be shaped to contact and ablate the epicardial tissue in a pattern such as, but not limited to, a U-shaped pattern, an L-shaped pattern, a circular pattern, a nonlinear pattern, or a linear pattern. Actuator assembly 220 may enable the physician to perform one or more various system operations, such as opening and closing the jaw mechanisms 212, 214, activating an ablation assembly 216, changing an angle of orientation of a jaw mechanism 212, 214, straightening or bending a jaw mechanism 212, 214, or the like. For example, an actuator assembly may include a trigger-like actuator. Optionally, an actuator assembly may include a turnable dial.

Generally, a jaw mechanism 212, 214 may have any suitable configuration for contacting a surface of a heart, for grasping epicardial or other tissue to be ablated, for placing ablation members 216a, 216b in contact with tissue to be ablated, or for any combination thereof. As such, jaw mechanisms 212, 214 may be straight, curved, bent, or otherwise configured for contacting, grasping, or ablating tissue, or any combination thereof. In some embodiments, jaw mechanisms 212, 214 may be adjustable via actuator assembly 220, so as to allow their shapes to be bent, straightened, or the like, during a procedure. In some cases, jaw mechanisms 212, 214, can be retractable. For example, jaw mechanisms 212, 214 may be retracted within coupling assembly 230 upon one or more occasions during an operation. Retraction may help protect a patient as well as a jaw mechanism during insertion and advancement of the system within the patient.

In some embodiments, the treatment system may further include an insulation member at least partially surrounding or covering one or more the actuator assembly, coupling assembly, or clamp assembly. Such an insulation member can operate to protect body structures in the vicinity of the epicardial tissue from being ablated or damaged due to heat or electrical current. In some cases, ablation members such as electrodes 216a, 216b may be adjustable to deliver two or more varying amounts of ablative energy to two or more locations on the epicardial tissue. Various embodiments may further include at least one sensor for sensing a quantity of ablation provided by the ablation member to the tissue.

Figure 3:
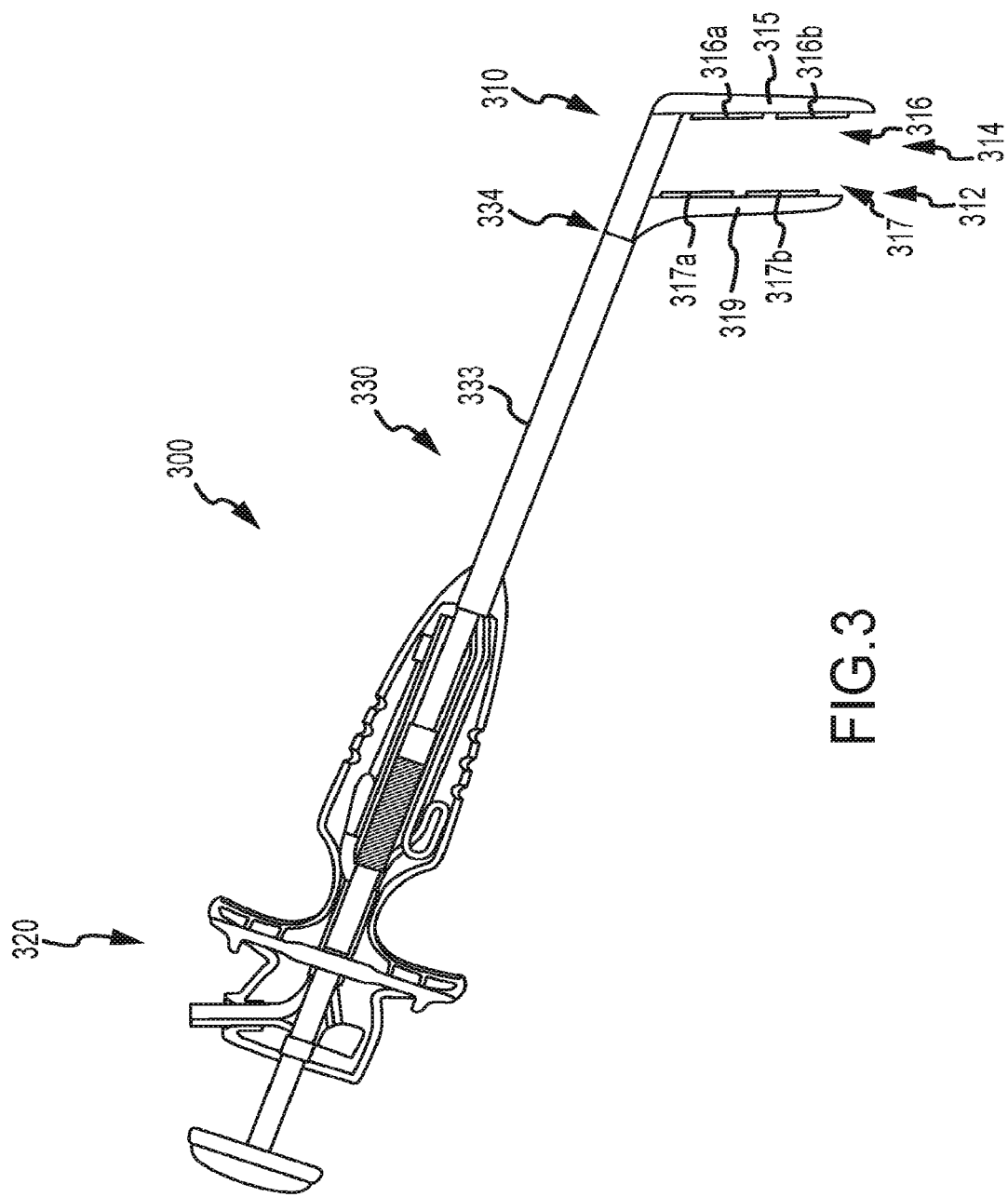
FIG. 3 illustrates aspects of treatment systems and methods according to embodiments of the present invention.

FIG. 3 shows aspects of a treatment system 300 according to embodiments of the present invention. Treatment system 300 includes a clamp assembly 310, an actuator assembly 320, and a coupling assembly 330 in operative association with both the clamp assembly and the actuator assembly. Clamp assembly 310 includes a first jaw mechanism 312 and a second jaw mechanism 314. First jaw mechanism 312 is disposed proximal to second jaw mechanism 314. The jaw mechanisms may include ablation assemblies, as well as support assemblies for holding the ablation assemblies. For example, as shown in FIG. 3, second jaw mechanism 314 includes an ablation assembly 316 having a proximal electrode 316a and a distal electrode 316b. The proximal and distal electrodes are coupled with a support assembly 315. First jaw mechanism 312 provides a similar configuration, and includes an ablation assembly 317 and a support assembly 319. The ablation assembly 317 includes a proximal electrode 317a and a distal electrode 317b that face toward electrodes 316a, 316b, respectively, of distal jaw mechanism 314. In use, the surgeon or operator can use the handle or actuator assembly 320 for manipulating the treatment system, opening and closing the jaw mechanisms, activating ablation members such as electrodes 316a, 316b, 317a, 317b, and the like. Treatment system 300 can be generally configured to be introduced through a minimally invasive sheath, trocar, or incision. In some cases, treatment system 300 can be used in open surgical procedures. Coupling assembly 330 may include a shaft or other elongate member 333. In some embodiments, the shaft or elongate member may be malleable. Optionally, elongate member 333 may articulate about at least one joint and/or may be steerable for positioning the system 300. Elongate member may be made of any suitable material, such as metal, ceramic, polymers, or any combination thereof, and may be rigid along its entire length or rigid in one or more parts and flexible in one or more parts. In some embodiments, ablation assemblies 316, 317, support assemblies 315, 319, or any combination thereof, are coupled with or otherwise in operative association with actuator assembly 320, optionally via coupling assembly 330.

Clamp assembly 310 may be disposed on or near a distal end 334 of coupling assembly 330, and can be generally configured to open and close to grasp epicardial or other tissue between the opposing jaw mechanism 312, 314. An ablation assembly 316 may use any suitable energy source for ablating tissue. In some embodiments, multiple ablation members may be used in a bipolar treatment technique. For example, one electrode (e.g electrode 316a) of a bipolar ablation member may be coupled with one opposing jaw (e.g. distal jaw 314) and another corresponding electrode (e.g. electrode 317a) may be coupled with the other opposing jaw (e.g. proximal jaw 312). Optionally, ablation assemblies may include one unipolar ablation device or any of the ablation devices described elsewhere herein.

Aspects of clamp assembly 310, such as jaw mechanisms 312, 314 or ablation assemblies 316, 317 may be shaped to contact and ablate the epicardial tissue in a pattern such as, but not limited to, a U-shaped pattern, an L-shaped pattern, a circular pattern, or a linear pattern. Actuator assembly 320 may enable the physician to perform one or more various system operations, such as opening and closing the jaw mechanisms 312, 314, activating an ablation assembly 316, 317, changing an angle of orientation of a jaw mechanism 312, 314, straightening or bending a jaw mechanism 312, 314, or the like. For example, an actuator assembly may include a trigger-like actuator. Optionally, an actuator assembly may include a turnable dial.

Generally, a jaw mechanism 312, 314 may have any suitable configuration for contacting a surface of a heart, for grasping epicardial or other tissue to be ablated, for placing ablation members 316a, 316b, 317a, 317b in contact with tissue to be ablated, or for any combination thereof. As such, jaw mechanisms 312, 314 may be straight, curved, bent, or otherwise configured for contacting, grasping, or ablating tissue, or any combination thereof. In some embodiments, jaw mechanisms 312, 314 may be adjustable via actuator assembly 320, so as to allow their shapes to be bent, straightened, or the like, during a procedure. In some cases, jaw mechanisms 312, 314, can be retractable. For example, jaw mechanisms 312, 314 may be retracted within coupling assembly 330 upon one or more occasions during an operation. Retraction may help protect a patient as well as a jaw mechanism during insertion and advancement of the system within the patient. Ablation members such as electrodes 316a, 316b, 317a, 317b, may be bipolar RF members, unipolar RF members, or any other suitable ablation devices.

In some cases, the tissue treatment systems can have a spring loaded mechanism that allows an indirect connection between the handle and the clamp members or jaws. Hence, during the initial stage of the clamping process, there can be a 1:1 ratio between movement of the handle and movement of the clamp members or jaws. However, during the later stage of the clamping process when the clamp members or jaws are sufficiently close to one another, optionally applying sufficient pressure on the atrium, there may not be a 1:1 ratio between movement of the handle and movement of the clamp members or jaws. Rather, a handle movement results in a smaller corresponding movement of the clamp members and jaws. The ablation and monitoring assemblies can be configured as inserts that are removable with respect to the clamp members or jaws. According to some embodiments, the ablation and monitoring assemblies may be disposable, replaceable, or both, and the clamp or support member can be sterilizable, reusable, or both.

According to some embodiments, a treatment system can be convertible; that is, the system can convert from a bipolar configuration to monopolar configuration and back to a bipolar configuration according to the surgeon's need or decision. In some cases, a monopolar device does not include jaws and can be in the form of a malleable electrode that presents a contact strip or surface to deliver RF energy to tissue from any direction and from any shape it is bent into. In some cases, a monopolar probe resides within or is a part of the handle or shaft structure of a bipolar clamp. The monopolar electrode can reside in one jaw and act as the active electrode when in a bipolar configuration, and the other jaw can act as the indifferent (ground) electrode. When the surgeon converts the device to a monopolar configuration, for example by pulling the monopolar probe assembly out of the rest of the device, the probe acts as a monopolar device because the return path for energy is now through the ground pad on the patient. When the surgeon is done with the monopolar RF application, he or she may choose to straighten the electrode and reinsert it into the bipolar handle to make that part functional again.

In some embodiments, the treatment system may further include an insulation member at least partially surrounding or covering one or more the actuator assembly, coupling assembly, or clamp assembly. Such an insulation member can operate to protect body structures in the vicinity of the epicardial tissue from being ablated or damaged due to heat or electrical current. In some cases, ablation members such as electrodes 316a, 316b, 317a, 317b may be adjustable to deliver two or more varying amounts of ablative energy to two or more locations on the epicardial tissue. Various embodiments may further include at least one sensor for sensing a quantity of ablation provided by the ablation member to the tissue.

Actuator assembly 320 may include a symmetric, unified release trigger. In some cases, the actuator assembly may have a plurality of separated ratchet teeth. In use, the operator or surgeon may close or clamp the jaw mechanisms together by activating a handle or plunger of the actuator assembly. Relatedly, the operator may release the jaw mechanisms from a clamped configuration by activating a release trigger of the actuator assembly. In some cases, a release trigger may include a button or a slide mechanism. The treatment system may be spring loaded, such that release of a ratchet mechanism allows release of the jaw mechanisms and the spring allows an automatic position return of the ratchet mechanism.

Embodiments of the present invention encompass a variety of mechanisms which may be used to open or close the jaw mechanisms. In some cases, treatment systems may include a pliers assembly configured to open or close the jaw mechanisms. In some cases, treatment systems may include a scissors assembly configured to open or close the jaw mechanisms. Optionally, a pliers or scissors assembly can include two members having a central pivot, whereby the closing of the handle portion closes the distal portions by changing the angle between the two members from something greater than zero to something less than the starting number, generally bringing together the distal ends. In some cases, treatment systems may include a sliding mechanism or assembly configured to open or close the jaw mechanisms. Optionally, the treatment system may include a plunger assembly configured to open or close the jaw mechanisms. Exemplary actuator assemblies may include pistol grips, hinged grips, and the like. In some cases, an actuator assembly may provide for direct activation or coupling of the jaw mechanisms, such that when the surgeon moves a portion of the actuator assembly by a given amount, the actuator assembly causes the jaw mechanism to move the same amount in a 1:1 ratio. In some cases, an actuator assembly may provide for indirect activation or coupling of the jaw mechanisms, such that when the surgeon moves a portion of the actuator by a given amount, the actuator assembly causes the jaw mechanism to move in differing amount. An actuator assembly may be configured to limit, attenuate, or amplify the amount of clamping force applied to a tissue based on the amount of squeezing or activating force manually applied by a surgeon.

In some instances, the treatment system can include a jaw release trigger that is symmetric about two planes, and that allows or actuates release of the jaw mechanisms such that the jaw mechanisms translate relative to each other in an upward or downward manner. Such actuation can be performed without changing the jaw release finger motion. In some cases, a jaw mechanism release or opening action can be accomplished without changing the operator's basic hand position on the handle. The system can be configured so that the operator can reach or use the release trigger located in an ergonomically efficient position. A release trigger may be self-centering and momentary. In some cases, a release trigger can have a single re-centering spring that is captive in the body shell and actuated at either end by a finger that reaches into the entrapping space from the moving trigger portion from either end to compress the spring as the trigger is pushed off-center.

Figure 4:
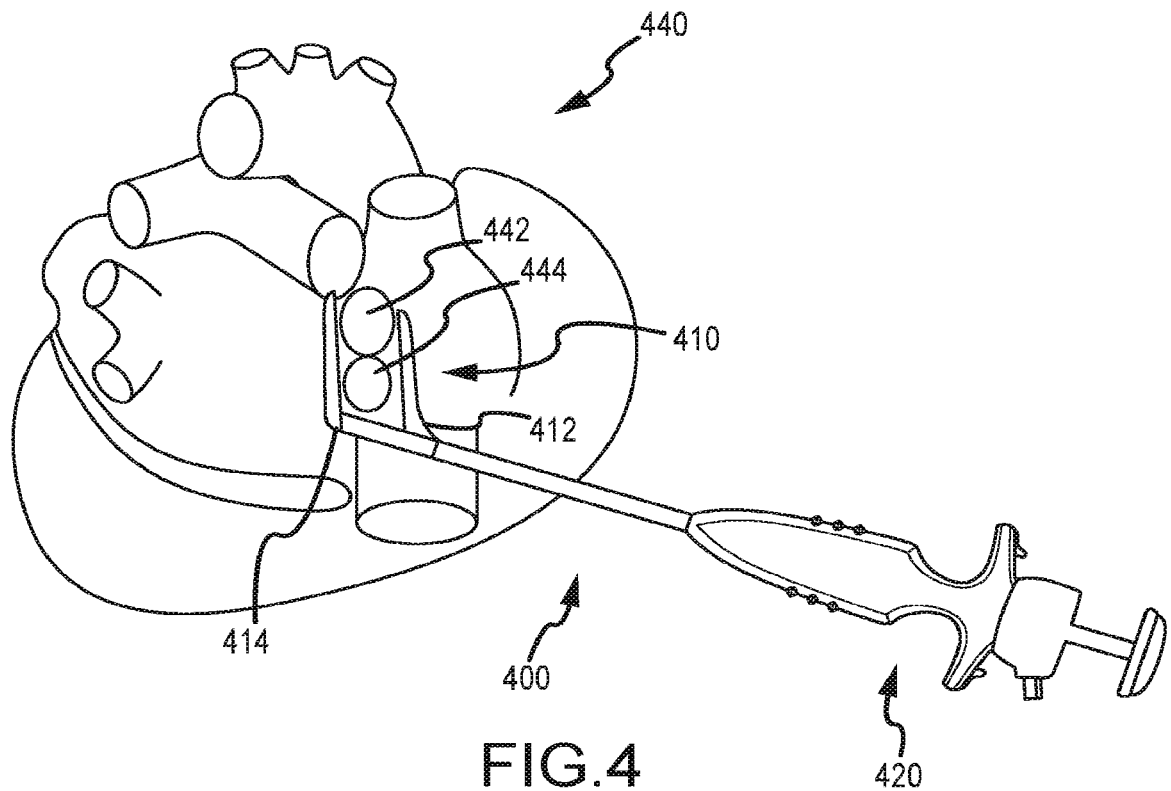
FIGS. 4 and 4A illustrate aspects of treatment systems and methods according to embodiments of the present invention.

FIG. 4 shows a treatment system 400 in a position for performing an ablation or treatment procedure on epicardial tissue of heart 440. Treatment system 400 includes a clamp assembly 410 having first and second jaw mechanisms 412, 414, and can be configured to ablate in a pattern approximating two lines adjacent the right pulmonary veins 442, 444. As discussed elsewhere herein, jaw mechanisms 412, 414 can be rotated as desired to provide a variety of ablation configurations. Additionally, treatment system 400 may be moved to a variety of positions to ablate multiple patterns in multiple locations on the epicardial tissue.

Treatment system 400 includes a handle or actuator assembly 420 disposed toward a proximal portion of the system. As shown here, first and second jaw mechanisms 412, 414, which may include two bipolar ablation clamps, are disposed toward a distal portion of the system. The jaw mechanisms 412, 414 can be curved or shaped. In some cases, jaw mechanisms 412, 414 are curved and adjustably rotatable, so that for each jaw mechanism 412, 414, a concave portion or arc of the jaw mechanism can face toward the handle, away from the handle, toward the right side of the handle, toward the left side of the handle, or toward any desired direction relative to the handle. In some cases, a jaw mechanism can be in connectivity with an ablation and monitoring assembly or ESU. During use, the tissue treatment system can be used to contact the cardiac tissue, which can be effectively accomplished for example by the curvature orientation. The curved or contoured shape of the jaw mechanisms can allow the treatment system to be placed on the heart without impinging upon the pulmonary veins. Hence, there is an increased likelihood of ablating tissue of the atrium, as opposed to ablating tissue of the pulmonary veins themselves. Treatment system 400 is well suited for use in surgical methods where access ports are not employed. For example, the treatment system can be inserted into a patient via a 3-4 inch thoracotomy. In use, the jaw mechanisms are placed at or near the ostia, and actuated until the opposing jaw members are approximately 2-5 millimeters apart. This action serves to collapse the atrium near the pulmonary veins. An ablation is performed, and the clamping pressure is released thus allowing the atrium to return to the uncompressed state.

Figure 4A:
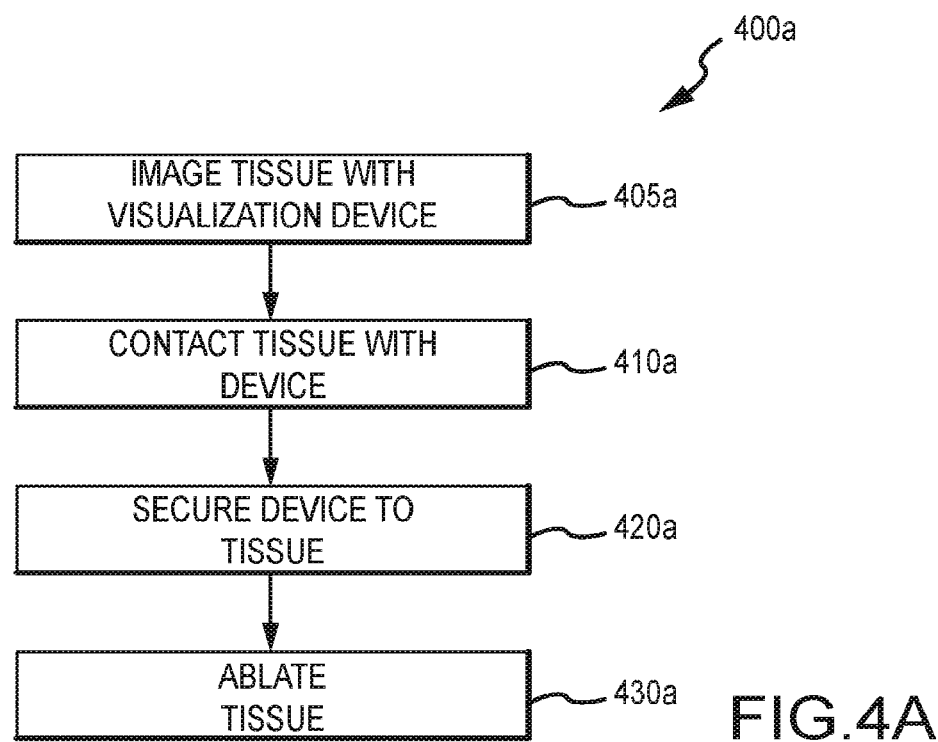

With reference now to FIG. 4A, a method 400a for ablating cardiac tissue, such as epicardial tissue, suitably includes contacting cardiac tissue with an ablation device 410a, securing the device to the tissue 420a and ablating at least a portion of the contacted, secured tissue 430a. Various embodiments can utilize additional steps or sub-steps of these three basic steps, although any such any additional steps or variations are optional. For example, in some embodiments, contacting the cardiac tissue 410a can be preceded by advancing the device into the patient through a minimally invasive introducer device. Contacting the device with the tissue 410a may include positioning the device using a positioning arm or other positioning device. In some embodiments, securing the device to the tissue 420a may also include invaginating a portion of epicardial tissue partially within one or more suction apertures and/or may include using one or more suction apertures to dissect through fatty tissue disposed over epicardium. Securing the device 420a may also involve securing with enough force to allow stabilization and/or positioning of the heart itself. And ablation of epicardial tissue 430a may involve ablation in any location or pattern as described elsewhere herein. According to some embodiments, a treatment method 400a may include imaging tissue with a visualization device 405a.

Electrosurgical Unit Operation

Figure 5:
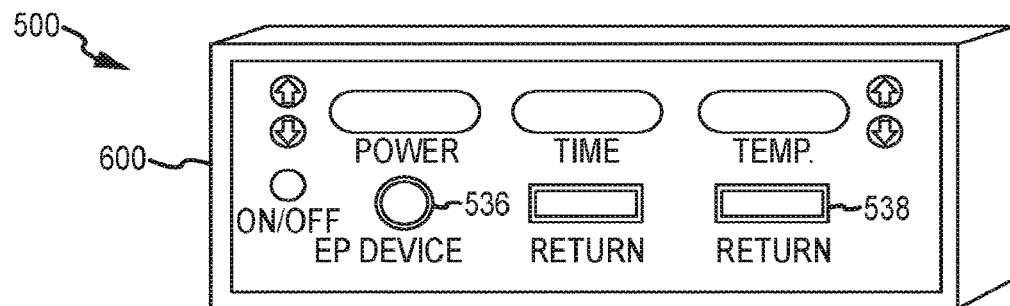
FIG. 5 illustrates aspects of treatment systems and methods according to embodiments of the present invention.
Figure 6A:
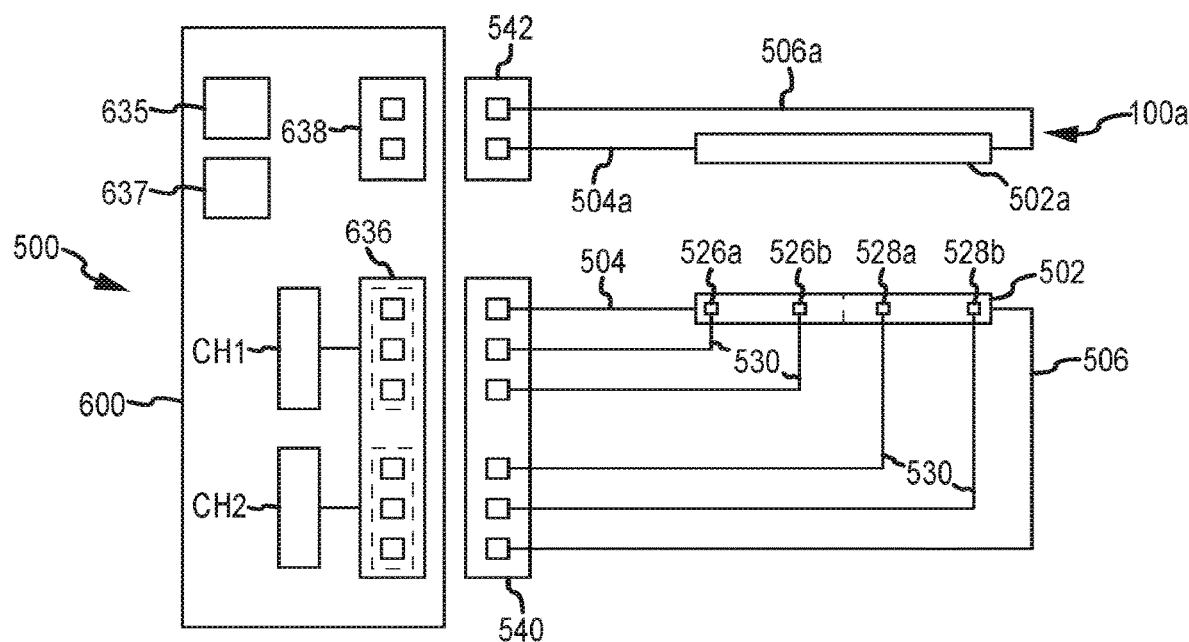
FIGS. 6A and 6B illustrate aspects of treatment systems and methods according to embodiments of the present invention.
Figure 6B:
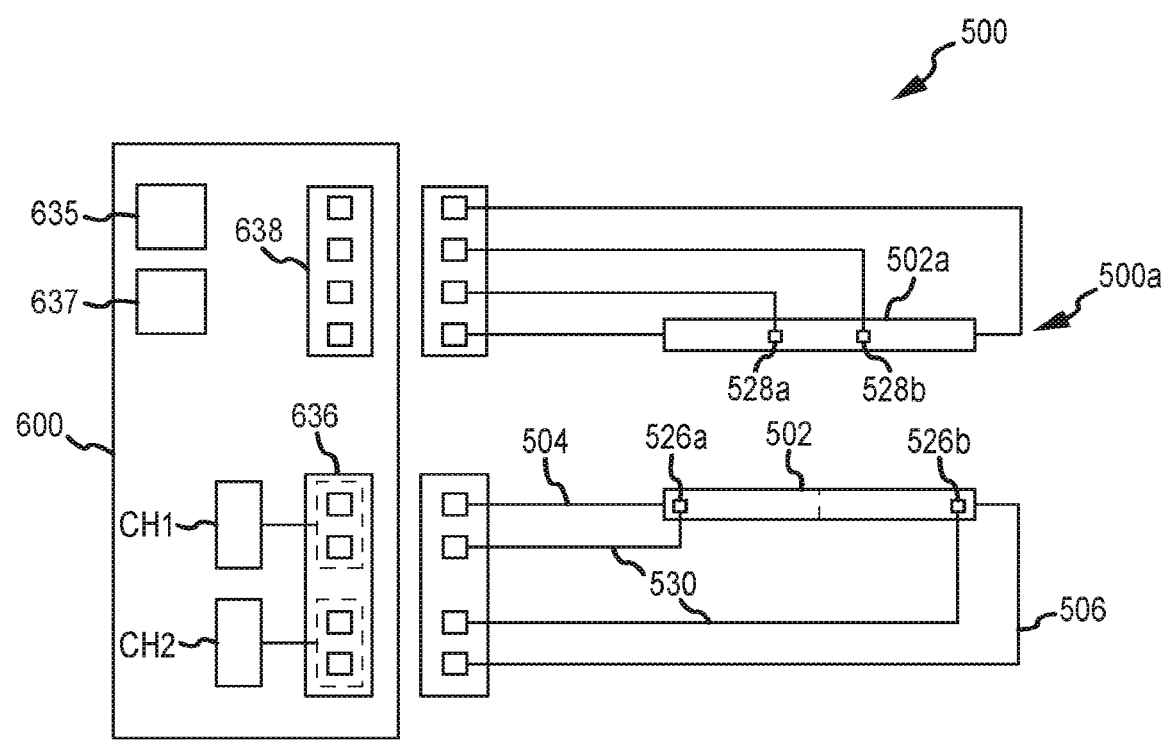

According to some embodiments, a treatment system may include or be coupled in operative association with an electrosurgical unit (ESU) that can supply and control power to an ablation assembly of the treatment system. FIGS. 5, 6A, and 6B illustrate aspects of a treatment system 500 that includes or is coupled with an ESU 600 that supplies and controls power, such RF power, during a treatment procedure. As shown here, ESU 600 includes a controller 635, a source of RF power 637 that is controlled by the controller, and a plurality of displays and buttons that are used to set the level of power supplied to one or more electrodes and the temperature at various locations on an electrode. The exemplary ESU 600 illustrated is operable in a bipolar mode, where tissue coagulation energy emitted by an electrode 502 is returned through a return electrode 502a, and a unipolar mode, where the tissue coagulation energy emitted by the electrode is returned through one or more indifferent electrodes (not shown) that are externally attached to the skin of the patient with a patch or one or more electrodes (not shown) that are positioned in the blood pool. The return electrode 502a, which in a bipolar configuration can be identical to the electrode 502, may be connected to the ESU 600 by a pair of power return lines 504a and 506a. The return electrode 502a and power return lines 504a and 506a together define a return electrode assembly 500a.

In some embodiments, return electrode 502a can be an indifferent electrode. In a bipolar configuration, an active electrode and an indifferent electrode can cooperate to help form a complete circuit of RF energy, for example when the two electrodes are placed across an anatomical feature such as the atria or other patient tissue. Energy can travel from the active electrode through the tissue to the indifferent electrode. An active electrode can be temperature-controlled, and can be coupled with one or more RF wires and one or more thermocouples. An indifferent electrode can provide a return path, optionally as a single wire, operating as a ground. In use, energy passing through the electrodes can raise the temperature of the intervening tissue, for example tissue which is secured between two clamp mechanisms. In turn, the heated tissue can raise the temperature of the electrodes. In some cases, active electrodes, indifferent electrodes, or both, can be cooled with internal cooling mechanisms.

In some instances, a treatment system may include multiple active electrodes along a length of a clamp. Each active electrode can be coupled with an RF wire that supplied energy to the electrode, and two thermocouple pairs. A thermocouple pair can include two wires joined by a thermocouple, and the thermocouple can be attached to the electrode, for example at an end portion of the electrode. The thermocouple pair can be used to monitor the temperature of the electrode, or a portion of the electrode. In some embodiments, an electrode is coupled with two thermocouple pairs, and the highest of the two temperatures sensed by the thermocouple pairs can be used to control RF energy delivery to the electrode.

ESU 600 can be provided with a power output connector 636 and a pair of return connectors 638. The electrode 502 is connected to the power output connector 636 by way of the power supply lines 504 and 506 and a power connector 540, while the return electrode 502a is connected to one of the return connectors 638 by way of the power return lines 504a and 506a and a return connector 542. In some cases, the ESU output and return connectors 636 and 638 have different shapes to avoid confusion and the power and return connectors 540 and 542 are correspondingly shaped. For example, power connector 540 may have a circular shape corresponding to an ESU power output connector 636 having a circular shape, and return connector 542 may have a rectangular shape corresponding to an ESU return connector 638 having a rectangular shape. Signals from the temperature sensors 526a/526b and 528a/528b can transmitted to the ESU 600 by way of the signal lines 530 and the power connector 540.

Figure 7:
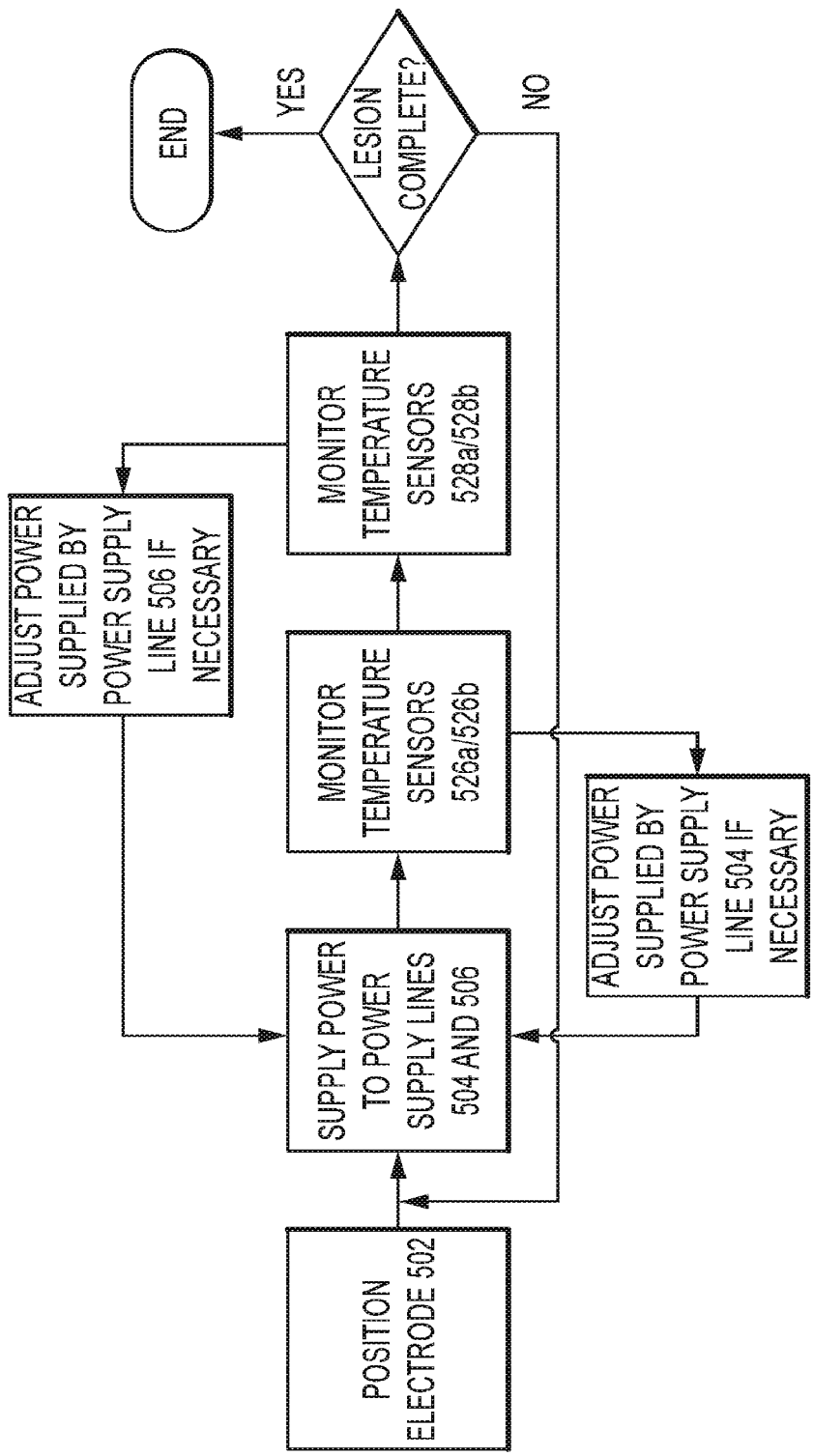
FIG. 7 illustrates aspects of treatment systems and methods according to embodiments of the present invention.

ESU 600 can be configured to individually power and control a plurality of electrodes. In some cases, the electrodes may be about 10 mm in length. Optionally, a bipolar clamp configuration may include two 32 mm active electrodes and one 70 mm electrode. Such individually powered or controlled configurations may be referred to as providing "multi-channel control." In some cases, ESU 600 can include up to 8 channels, or more. ESU 600 can also be configured to individually power and control two or more portions of a single electrode as well as two or more portions of each of a plurality of electrodes during a lesion formation procedure. Electrode 502 as shown here can be divided into two portions for power control purposes. The electrode portion connected to the power supply line 504 on one side of the dash line in FIG. 6A and the electrode portion connected to the power supply line 506 on the other side of the dash line. According to some embodiments, the dash line does not represent a physical division and the electrode 502 is a continuous, unitary structure. Electrode 502 can be placed adjacent to tissue and power to one portion can be controlled by control channel CH1 and power to the other portion is controlled by control channel CH2. The power can be, although not necessarily, supplied to both portions simultaneously. Aspects of exemplary power supply/lesion formation methods are illustrated in FIG. 7.

According to some embodiments, the level of power supplied to the electrode 502 by way of the power supply line 504 may be controlled based on the temperatures sensed by the temperature sensors 526a/526b, while the level of power supplied to the electrode 502 by way of the power supply line 506 may be controlled based on the temperatures sensed by the temperature sensors 528a/528b. In one exemplary control scheme, the level of power supplied to the electrode 502 by way of the power supply line 504 can be controlled based on the highest of the two temperatures sensed by the temperature sensors 526a/526b, while the level of power supplied to the electrode 502 by way of the power supply line 506 can be controlled based on the highest of the two temperatures sensed by the temperature sensors 528a/528b.

The amount of power required to coagulate tissue typically ranges from 5 to 150 w. Aspects of suitable temperature sensors and power control schemes that are based on sensed temperatures are disclosed in U.S. Pat. Nos. 5,456,682, 5,582,609 and 5,755,715, the contents of which are incorporated herein by reference.

The actual number and location of the temperature sensors may be varied in order to suit particular applications. As illustrated for example in FIG. 6B, the temperature sensors 528a and 528b may be located on the return electrode 502a in certain bipolar implementations. Optionally, the power control scheme can be the same in that the level of power supplied to the electrode 502 by way of the power supply line 504 can be controlled based on the temperatures sensed by the temperature sensors 526a/526b, while the level of power supplied to the electrode 502 by way of the power supply line 506 can be controlled based on the temperatures sensed the temperature sensors 528a/528b.

According to some embodiments, a plurality of spaced electrodes can be provided that operate in a unipolar mode. Each of the electrodes can be connected to a respective pair of power supply lines and include its own set of temperature sensors. Each of the electrodes on a surgical probe can be divided into portions for power control purposes, and the level of power supplied to some electrode portions by way of power supply lines can be controlled based on the temperatures sensed by certain temperature sensors, while the level of power supplied to other electrode portions by way of power supply lines can be controlled based on the temperatures sensed by certain other temperature sensors.

Articulating and Adjustable Clamp Mechanisms

Embodiments of the present invention provide multiple approaches for actuating clamp mechanism components, such that clamp jawbones can be rotated and locked into various useful angular orientations or positions. Typically, the jawbones are rigid with a fixed curve or shape, which allow a surgeon to easily adjust a treatment profile delivered by the treatment system. For example, the jawbones can be rotated to an orientation suitable for clamping across the base of a pulmonary vein (PV) or across the base of multiple pulmonary veins. The clamp mechanisms may operate to "bite" into the patient tissue. In the instance where pulmonary veins extend from the left atrium, the curve of the clamp mechanisms can be rotatably adjusted so that the outward or convex curve presented by the clamps is opposite the base curvature the pulmonary vein or atrial chamber wall. In some cases, the veins can be relatively short and straight, having no base curvature to them, and exit the atria somewhat perpendicularly to the surface of the atria. Hence, the clamp mechanisms can be used not only pinch the base of the pulmonary vein, but also to "bite" into or beyond the base of the vein, such as to clamp portions of the atrial walls together. The rotatably adjustable nature of the treatment system jawbones allows the surgeon to configure the clamping mechanism in an orientation appropriate for the direction or route in which the system is introduced to the treatment site.

Pull and Rotate Embodiments

Figure 8A:
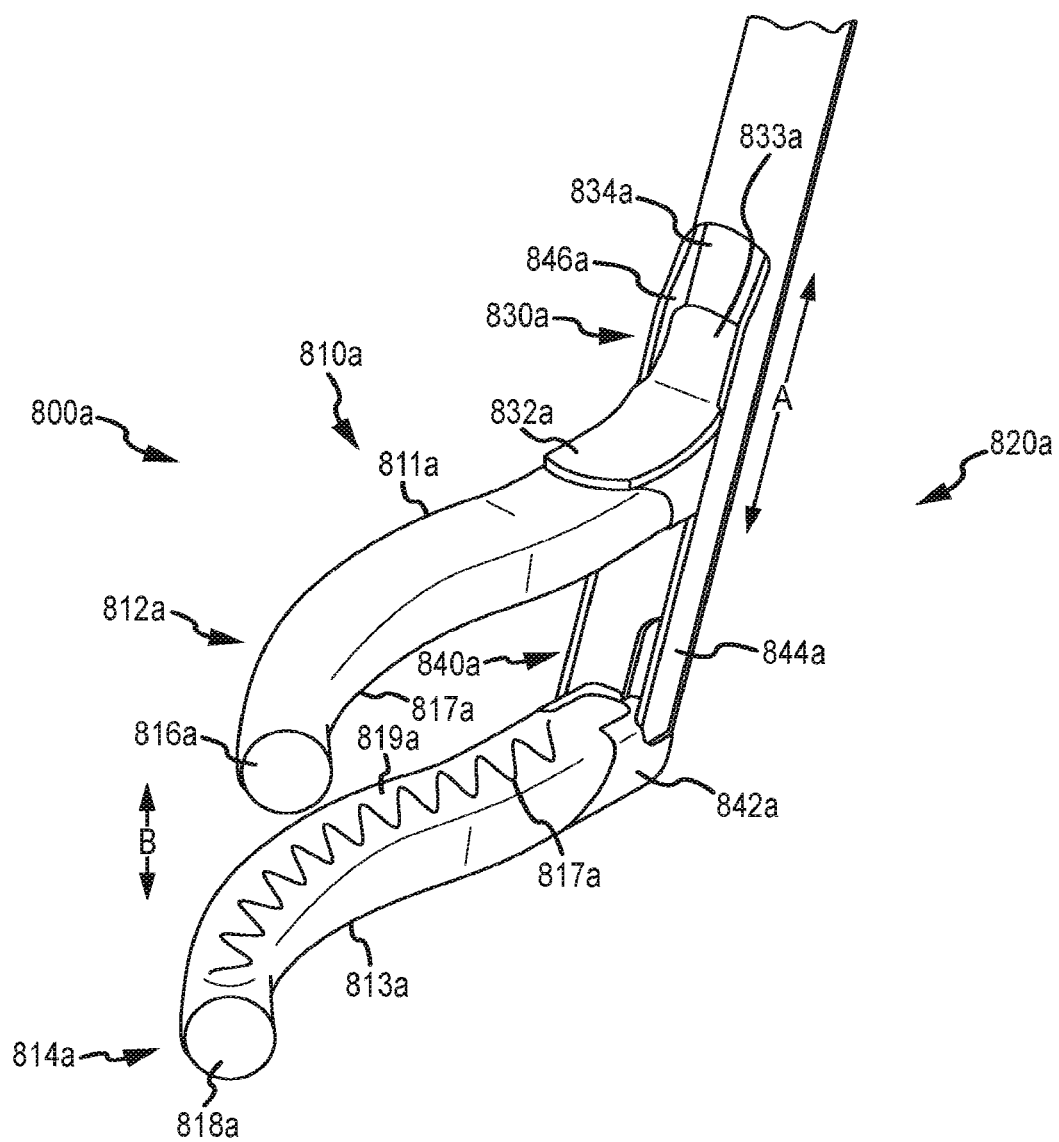
FIGS. 8A to 8O illustrate aspects of treatment systems and methods according to embodiments of the present invention.

FIG. 8A depicts aspects of an adjustable clamp system 800a according to embodiments of the present invention. As shown here, clamp system 800a includes a clamp assembly 810a coupled with or in operative association with a base assembly 820a. Clamp assembly 810a has a first jaw mechanism 812a and a second jaw mechanism 814a, and base assembly 820a has a first base mechanism 830a and a second base mechanism 840a. First jaw mechanism 812a is coupled with first base mechanism 830a, and second jaw mechanism 814a is coupled with second base mechanism 840a. In use, first and second base mechanisms 830a, 840a are translated relative to one another, as indicated by arrow A, which in turn causes first jaw mechanism 812a and second jaw mechanism 814a to move away from or toward one another, as indicated by arrow B. According to some embodiments, first base mechanism 830a may include a first base 832a coupled with a first base shaft element 834a. Relatedly, second base mechanism 840a can include a second base 842a coupled with a second base shaft element 844a. As depicted here, second base shaft element 844a includes a groove 846a that is configured to receive a tongue 833a of first base 832a. In some cases portion 832a forms a part of the jaw base. It can be a blended curved shape that gives stiffness to the jaw and an appropriate length to join the base to the shaft, for example by a laser weld. Further, each of the first and second jaw mechanisms may include a flexible boot coupled with a flexible ablation member, and optionally an end plug mechanism. For example, first jaw mechanism 812a may include a flexible boot 811a coupled with a flexible ablation member (not shown) and an end plug mechanism 816a. Relatedly, second jaw mechanism 814a may include a flexible boot 813a coupled with a flexible ablation member 817a and an end plug mechanism 818a. According to exemplary embodiments, each of the jaw mechanisms may include a jawbone mechanism (not shown) disposed at least partially within the flexible boot. Such jawbones may be configured to rotate or revolve within or relative to the respective boots 811a, 813a, for example. In some cases, the jawbones may rotate within the boots, while flexible electrode mounting surfaces 817a, 819a of boots 811a, 813a, respectively, remaining facing one another. According to some embodiments, the jawbones do not rotate around while the electrodes are in use. Typically, the boots take on the shape of the backbone within.

End plug mechanisms 816a, 818a may include any of a variety of auxiliary elements, including lights, cameras, sensors, fluid passages, nozzle features, knobs, and the like. Relatedly, end plug mechanisms 816a, 818a can be used by a physician or operator to perform various surgical techniques. For example, one or both of end plug mechanisms 816a, 818a can include a tissue plane dissector. In some cases, one or both of end plug mechanisms 816a, 818a can include an introducer tubing mount or other navigational mechanism, and hence can be used in conjunction with introducer or navigational systems, such as those described in U.S. patent application Ser. Nos. 12/124,743 and 12/124,766 filed May 21, 2008, U.S. patent application Ser. No. 12/339,331 filed Dec. 19, 2008, U.S. Provisional Patent Application No. 61/179,564 filed May 19, 2009, and U.S. Provisional Application No. 61/241,297 filed Sep. 10, 2009, the entire content of each of which is incorporated herein by reference. In some case, one or both of end plug mechanisms 816a, 818a can include a light mechanism. Optionally, one or both of end plug mechanisms 816a, 818a can include a camera or video mechanism. According to some embodiments, one or both of end plug mechanisms 816a, 818a can include a cooling water or fluid passage terminal. In some cases, one or both of end plug mechanisms 816a, 818a can include a flush, dissection, or insufflation nozzle. Optionally, one or both of end plug mechanisms 816a, 818a can include one or more sensors for multiple applications. According to some embodiments, one or both of end plug mechanisms 816a, 818a can include a manual knob for rotating an internal jawbone. In some cases, a treatment system may present a disposable dedicated bipolar clamp having flip-jaw revolving or rotary jawbones disposed at least partially within a flexible electrode boot. Embodiments also include system configurations having jaws with closed-end boots and no end plugs.

Figure 8B:
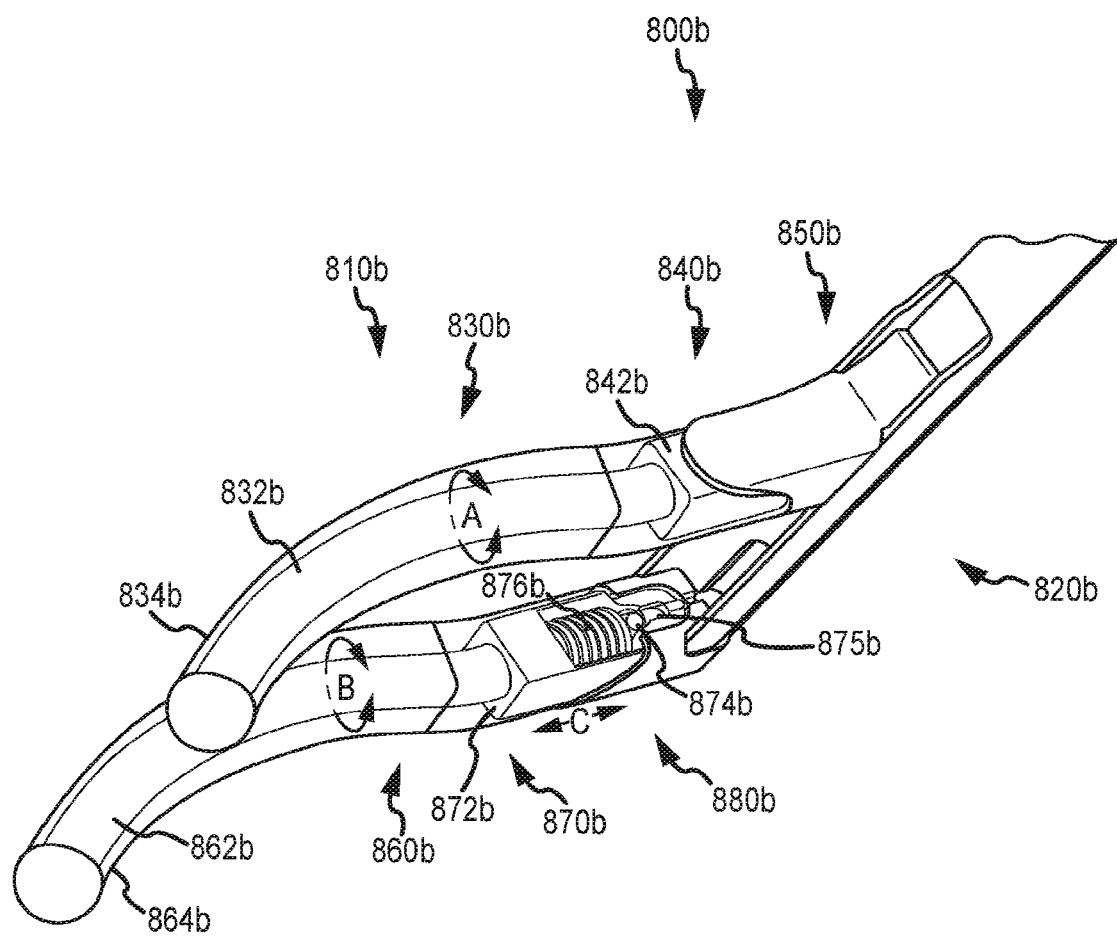

FIG. 8B depicts aspects of an adjustable clamp system 800b according to embodiments of the present invention. As shown here, clamp system 800b includes a clamp assembly 810b coupled with or in operative association with a base assembly 820b. Clamp assembly 810b has a first jaw mechanism 830b and a second jaw mechanism 860b, and base assembly 820b has a first base mechanism 850b and a second base mechanism 880b. First jaw mechanism 830b can be coupled with first base mechanism 850b via a first rotational assembly 840b and second jaw mechanism 860b can be coupled with second base mechanism 880b via a second rotational assembly 870b. In some embodiments, one or more elements of first rotational assembly 840b are part of or integral to first base mechanism 850b. In some embodiments, one or more elements of first rotational assembly 840b are part of or integral to first jaw mechanism 830b. In some embodiments, one or more elements of second rotational assembly 870b are part of or integral to second base mechanism 880b. In some embodiments, one or more elements of second rotational assembly 870b are part of or integral to second jaw mechanism 860b.

First jaw mechanism 830b includes an internal jawbone 832b that can rotate within a flexible boot 834b. Similarly, second jaw mechanism 860b includes an internal jawbone 862b that can rotate within a flexible boot 864b. The flexible boots 834b, 864b are coupled with base mechanisms 850b, 880b, respectively. Hence, each internal jawbone can rotate relative to its respective boot and base mechanism, while the boot and base mechanism remain rotationally stationary with regard to one another. However, the internal jawbones can be shaped so that the three dimensional interface configuration between the boots changes as the jawbones rotate. In the illustration provided by FIG. 8B, the flexible boots 834b, 864b are shown in a transparent view, so as to depict the relationship between internal components such as the respective jawbones 832b, 862b.

In some embodiments, the term "jawbone" may be used interchangeably with the term "guide." Relatedly, in some embodiments a jaw mechanism includes a guide that can rotate within or relative to an ablation apparatus having an ablation member or electrode. An ablation apparatus, ablation member, or electrode can be coupled with a base mechanism. The guide can rotate relative to its corresponding ablation apparatus or electrode, and can also rotate relative to its corresponding base mechanism. During such rotation of the guide, the ablation apparatus or electrode and the base mechanism can remain rotationally stationary with regard to one another. Guides can be shaped so that the three dimensional interface configuration between their respective ablation apparatuses or electrodes can change or rotate as the guides rotate. In some cases, clamp systems are configured so that the three dimensional interface configuration between ablation apparatuses or electrodes can be adjustably fixed or set at desired angles or orientations. The three dimensional interface configuration can be defined by the alignment between the ablation apparatuses or electrodes. In some cases, the ablation apparatuses or electrodes can be present in a curved parallel relationship, in that the longitudinal axes of the ablation apparatuses or electrodes do not intersect, and are aligned at a constant or fixed distance from each other along their length. During actuation, the distance between two electrodes can decrease as the clamp system is clamped and increase as the clamp system is unclamped.

First rotational assembly 840b allows internal jawbone 832b to adjustably rotate relative to base mechanism 850b and boot 834b. For example, first rotational assembly 840b may include a jawbone collar 842b within which jawbone 832b may adjustably revolve, as indicated by arrow A. Similarly, second rotational assembly 870b may include a jawbone collar 872b within which jawbone 862b may adjustably revolve, as indicated by arrow B. As shown here, second jawbone 862b may include or be coupled with a pin 874b of second rotational assembly 870b that translates along and within a slot 875b of collar 872b or base mechanism 880b as indicated by arrow C, thus causing compression or allowing decompression of a compressible member 876a of rotational assembly 870b. Compressible member 876a may include a spring, an elastomeric material, or any other suitable compressible element. The jawbones can be constructed of a rigid material, and as such, the jawbone shape can provide a guiding support or skeletal framework for the shape of the flexible boots.

Figure 8C:
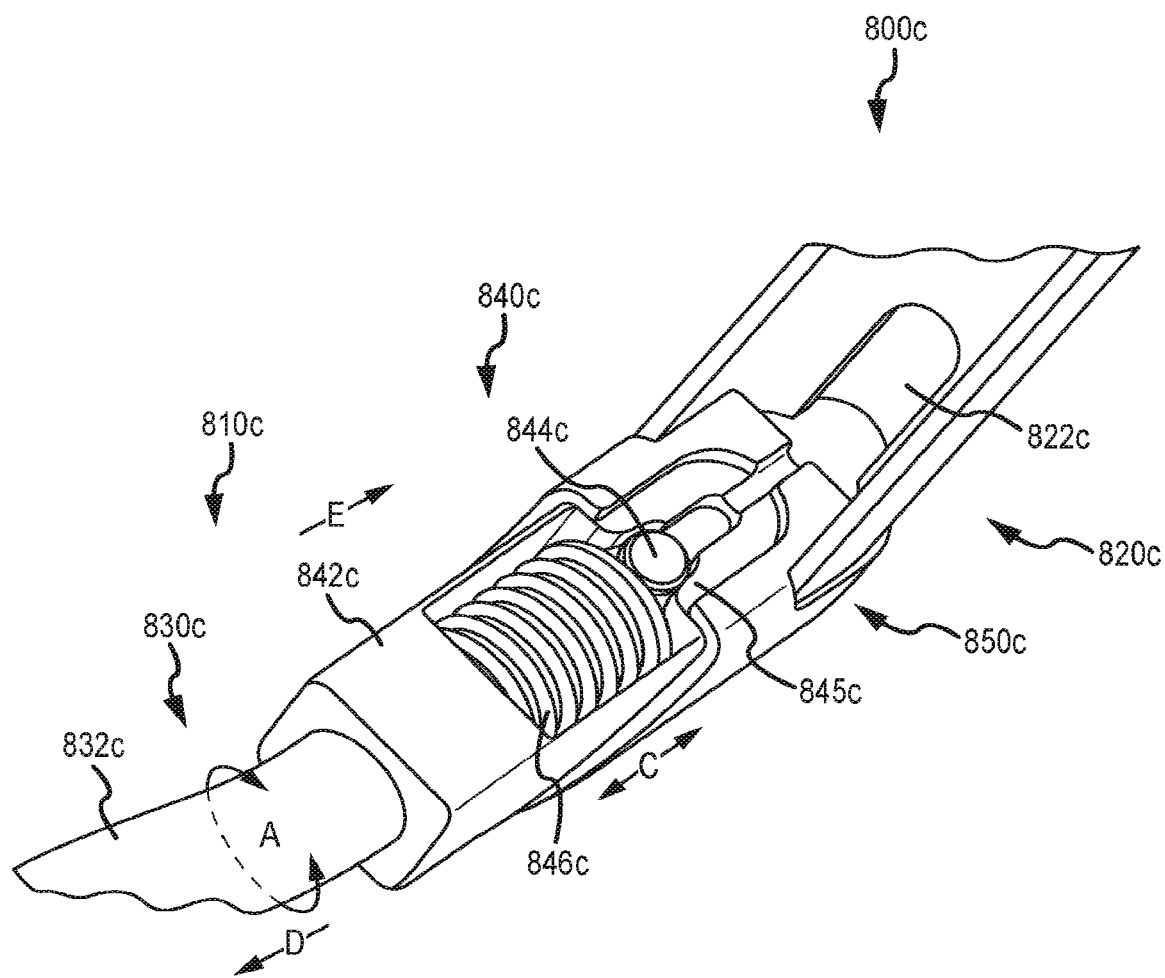

FIG. 8C depicts aspects of an adjustable clamp system 800c according to embodiments of the present invention. As shown here, clamp system 800c includes a clamp assembly 810c coupled with or in operative association with a base assembly 820c. Clamp assembly 810c has a first jaw mechanism 830c, and base assembly 820c has a first base mechanism 850c. First jaw mechanism 830c can be adjustably coupled with first base mechanism 850c, optionally via a first rotational assembly 840c. In some embodiments, one or more elements of first rotational assembly 840c are part of or integral to first base mechanism 850c. In some embodiments, one or more elements of first rotational assembly 840c are part of or integral to first jaw mechanism 830c. First jaw mechanism 830c includes an internal jawbone 832c that can rotate within a flexible boot (not shown). The flexible boot can be coupled with base mechanism 850c. Hence, internal jawbone 832c can rotate relative to base mechanism 850c, while the boot and base mechanism remain rotationally stationary with regard to one another.

First rotational assembly 840c, or optionally base mechanism 850c, allows internal jawbone 832c to adjustably rotate relative to base mechanism 850c and a boot (not shown). For example, first rotational assembly 840c or base mechanism 850c may include a jawbone collar 842c within which jawbone 832c may adjustably revolve, as indicated by arrow A. As shown here, first jawbone 832c may include or be coupled with a pin 844c of first rotational assembly 840c that translates along or sets within a slot or pocket 845c of collar 842c or base mechanism 850c as indicated by arrow C, thus causing compression or allowing decompression of a compressible member 846c, which may be a part of jawbone 832c, rotational assembly 840c, or base mechanism 850c.

A compressible member may include a spring, an elastomeric material, or any other suitable compressible element or combination of elements. In some cases, a compressible member or assembly includes one or more rebounding members such as springs, elastomers, elasticized members, and the like. A spring can be defined as a flexible elastic object which can store potential or mechanical energy. Exemplary springs include coil springs, helical springs, conical springs, torsion springs, volute springs, gas springs, and the like. Typically, a compression spring becomes shorter when subjected to a load. In some cases, a compressible member can include an elastomeric or rubber material. An elastomer can refer to a polymer which resists and recovers from deformation which is produced by a force applied to the polymer. Typically, an elastomer becomes shorter or compressed when subjected to a load. An elastomer may return to its original dimensions after being deformed under an application of mechanical force. In some cases, the terms "elastomer" and "rubber" are used interchangeably, and can refer to natural or synthetic materials, or combinations thereof. An elastomer can be a flexible elastic object which can store potential or mechanical energy. Different elastomers may have different durometers or compressibilities. For example, a first elastomer may have a lower durometer, or a higher compressibility, than a second elastomer. Often, a durometer value or rating is inversely related to a compressibility value or rating. A durometer rating can be a measure of the resistance a material exhibits to deformation. For example, a material having a high durometer, or a low compressibility, may exhibit a greater resistance to deformation when subjected to a load or stress. An elastomer can have a linear compressibility, where the compressibility is constant or substantially constant regardless of the load applied to the elastomer. An elastomer may also have a progressive compressibility, where the compressibility of the elastomer changes as an increasing load is applied to the elastomer.

In use, an operator may adjust the rotational position of internal jawbone 832c by pulling or moving jawbone 832c in a distal direction, as indicated by arrow D, thus compressing the compressible member 846c and drawing pin 844c out or away from pocket 845c. Once the pin is sufficiently withdrawn from the pocket, the operator can rotate jawbone 832c as indicated by arrow A. Base mechanism 850c or rotational assembly 840c may include a plurality of pockets into which pin 844c may fit. Hence, for example, when the operator has rotated jawbone 832c to the desired rotational configuration, the operator may release or reduce the pulling or moving force applied to jawbone 832c, thus allowing compressible member 846c to decompress as pin 844c moves proximally into the appropriate pocket in a direction illustrated by arrow E. Compressible member 846c can therefore operate to urge the pin, and consequently the jawbone, in a proximal direction. When pin 844c is disposed within the pocket, compressible member 846c can operate to prevent or inhibit jawbone 832c from moving in a distal direction. In this way, pin 844c remains in the pocket, thus restraining further rotational movement of jawbone 832c. Hence, the operator can securely, and releasably, fix the jawbone in an orientation that is optimal for treating a desires anatomical shape or feature. As shown here, base assembly 820c includes a mousehole 822c through which energy transmission wires, temperature sensor wires, fluid conduits, and the like, can be routed to and from the jaw mechanism. For example, an active electrode on a clamp may be attached with an RF wire and four thermocouple wires (e.g. two thermocouple pairs each having two thermocouple wires), an indifferent electrode may be attached with a return wire. In this case, any or all of the six wires can be routed through the mousehole.

Figure 8D:
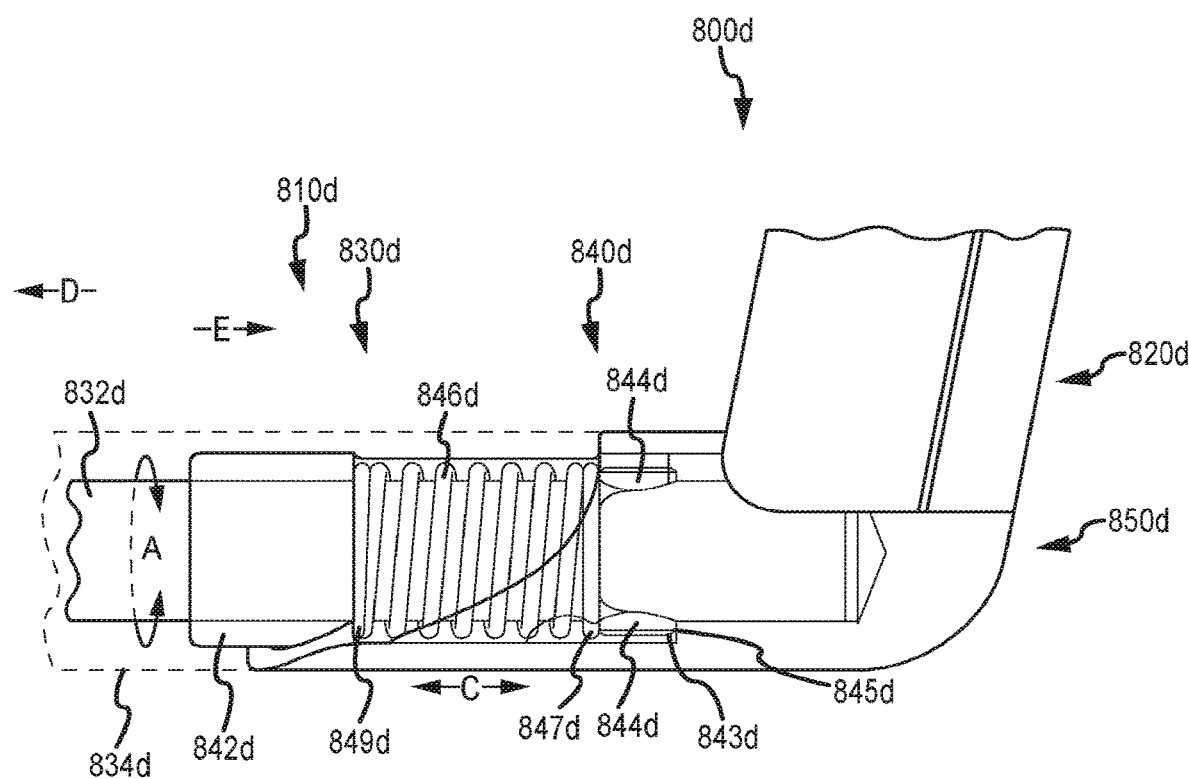

FIG. 8D depicts aspects of an adjustable clamp system 800d according to embodiments of the present invention. As shown here, clamp system 800d includes a clamp assembly 810d coupled with or in operative association with a base assembly 820d. Clamp assembly 810d has a first jaw mechanism 830d, and base assembly 820d has a first base mechanism 850d. First jaw mechanism 830d can be adjustably coupled with first base mechanism 850d, optionally via a first rotational assembly 840d. In some embodiments, one or more elements of first rotational assembly 840d are part of or integral to first base mechanism 850d. In some embodiments, one or more elements of first rotational assembly 840d are part of or integral to first jaw mechanism 830d. First jaw mechanism 830d includes an internal jawbone 832d that can rotate within a flexible boot 834d. The flexible boot can be coupled with base mechanism 850d or rotational assembly 840d, or both. Hence, internal jawbone 832d can rotate relative to base mechanism 850d, while boot 834d and base mechanism 850d remain rotationally stationary with regard to one another.

Base mechanism 850d, optionally in combination with first rotational assembly 840d, allows internal jawbone 832d to adjustably rotate relative to base mechanism 850d and boot 834d. For example, first rotational assembly 840d or base mechanism 850d may include a jawbone collar 842d within which jawbone 832d may adjustably revolve, as indicated by arrow A. As shown here, first jawbone 832d may include or be coupled with a pin 844d that translates along or sets within a stop or pocket 843d of collar of base assembly 820d as indicated by arrow C, thus causing compression or allowing decompression of a compressible member 846d, which may be a part of jawbone 832d, rotational assembly 840d, or base mechanism 850d.

In use, an operator may adjust the rotational position of internal jawbone 832d by pulling or moving jawbone 832d in a distal direction, as indicated by arrow D, thus compressing the compressible member 846d and moving pin 844d away from stop 845d. Such action causes a proximal portion 847d of the compressible member to move toward a distal portion 849d of the compressible member. Once the pin is moved to predetermined distance away from the stop, the operator can rotate jawbone 832d as indicated by arrow A. Base assembly 820d or rotational assembly 840d may include a plurality of stops or pockets into which pin 844d may fit. Hence, for example, when the operator has rotated jawbone 832*d* to the desired rotational configuration, the operator may release or reduce the pulling or moving force applied to jawbone 832*d*, thus allowing compressible member 846*d* to decompress as pin 844*d* moves proximally into the appropriate pocket in a direction as indicated by arrow E. When pin 844*d* is disposed within the pocket, compressible member 846*d* can operate to prevent or inhibit jawbone 832*d* from moving in a distal direction. In this way, pin 844*d* remains in the pocket, thus restraining further rotational movement of jawbone 832*d*.

Figure 8E:
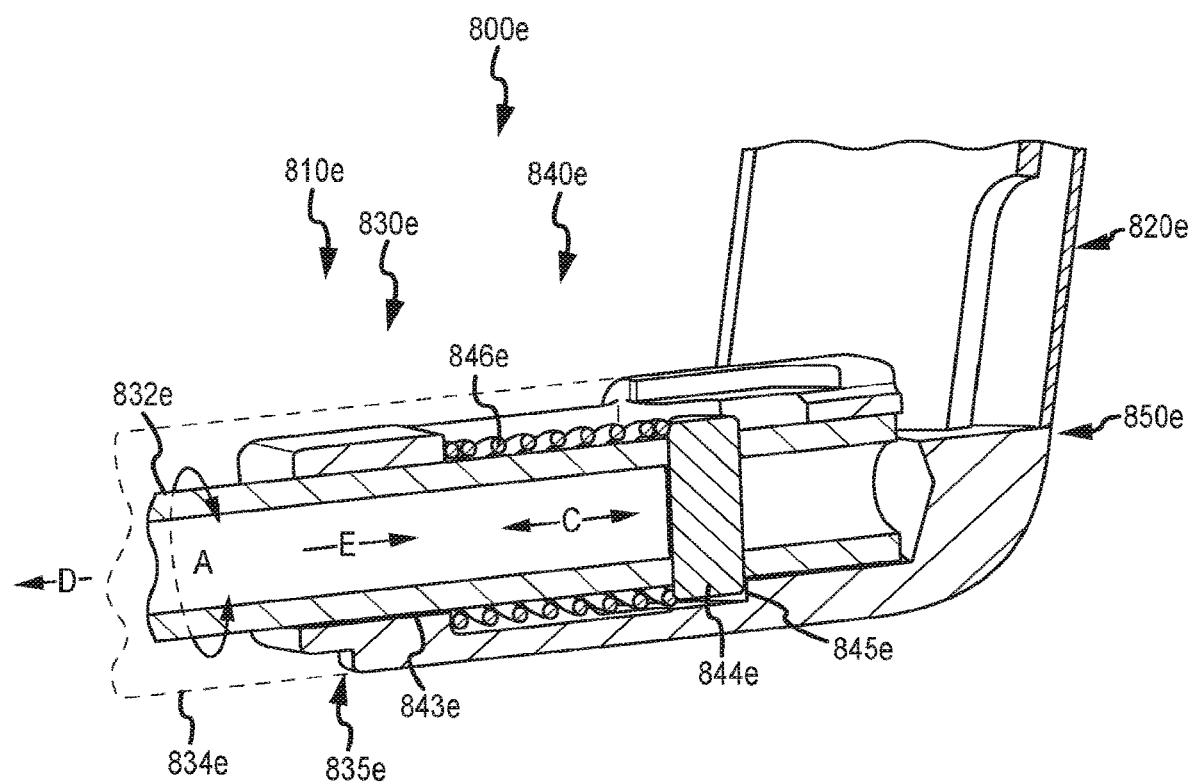

FIG. 8E depicts aspects of an adjustable clamp system 800*e* according to embodiments of the present invention. As shown here, clamp system 800*e* includes a clamp assembly 810*e* coupled with or in operative association with a base assembly 820*e*. Clamp assembly 810*e* has a first jaw mechanism 830*e*, and base assembly 820*e* has a first base mechanism 850*e*. First jaw mechanism 830*e* can be adjustably coupled with first base mechanism 850*e*, optionally via a first rotational assembly 840*e*. In some embodiments, one or more elements of first rotational assembly 840*e* are part of or integral to first base mechanism 850*e*. In some embodiments, one or more elements of first rotational assembly 840*e* are part of or integral to first jaw mechanism 830*e*. First jaw mechanism 830*e* includes an internal jawbone 832*e* that can rotate within a flexible boot 834*e*. The flexible boot can be coupled with base mechanism 850*e* or rotational assembly 840*e*, or both. Hence, internal jawbone 832*e* can rotate relative to base mechanism 850*e*, while boot 834*e* and base mechanism 850*e* remain rotationally stationary with regard to one another. Optionally, boot 834*e* and base mechanism 850*e* may be coupled via one or more attachment points or locations 835*e*. For example, the boot may be glued or fixed to the base mechanism via an adhesive or other attachment mechanism.

First rotational assembly 840*e*, optionally in combination with base mechanism 850*e* or base assembly 820*e*, allows internal jawbone 832*e* to adjustably rotate relative to base mechanism 850*e* or base assembly 820*e* and boot 834*e*. For example, first rotational assembly 840*e* or base mechanism 850*e*, or a combination thereof, may provide a jawbone channel 843*e* within which jawbone 832*e* may adjustably revolve, as indicated by arrow A. As shown here, first jawbone 832*e* may include or be coupled with a pin 844*e* that translates along or sets within a stop or pocket 845*e* of channel 843*e* as indicated by arrow C, thus causing compression or allowing decompression of a compressible member 846*e*, which may be a part of jawbone 832*e*, rotational assembly 840*e*, or base mechanism 850*e*.

In use, an operator may adjust the rotational position of internal jawbone 832*e* by pulling or moving jawbone 832*e* in a distal direction, as indicated by arrow D, thus compressing the compressible member 846*e* between stop 852*e* and pin 844*e*, where stop 852*e* is fixed relative to base mechanism 850*e*. This compression or pulling action operates to move pin 844*e* away from stop 845*e*, which may also be fixed relative to base mechanism 850*e*. As shown here, the pin remains stationary relative to the body of the jawbone. Once the pin is moved to a predetermined distance away from the stop 845*e*, such that the jawbone is translated along its long axis as indicated by arrow D, the operator can rotate jawbone 832*e* as indicated by arrow A. Base mechanism 850*e* or rotational assembly 840*e* may include a plurality of stops or pockets into which pin 844*e* may fit. Hence, for example, when the operator has rotated jawbone 832*e* to the desired rotational configuration, the operator may release or reduce the pulling or moving force applied to jawbone 832*e*, thus allowing compressible member 846*e* to decompress as pin 844*e* moves proximally as indicated by arrow E into the appropriate pocket. For example a compressible member or spring can operate to force the pin into or toward the pocket. When pin 844*e* is disposed within the pocket, compressible member 846*e* can operate to prevent or inhibit jawbone 832*e* from moving in a distal direction. In this way, pin 844*e* remains in the pocket, thus restraining further rotational movement of jawbone 832*e*. Hence, the pin and pocket can be part of an anti-rotational feature or assembly that counters rotational moments when clamping forces are applied to the clamp mechanism.

Figure 8F:
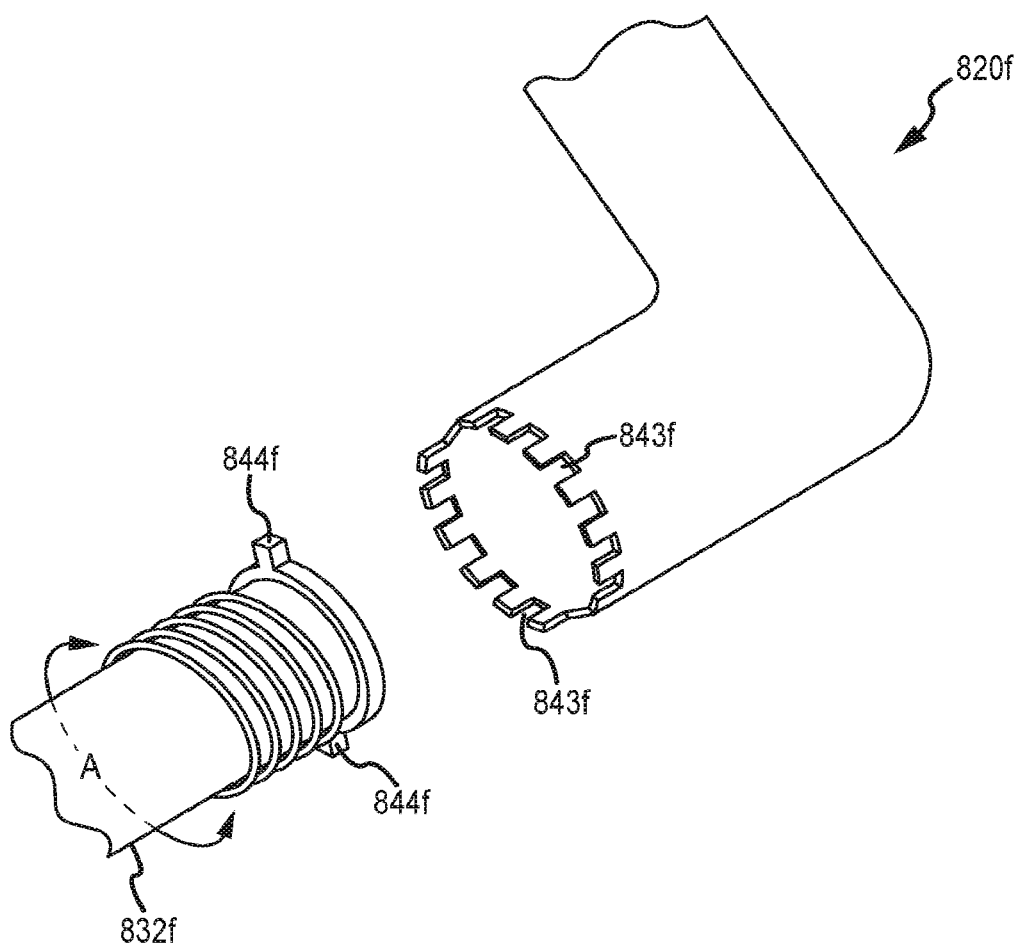

FIG. 8F illustrates aspects of a treatment system 800*f* according to embodiments of the present invention. As shown here, a jawbone member 832*f* can adjustably rotate relative to a base assembly 820*f* as indicated by arrow A. Jawbone member 832*f* includes one or more pins or protrusions 844*f*, and the base assembly includes one or more pockets or stops 843*f* that are configured to receive a jawbone pin. When pin 844*f* is disengaged from stop 843*f*, the jawbone can rotate relative to the base assembly as indicated by arrow A. When pin 844*f* is engaged with or secured by stop 843*f*, the jawbone is prevented or inhibited from rotating relative to the base assembly.

Figure 8G:
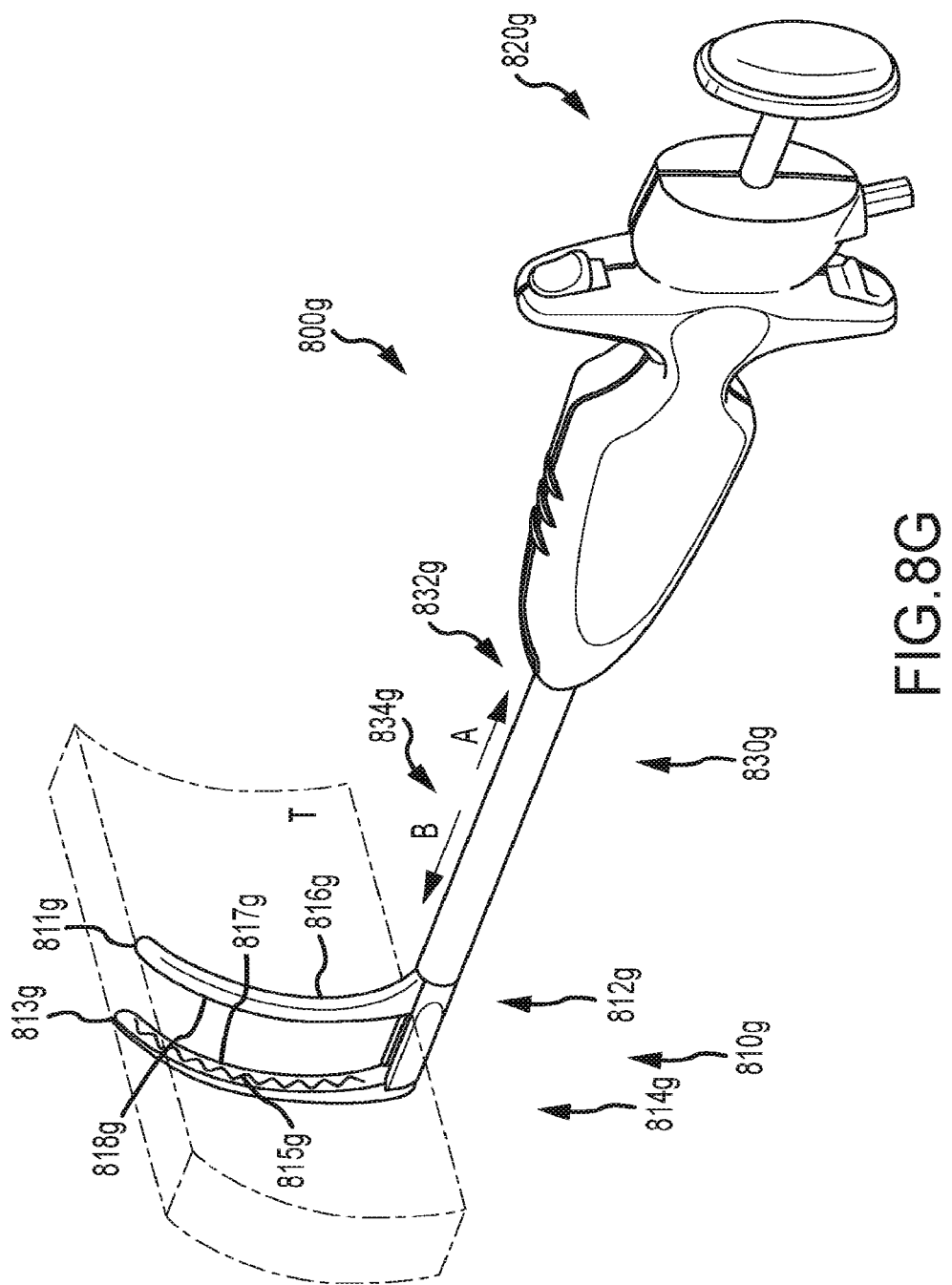

FIG. 8G illustrates aspects of a treatment system 800*g* according to embodiments of the present invention. Treatment system 800*g* includes a clamp assembly 810*g*, an actuator assembly 820*g*, and a coupling assembly 830*g* in operative association with both the clamp assembly and the actuator assembly. Clamp assembly 810*g* includes a first jaw mechanism 812*g* and a second jaw mechanism 814*g*. Coupling assembly 830*g* may include a shaft or other elongate member that allows the physician or operator to access or reach a surgical site with the clamp assembly, when the physician is holding actuator assembly 820*g*. Coupling assembly 830*g* includes a proximal end 832*g* and a distal end 834*g*. As shown here, clamp assembly 810*g* is coupled with distal end 834*g* of coupling assembly 830*g*, and actuator assembly 820*g* is coupled with proximal end 832*g* of coupling assembly 830*g*. Clamp assembly 810*g* is depicted in a generally open configuration, such that first jaw mechanism 812*g* does not contact or is situated at a distance from second jaw mechanism 814*g*. The treatment system includes a serpentine electrode or ablation member 815*g* disposed on second jaw mechanism 814*g*. The first jaw mechanism 812*g* includes a corresponding electrode or ablation member (not shown) that faces toward ablation member 815*g*. In use, when the jaw mechanisms are clamped together, the respective ablation members of the first and second jaw mechanisms contact the surface of the tissue T. First jaw mechanism 812*g* includes a distal tip 811*g*, and second jaw mechanism includes a distal tip 813*g*. FIG. 8G illustrates aspects of a treatment system that is configured in an "up curve" orientation. That is, when the actuator handle 820*g* is held by the surgeon, with the device shaft 830*g* extending horizontally away from the surgeon's body and the jawbone tips 811*g*, 813*g* pointed in an upward direction, the clamp mechanisms 812*g*, 814*g* are curved or arced toward the handle 820*g* or operator, such that concave or inner faces or portions 816*g*, 817*g*, respectively, of the jawbones or jaw mechanisms 812*g*, 814*g* face toward the handle or operator in the direction indicated by arrow A, and convex or outer faces or portions 818*g*, 819*g*, respectively, of the jawbones or jaw mechanisms 812*g*, 814*g* face away from the handle or operator in the direction indicated by arrow B. In some cases, the term inner faces refers to the surfaces that face each other where the electrodes are mounted. The device can also present an inner or inside space between the jaws, which can be defined by an inside measurement between the jaws.

FIG. 8H illustrates aspects of a treatment system 800h according to embodiments of the present invention. Treatment system 800h includes a clamp assembly 810h, an actuator assembly 820h, and a coupling assembly 830h in operative association with both the clamp assembly and the actuator assembly. Clamp assembly 810h includes a first jaw mechanism 812h and a second jaw mechanism 814h. Coupling assembly 830h may include a shaft or other elongate member that allows the physician or operator to access or reach a surgical site with the clamp assembly, when the physician is holding actuator assembly 820h. Coupling assembly 830h includes a proximal end 832h and a distal end 834h. As shown here, clamp assembly 810h is coupled with distal end 834h of coupling assembly 830h, and actuator assembly 820h is coupled with proximal end 832h of coupling assembly 830h. Clamp assembly 810h is depicted in a generally open configuration, such that first jaw mechanism 812h does not contact or is situated at a distance from second jaw mechanism 814h. The treatment system includes a serpentine electrode or ablation member 815h disposed on second jaw mechanism 814h. The first jaw mechanism 812h includes a corresponding electrode or ablation member (not shown) that faces toward ablation member 815h. In use, when the jaw mechanisms are clamped together, the respective ablation members of the first and second jaw mechanisms contact the surface of the tissue T. First jaw mechanism 812h includes a distal tip 811h, and second jaw mechanism includes a distal tip 813h. FIG. 8H illustrates aspects of a treatment system that is configured in an "down curve" orientation. That is, when the actuator handle 820h is held by the surgeon, with the device shaft 830h extending horizontally away from the surgeon's body and the jawbone tips 811h, 813h pointed in an upward direction, the clamp mechanisms 812h, 814h are curved or arced away from the handle 820h or operator, such that such that concave or inner faces or portions 816h, 817h, respectively, of the jawbones or jaw mechanisms 812h, 814h face away from the handle 820h or operator in the direction indicated by arrow A, and convex or outer faces or portions 818h, 819h, respectively, of the jawbones or jaw mechanisms 812h, 814h face toward the handle 820h or operator in the direction indicated by arrow B.

Figure 8I:
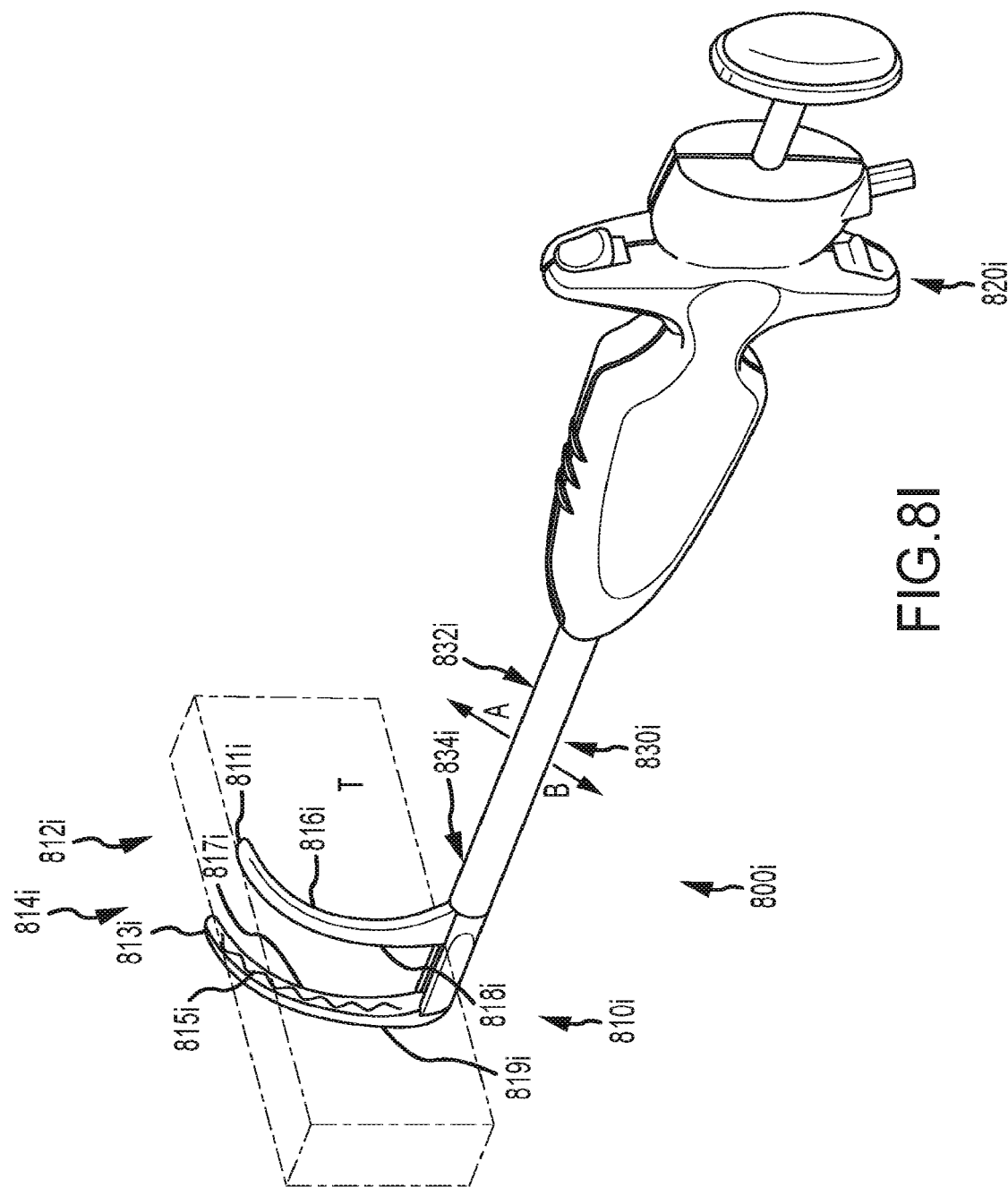

FIG. 8I illustrates aspects of a treatment system 800i according to embodiments of the present invention. Treatment system 800i includes a clamp assembly 810i, an actuator assembly 820i, and a coupling assembly 830i in operative association with both the clamp assembly and the actuator assembly. Clamp assembly 810i includes a first jaw mechanism 812i and a second jaw mechanism 814i. Coupling assembly 830i may include a shaft or other elongate member that allows the physician or operator to access or reach a surgical site with the clamp assembly, when the physician is holding actuator assembly 820i. Coupling assembly 830i includes a proximal end 832i and a distal end 834i. As shown here, clamp assembly 810i is coupled with distal end 834i of coupling assembly 830i, and actuator assembly 820i is coupled with proximal end 832i of coupling assembly 830i. Clamp assembly 810i is depicted in a generally open configuration, such that first jaw mechanism 812i does not contact or is situated at a distance from second jaw mechanism 814i. The treatment system includes a serpentine electrode or ablation member 815i disposed on second jaw mechanism 814i. The first jaw mechanism 812i includes a corresponding electrode or ablation member (not shown) that faces toward ablation member 815i. In use, when the jaw mechanisms are clamped together, the respective ablation members of the first and second jaw mechanisms contact the surface of the tissue T. First jaw mechanism 812i includes a distal tip 811i, and second jaw mechanism includes a distal tip 813i. FIG. 8I illustrates aspects of a treatment system that is configured in a "right curve" orientation. That is, when the actuator handle 820i is held by the surgeon, with the device shaft 830i extending horizontally away from the surgeon's body and the jawbone tips 811i, 813i pointed in an upward direction, the clamp mechanisms 812i, 814i are curved or arced toward the right, such that concave or inner faces or portions 816i, 817i, respectively, of the jawbones or jaw mechanisms 812i, 814i face toward the right in the direction indicated by arrow A, and convex or outer faces 818i, 819i, respectively, of the jawbones or jaw mechanisms 812i, 814i face toward the left in the direction indicated by arrow B.

Figure 8J:
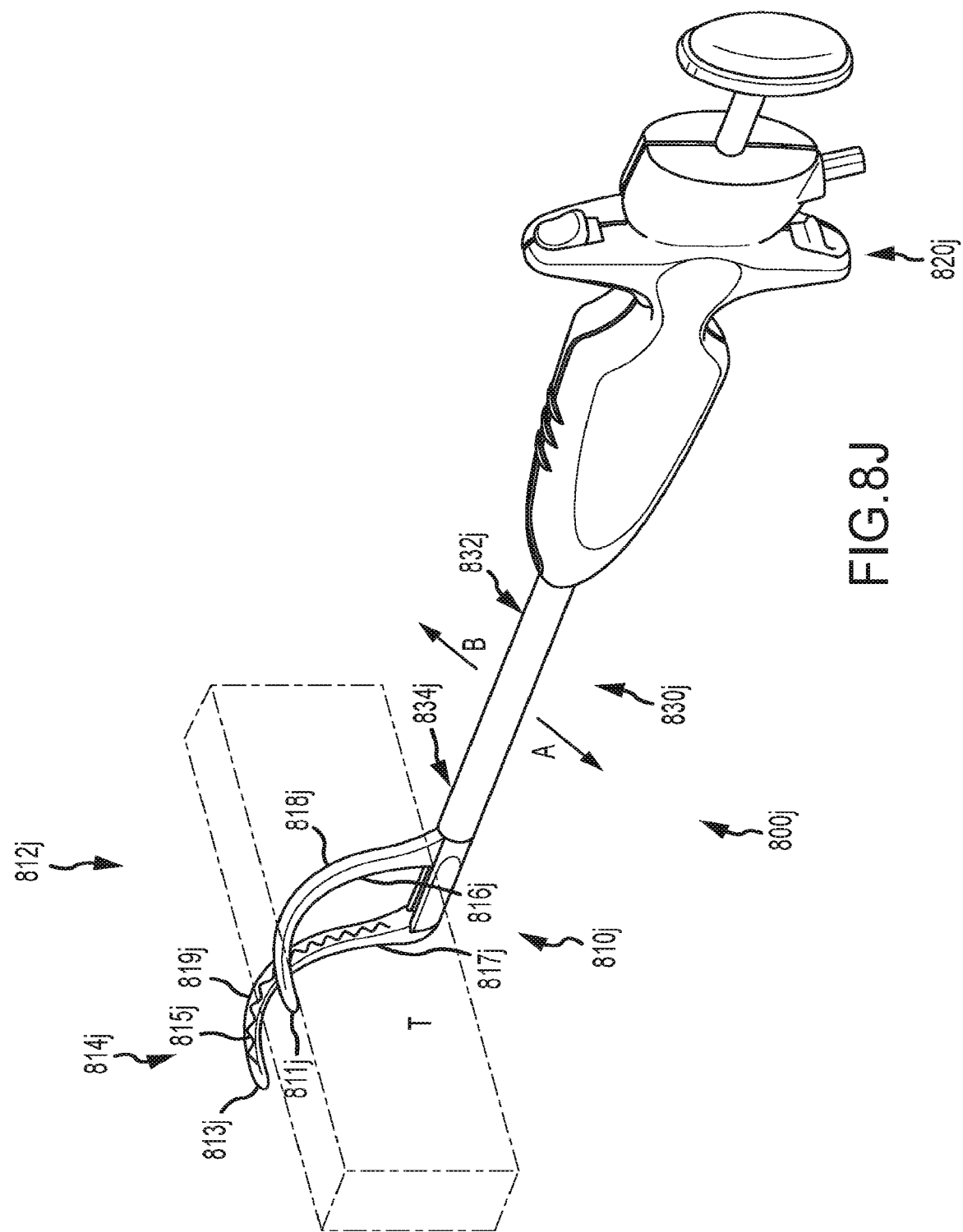

FIG. 8J illustrates aspects of a treatment system 800j according to embodiments of the present invention. Treatment system 800j includes a clamp assembly 810j, an actuator assembly 820j, and a coupling assembly 830j in operative association with both the clamp assembly and the actuator assembly. Clamp assembly 810j includes a first jaw mechanism 812j and a second jaw mechanism 814j. Coupling assembly 830j may include a shaft or other elongate member that allows the physician or operator to access or reach a surgical site with the clamp assembly, when the physician is holding actuator assembly 820j. Coupling assembly 830j includes a proximal end 832j and a distal end 834j. As shown here, clamp assembly 810j is coupled with distal end 834j of coupling assembly 830j, and actuator assembly 820j is coupled with proximal end 832j of coupling assembly 830j. Clamp assembly 810j is depicted in a generally open configuration, such that first jaw mechanism 812j does not contact or is situated at a distance from second jaw mechanism 814j. The treatment system includes a serpentine electrode or ablation member 815j disposed on second jaw mechanism 814j. The first jaw mechanism 812j includes a corresponding electrode or ablation member (not shown) that faces toward ablation member 815j. In use, when the jaw mechanisms are clamped together, the respective ablation members of the first and second jaw mechanisms contact the surface of the tissue T. First jaw mechanism 812j includes a distal tip 811j, and second jaw mechanism includes a distal tip 813j. FIG. 8J illustrates aspects of a treatment system that is configured in a "left curve" orientation. That is, when the actuator handle 820j is held by the surgeon, with the device shaft 830j extending horizontally away from the surgeon's body and the jawbone tips 811j, 813j pointed in an upward direction, the clamp mechanisms 812j, 814j are curved or arced toward the left, such that concave or inner faces or portions 816j, 817j, respectively, of the jawbones or jaw mechanisms 812j, 814j face toward the left in the direction indicated by arrow A, and convex or outer faces 818j, 819j, respectively, of the jawbones or jaw mechanisms 8126j, 814j face toward the right in the direction indicated by arrow B.

As illustrated by FIGS. 8G-8J, a single treatment system can be used to deliver an ablation treatment at a variety of treatment planes or configurations in three dimensions. As the jawbones are rotatably adjusted throughout their range of motion, the corresponding line or zone of ablation that is created or defined between the clamp electrodes is rotated as well. Thus, for example, during the course of a medical treatment a surgeon can use the system to deliver a "right curve" ablation, change the orientation of the jawbones, and then use the same system to deliver a "left curve" ablation, or an "up curve" or "down curve" ablation.

Figure 8K:
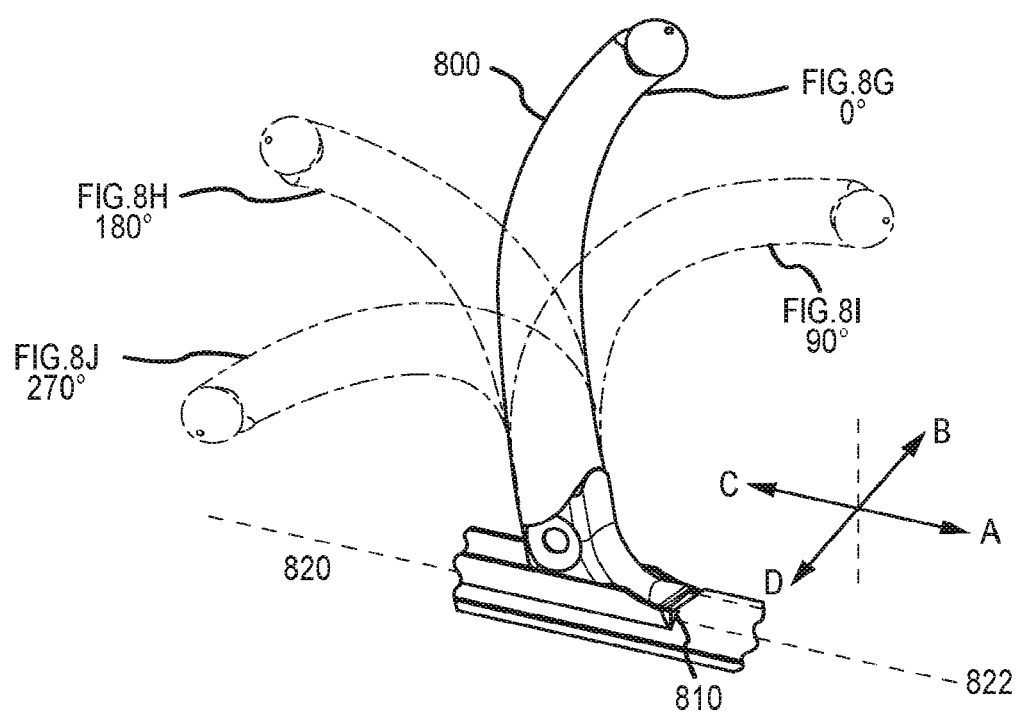

As shown in FIG. 8K, a jawbone 800 can be rotated or flipped about its long axis, to a predetermined angular orientation (e.g. 0°, 90°, 180°, or 270°. As the jawbone rotates throughout the angular range, the shape of the boot and electrode may flex and conform with the underlying configuration of the jawbone, however the angular orientation of the boot and electrode is unchanged. In this way, opposing electrodes on separate jaw mechanisms remain facing toward one another, suitable for administering treatment to a tissue that may be clamped therebetween. As shown here, the 0° position corresponds to the configuration where the concave side of the jawbone faces toward the handle, as indicated by arrow A. Relatedly, the 90° position corresponds to the configuration where the concave side of the jawbone faces toward the right, relative to the longitudinal axis 820 of the shaft 810 as viewed from a proximal portion 822 of longitudinal axis 820, as indicated by arrow B. The 180° position corresponds to the configuration where the concave side of the jawbone faces away from the handle, as indicated by arrow C. Further, the 270° position corresponds to the configuration where the concave side of the jawbone faces toward the left, relative to the longitudinal axis 820 of the shaft 810 as viewed from a proximal portion 822 of longitudinal axis 820, as indicated by arrow D.

Typically, the jawbones are rigid with a fixed curve or shape. Such rotatable curved jawbones allow the surgeon or operator to easily adjust the treatment profile of the ablation system. In some cases, the surgeon can adjust the rotation of the jawbones to a desired orientation for treating the left atrium, which presents a hemispherical shape. Optionally, the jawbones can be rotated to an orientation suitable for clamping across the base of a pulmonary vein (PV) or across the base of multiple pulmonary veins. In some cases, the clamp mechanisms operate to "bite" into the patient tissue, for example into the left atrial tissue, without completely wrapping around or encircling the tissue or anatomical feature. In the instance where four pulmonary veins extend from the left atrium, the curve of the clamp mechanisms can be rotatably adjusted so that the curve presented by the clamps is opposite the atria or the base curvature of one or more pulmonary veins. Hence, the clamp mechanisms can be actuated by the surgeon to not only pinch the base of the pulmonary veins, but also to "bite" into the base, such that the clamp mechanisms operate to clamp portions of the atrial walls together, instead of or in addition to clamping portions of the valves or veins together. In some cases, a surgeon or operator may find it is easier or more convenient to approach a treatment site from a particular direction. For example, the surgeon may desire to approach a tissue treatment site from above the site, from below the site, or from the right, left, front, or back of the site, and the like. The rotatably adjustable nature of the treatment system jawbones allows the surgeon to configure the clamping mechanism in an orientation appropriate for the tissue shape as well as for the direction or approach in which the system is introduced to the treatment site. Moreover, the same system can be adjusted in various orientations according to the particular site treated or the approach taken by the surgeon. Embodiments of the present invention are well suited for use in creating an endocardial/epicardial ablation during a stopped-heart procedure. For example, the procedure can be performed with a curved position of one jaw inside and the other outside the atrial wall.

In this way, the treatment system can be configured for delivering a shaped ablation to a right pulmonary vein or a left pulmonary vein. In some cases, the jaw mechanisms can be oriented for delivering a connecting lesion to tissue of an organ or appendage. By rotating the jawbones to the desired angular position the surgeon is enabled to clamp tissue, and deliver treatment having a stable or persistent curved ablation profile, due to the structural rigidity of the jaw mechanisms. Relatedly, the operator can administer a significant amount of clamping force to the jaw mechanisms, without causing the jawbones to flex. The rigid jawbones maintain their alignment or orientation relative to one another when subjected to high clamping forces, thus ensuring an effective and efficient ablation produced by electrodes disposed on the jaw mechanisms. In this way, the rigid jawbones, optionally in combination with the anti-rotational features, can help the system to resist or inhibit rotational moments that may be introduced when clamping forces are applied.

As the jawbone rotates or flips about its long axis, the jawbone deforms or alters the shape of the boot within which the jawbone is disposed. For example, as the jawbone is turned or revolved about its long axis throughout the various angular orientation (0°, 90°, 180°, and 270° shown in FIG. 8K, the corresponding boot can flex or assume various corresponding shapes as illustrated in FIGS. 8L-8O. Hence, as the jawbone rotates throughout the angular range, the shape of the boot and electrode may flex and conform with the underlying configuration of the jawbone, whereas the angular orientation of the boot and electrode is unchanged.

For example, when the jawbone is in the 0° configuration shown in FIG. 8K, the boot adopts the shape or configuration shown in FIG. 8L, where the tip or distal portion 810*l* of the boot 800*l* is disposed along the x-axis toward the A direction (e.g. 0° position), and the ablation member or electrode 820*l* faces toward the A direction. When the jawbone is in the 90° configuration shown in FIG. 8K, the boot adopts the shape or configuration shown in FIG. 8M, where the tip or distal portion 810*m* of the boot 800*m* is disposed along the y-axis toward the B direction (e.g. 90° position), and the ablation member or electrode 820*m* faces toward the A direction. When the jawbone is in the 180° configuration shown in FIG. 8K, the boot adopts the shape or configuration shown in FIG. 8N, where the tip or distal portion 810*n* of the boot 800*n* is disposed along the x-axis toward the C direction (e.g. 180° position), and the ablation member or electrode 820*n* faces toward the A direction. When the jawbone is in the 270° configuration shown in FIG. 8K, the boot adopts the shape or configuration shown in FIG. 8O, where the tip or distal portion 810*o* of the boot 800*o* is disposed along the y-axis toward the D direction (e.g. 270° position), and the ablation member or electrode 820*o* faces toward the A direction. Thus, as the jawbone is rotatably adjusted throughout its range of motion, the corresponding line or zone of ablation that is created or defined by an ablation member or electrode is rotated in a corresponding fashion.

Ball and Detent Embodiments

Figure 9A:
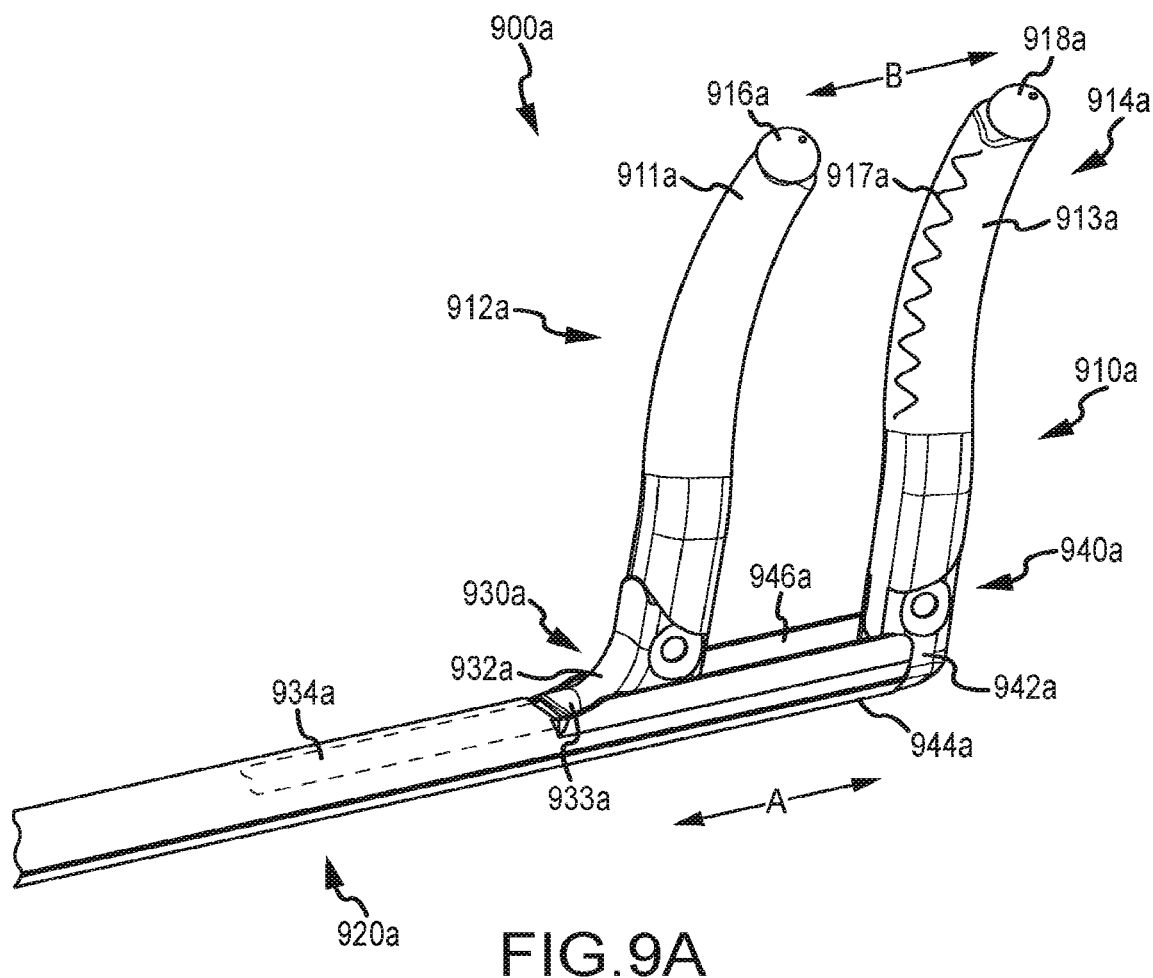
FIGS. 9A to 9C illustrate aspects of treatment systems and methods according to embodiments of the present invention.

FIG. 9A depicts aspects of an adjustable clamp system 900*a* according to embodiments of the present invention. As shown here, clamp system 900*a* includes a clamp assembly 910*a* coupled with or in operative association with a base assembly 920*a*. Clamp assembly 910*a* has a first jaw mechanism 912*a* and a second jaw mechanism 914*a*, and base assembly 920*a* has a first base mechanism 930*a* and a second base mechanism 940*a*. First jaw mechanism 912*a* is coupled with first base mechanism 930*a*, and second jaw mechanism 914*a* is coupled with second base mechanism 940*a*. In use, first and second base mechanisms 930*a*, 940*a* are translated relative to one another, as indicated by arrow A, which in turn causes first jaw mechanism 912*a* and second jaw mechanism 914a to move toward or away from one another, as indicated by arrow B. According to some embodiments, first base mechanism 930a may include a first base 932a coupled with a first base shaft element 934a. Relatedly, second base mechanism 940a can include a second base 942a coupled with a second base shaft element 944a. As depicted here, second base shaft element 944a includes a channel or track 946a that is configured to receive a tongue 933a of first base 932a. Further, each of the first and second jaw mechanisms may include a flexible boot coupled with a flexible ablation member, and optionally an end plug mechanism. For example, first jaw mechanism 912a may include a flexible boot 911a coupled with a flexible ablation member (not shown) and an end plug mechanism 916a. Relatedly, second jaw mechanism 914a may include a flexible boot 913a coupled with a flexible ablation member 917a and an end plug mechanism 918a. According to exemplary embodiments, each of the jaw mechanisms may include a jawbone mechanism (not shown) disposed at least partially within the flexible boot. Such jawbones may be configured to rotate or revolve within or relative to the respective boots 911a, 913a, for example. In some cases, the jawbones may rotate within the boots, while flexible electrode mounting surfaces of the boots remaining facing one another, or toward the tissue which is being ablated by the treatment system. As further discussed elsewhere herein, each of the jaws can be fixed manually by depressing or actuating a ball detent mechanism.

Figure 9B:
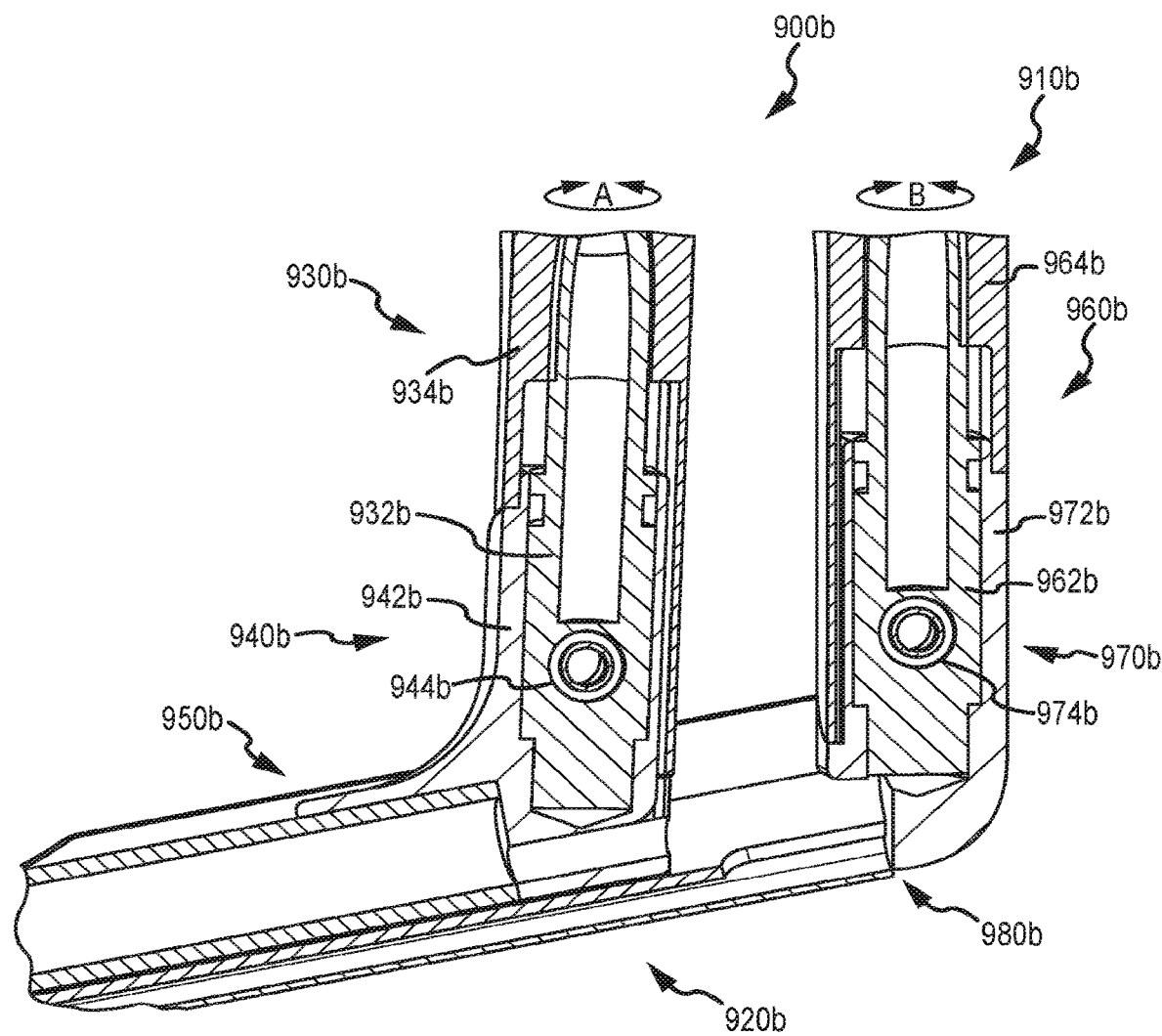

FIG. 9B depicts aspects of an adjustable clamp system 900b according to embodiments of the present invention. As shown here, clamp system 900b includes a clamp assembly 910b coupled with or in operative association with a base assembly 920b. Clamp assembly 910b has a first jaw mechanism 930b and a second jaw mechanism 960b, and base assembly 920b has a first base mechanism 950b and a second base mechanism 980b. First jaw mechanism 930b can be coupled with first base mechanism 950b via a first rotational assembly 940b and second jaw mechanism 960b can be coupled with second base mechanism 980b via a second rotational assembly 970b. In some embodiments, one or more elements of first rotational assembly 940b are part of or integral to first base mechanism 950b. In some embodiments, one or more elements of first rotational assembly 940b are part of or integral to first jaw mechanism 930b. In some embodiments, one or more elements of second rotational assembly 970b are part of or integral to second base mechanism 980b. In some embodiments, one or more elements of second rotational assembly 970b are part of or integral to second jaw mechanism 960b.

First jaw mechanism 930b includes an internal jawbone 932b that can rotate within a flexible boot 934b. Similarly, second jaw mechanism 960b includes an internal jawbone 962b that can rotate within a flexible boot 964b. The flexible boots 934b, 964b are coupled with base mechanisms 950b, 980b, respectively. Hence, each internal jawbone can rotate relative to its respective boot and base mechanism, while the boot and base mechanism remain rotationally stationary with regard to one another. However, the internal jawbones can be shaped so that the interface configuration between the boots changes as the jawbones rotate.

First rotational assembly 940b allows internal jawbone 932b to adjustably rotate relative to base mechanism 950b and boot 934b. For example, first rotational assembly 940b may include a jawbone collar 942b within which jawbone 932b may adjustably revolve, as indicated by arrow A. Similarly, second rotational assembly 970b may include a jawbone collar 972b within which jawbone 962b may adjustably revolve, as indicated by arrow B. As shown here, first rotational assembly 940b may include a collapsible or compressible mechanism 944b and second rotational assembly 970b may include a collapsible or compressible mechanism 974b. The compressible mechanism may include a spring, an elastomeric material, or any other suitable compressible device or material.

Figure 9C:
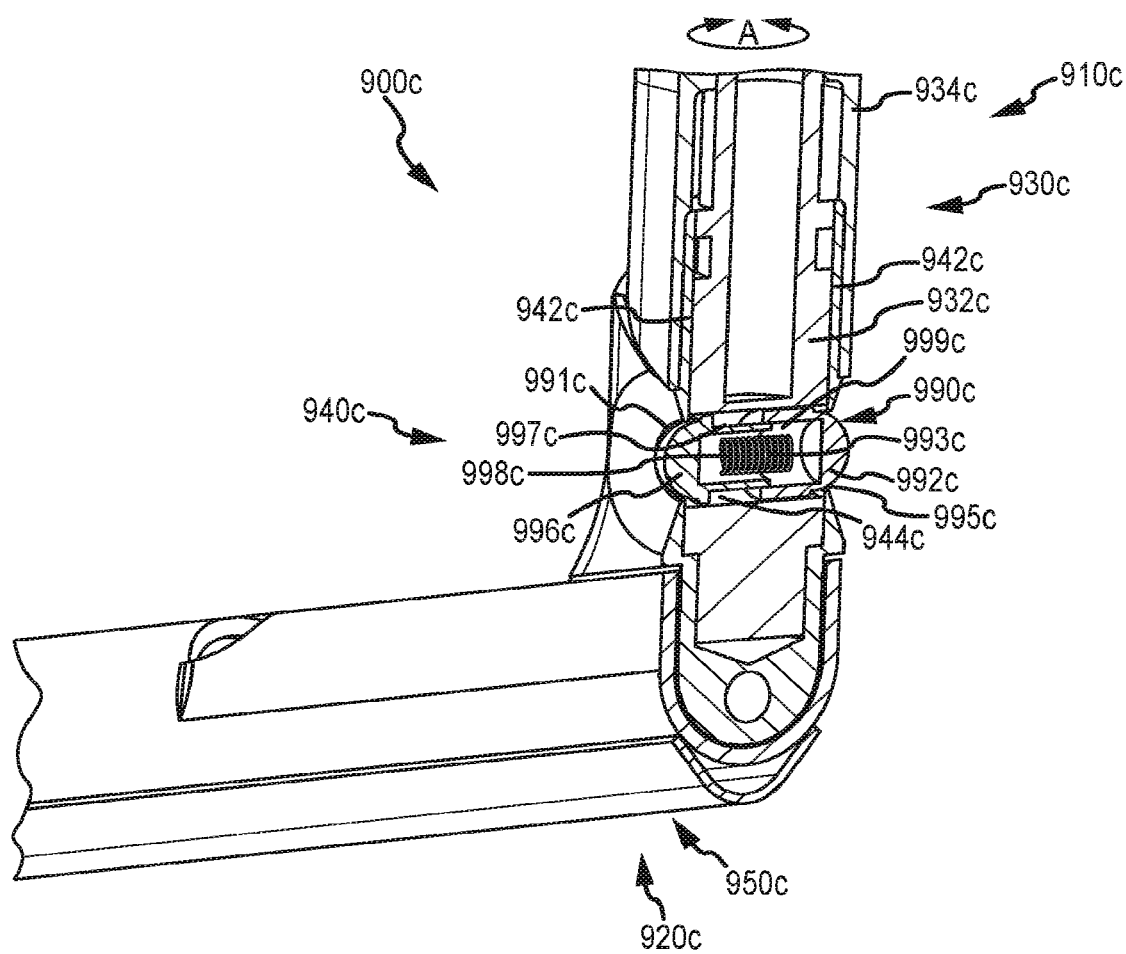

FIG. 9C depicts aspects of an adjustable clamp system 900c according to embodiments of the present invention. As shown here, clamp system 900c includes a clamp assembly 910c coupled with or in operative association with a base assembly 920c. Clamp assembly 910c has a first jaw mechanism 930c, and base assembly 920c has a first base mechanism 950c. First jaw mechanism 930c can be adjustably coupled with first base mechanism 950c, optionally via a first rotational assembly 940c. In some embodiments, one or more elements of first rotational assembly 940c are part of or integral to first base mechanism 950c. In some embodiments, one or more elements of first rotational assembly 940c are part of or integral to first jaw mechanism 930c. First jaw mechanism 930c includes an internal jawbone 932c that can rotate within a flexible boot 934c. The flexible boot can be coupled with or fixed relative to base mechanism 950c. Hence, internal jawbone 932c can rotate relative to base mechanism 950c, while the boot and base mechanism remain rotationally stationary with regard to one another.

First rotational assembly 940c, or optionally base mechanism 950c, allows internal jawbone 932c to adjustably rotate relative to base mechanism 950c and boot 934c. For example, first rotational assembly 940c or base mechanism 950c may include a jawbone collar 942c within which jawbone 932c may adjustably revolve, as indicated by arrow A. As shown here, first jawbone 932c may include an internal channel 944c that houses a compressible mechanism 990c. When the compressible mechanism is sufficiently compressed, the jawbone is free to rotate within collar 942c. When the compressible mechanism is sufficiently decompressed or unsprung, the jawbone is prevented or inhibited from rotating within collar 942c. According to some embodiments, compressible mechanism 990c includes a first contact 992c having a receptacle 993c, and a second contact 996c having a shaft 997c with a receptacle 998c. Compressible mechanism 990c also includes a compressible member 999c disposed within receptacles 993c and 998c. The base mechanism or rotational assembly may include a stop 995c for receiving first contact 992c and a stop 991c for receiving second contact 996c. A compressible member may include a spring, an elastomeric material, or any other suitable compressible element or combination of elements. In some cases, a compressible member or assembly includes one or more rebounding members such as springs, elastomers, elasticized members, as described elsewhere herein. The compressible member 999c can operate to urge or keep contacts 992c, 996c engaged with the stops absent actuation by the user. For example, the contacts can be sprung outward radially, engaging the jaw base and preventing or inhibiting jaw rotation.

In use, an operator may adjust the rotational position of internal jawbone 932c by depressing or squeezing first and second contacts 992c, 996c together or toward each other, thus compressing the compressible member 999c and moving the contacts 992c, 996c inward from stops or pockets 991c, 995c, respectively. Once the contacts are sufficiently withdrawn from their stops or craters, the operator can rotate jawbone 932c as indicated by arrow A. Base mechanism 950c or rotational assembly 940c may include a plurality of stops or pockets into which contacts 992c, 996c may fit. For example, the contacts may present hemispherical surfaces or projections that extend into the pockets, and than can be depressed by the operator back into the pockets thus dislocating the jawbone for subsequent rotational movement. Hence, for example, when the operator has rotated jawbone 932c to the desired rotational configuration, the operator may release or reduce the squeezing force applied to the contacts, thus allowing compressible member 999c to decompress as contacts 992c, 996c move radially outward into their respective stops when so aligned. If the contacts are not aligned with the stops, the contacts remain in a compressed configuration, for example as they are constrained within jawbone collar 942c. In this sense, the jawbone and the compressible mechanism rotate in unison within or relative to the jawbone collar. When contacts 992c, 996c are disposed within or otherwise engaged with the stops, compressible mechanism 990c can operate to prevent or inhibit rotational movement of jawbone 932c within collar 942c.

Side Ratchet Embodiments

Figure 10A:
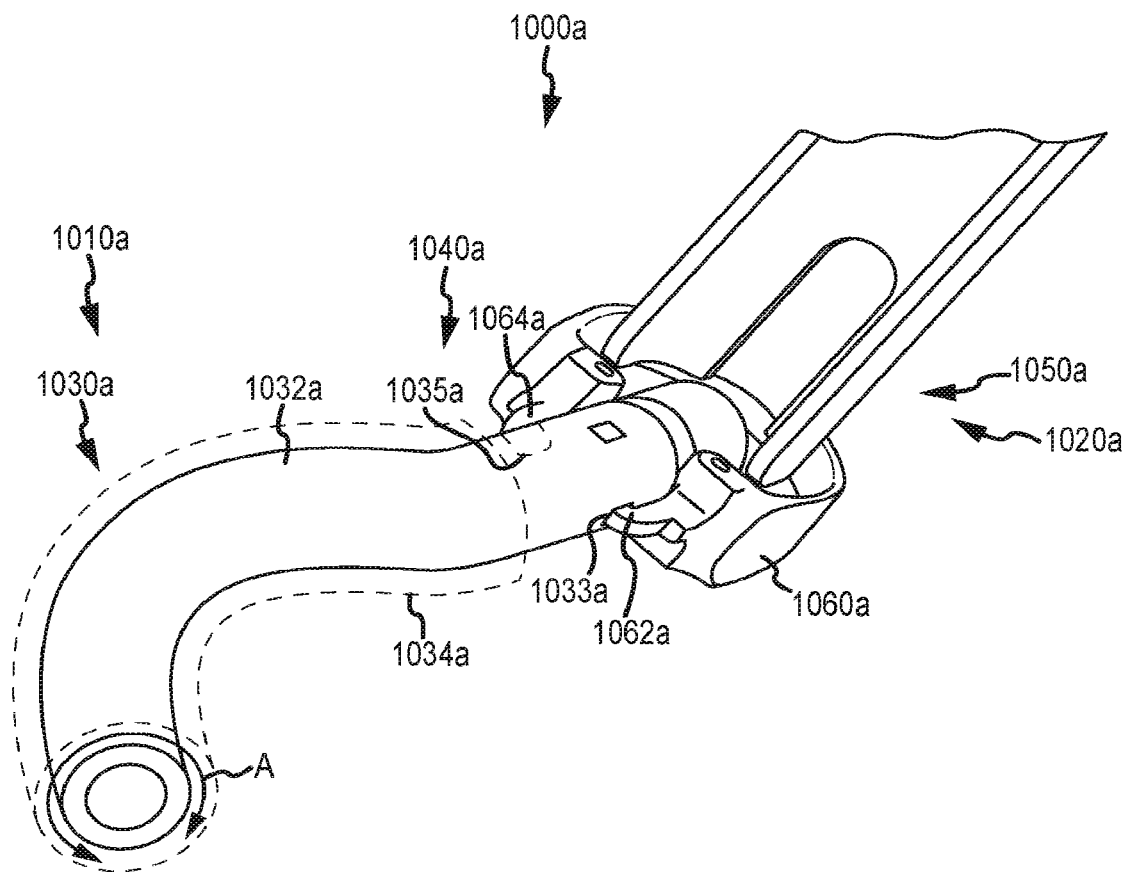

FIG. 10A depicts aspects of an adjustable clamp system 1000a according to embodiments of the present invention. As shown here, clamp system 1000a includes a clamp assembly 1010a coupled with or in operative association with a base assembly 1020a. Clamp assembly 1010a has a first jaw mechanism 1030a, and base assembly 1020a has a first base mechanism 1050a. First jaw mechanism 1030a can be adjustably coupled with first base mechanism 1050a, optionally via a first rotational assembly 1040a. In some embodiments, one or more elements of first rotational assembly 1040a are part of or integral to first base mechanism 1050a. In some embodiments, one or more elements of first rotational assembly 1040a are part of or integral to first jaw mechanism 1030a. First jaw mechanism 1030a includes an internal jawbone 1032a that can rotate within a flexible boot 1034a. The flexible boot can be coupled with or fixed relative to base mechanism 1050a. Hence, internal jawbone 1032a can rotate relative to base mechanism 1050a as indicated by arrow A, while the boot and base mechanism remain rotationally stationary with regard to one another. In some embodiments, the rotation may not be about the axis that is along the centerline of the end of the jawbone, where it is housed by the jaw base assembly. The end of the jawbone can travel in a circle around an axis collinear with the proximal jawbone straight section. The clamp system can include a moveable engagement mechanism 1060a, optionally as part of base assembly 1020a or rotational assembly 1040a. Engagement mechanism 1060a includes first and second tangs or prongs 1062a, 1064a. Relatedly, jawbone 1032a includes recesses or apertures 1033a, 1035a that are configured to receive or engage tangs 1062a, 1064a. Engagement mechanism 160a can provide spring-actuated operation. For example, the engagement mechanism can operate to urge or force spring-loaded engagement tangs into recesses or apertures of the jawbone.

Figure 10B:
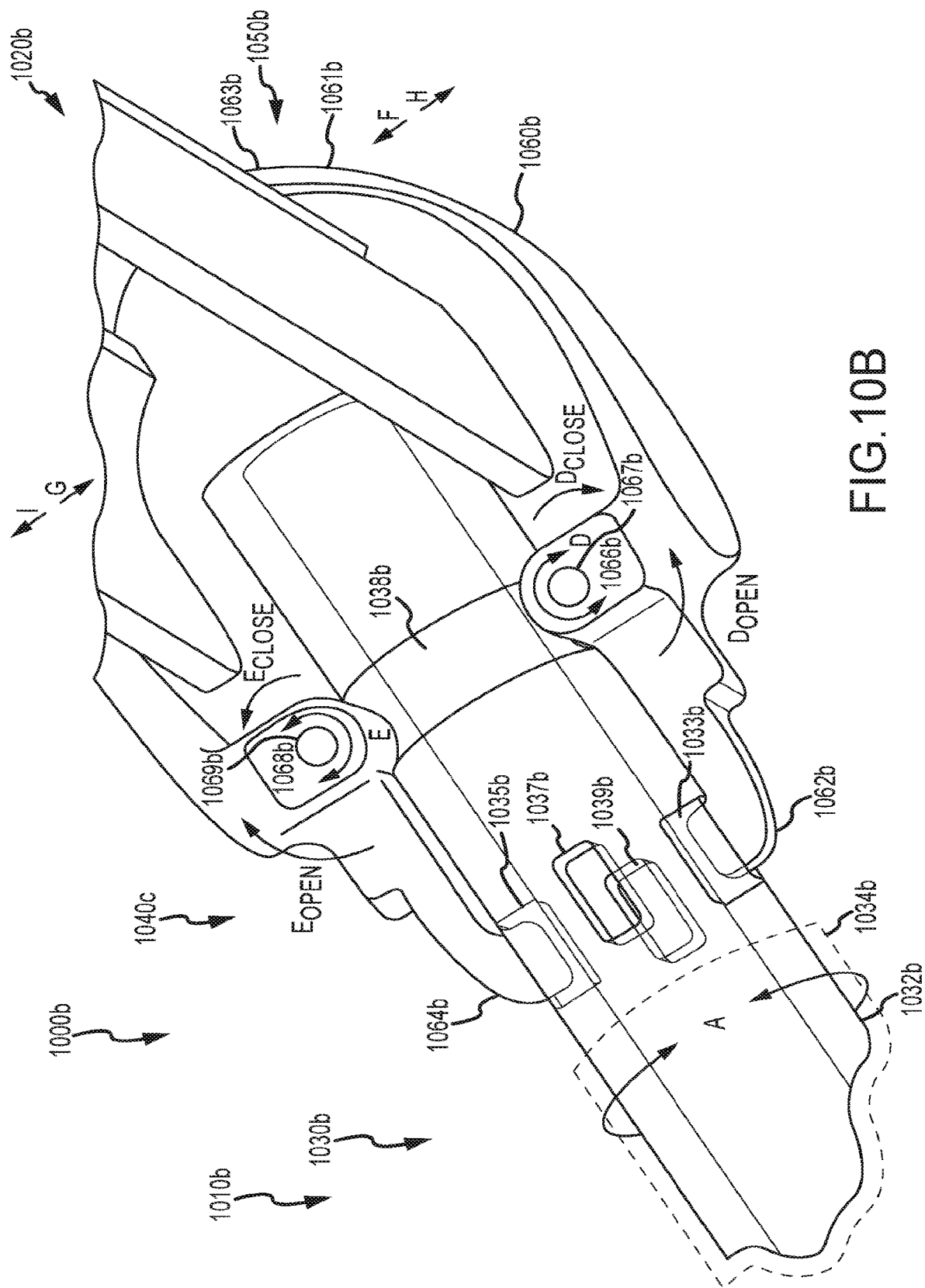

FIG. 10B shows aspects of an adjustable clamp system 1000b according to embodiments of the present invention. As shown here, clamp system 1000b includes a clamp assembly 1010b coupled with or in operative association with a base assembly 1020b. Clamp assembly 1010b has a first jaw mechanism 1030b, and base assembly 1020b has a first base mechanism 1050b. First jaw mechanism 1030b can be adjustably coupled with first base mechanism 1050b, optionally via a first rotational assembly 1040b. In some embodiments, one or more elements of first rotational assembly 1040b are part of or integral to first base mechanism 1050b. In some embodiments, one or more elements of first rotational assembly 1040b are part of or integral to first jaw mechanism 1030b. First jaw mechanism 1030b includes an internal jawbone 1032b that can rotate within a flexible boot 1034b. The flexible boot can be coupled with or fixed relative to base mechanism 1050b. Hence, internal jawbone 1032b can rotate relative to base mechanism 1050b as indicated by arrow A, while the boot and base mechanism remain rotationally stationary with regard to one another. The clamp system can include a moveable engagement mechanism 1060b, optionally as part of or coupled with base assembly 1020b or rotational assembly 1040b. Engagement mechanism 1060b includes first and second tangs or prongs 1062b, 1064b. Relatedly, jawbone 1032b includes recesses or apertures 1033b, 1035b, 1037b, 1039b that are configured to receive or engage tangs 1062b, 1064b.

Jawbone 1032b also includes a groove or annular track 1038b configured to cooperatively associate with one or more bosses 1066b, 1068b of engagement mechanism 1060b. Bosses 1066a and 1068b are configured to rotate or pivot relative to annular track 1038b, as indicated by arrows D and E, respectively. Bosses 1066b, 1068b may also operate to prevent or inhibit axial translation of the jawbone along the long axis of the jawbone, for example when engaged with annular groove 1038b. The engagement mechanism can include a flexible ribbon of steel that operates as a spring. In use, an operator may squeeze or compress together a first portion 1061b of engagement mechanism 1060b, as indcted by arrows F and G, which causes bosses 1066b, 1068b to pivot or rotate relative to the annular track, as indicated by arrows $D_{open}$ and $E_{open}$, respectively. As a result, tangs 1062b, 1064b retract from recesses 1033b, 1035b, respectively, thus allowing jawbone 1032b to freely rotate relative to base assembly 1020b. In this way, by deactivating or releasing the engagement mechanism, the operator can subsequently rotate the jawbone to another desired orientation relative to the base assembly. For example, in the configuration shown in FIG. 10B, tangs 1062b, 1064b are engaged with recesses 1033b, 1035b, respectively. After releasing the engagement mechanism, the operator can rotate the jawbone by 180 degrees, and then reactivate or secure the engagement mechanism, so that tangs 1062b, 1064b are engaged with recesses 1035b, 1033b, respectively. More specifically, the operator can let go or release compression at first portion 1061b of engagement mechanism 1060b, as indcted by arrows H and I, which causes bosses 1066b, 1068b to pivot or rotate relative to the annular track, as indicated by arrows $D_{close}$ and $E_{close}$, respectively. As a result, tangs 1062b, 1064b protrude into recesses 1033b, 1035b, respectively, thus preventing or inhibiting jawbone 1032b from freely rotating relative to base assembly 1020b. As shown here, engagement mechanism 1060b includes a spring element 1063b that biases or urges tangs or spring loaded tabs 1062b, 1064b toward the jawbone. In some cases, bosses 1066b, 1068b can rotate relative to hinge pins 1067b, 1069b.

According to some embodiments, the presence of multiple recesses or apertures about the perimeter of the jawbone proximal end allow the engagement mechanism to lock the jawbone into a variety of useful positions. For example, where the jawbone provides a curved or other contoured shape, the rotational orientation of the jawbone can be selected and locked as appropriate, so as to present a shape that contours or interfaces with the anatomical tissue as desired. In a system that includes two jawbones, the first and second jawbones can therefore be positioned so that the interface between the two jawbones is disposed in a horizontal plane, a vertical plane, or any other plane as desired.

In this way, the jawbone curves can provide opposing electrode surfaces in any suitable plane for treating the patient. As noted elsewhere herein, a jawbone can include one or more recesses or holes which are configured to releasably receive tangs of an engagement mechanism. The jawbone can also includes a groove or annular track configured to cooperatively associate with one or more engagement mechanism bosses. The jawbone groove can allow the boss, pin, or other stationary feature relative to the base to locate the jawbone axially, prevent the jawbone from falling out of the base, and allow rotation of the jawbone relative to the base. Multiple holes or recesses can allow the jawbone to be locked into useful positions so that jaw curves or electrode faces of upper and lower jaw mechanisms oppose each other in horizontal, vertical, or any other planes.

FIG. 10C shows aspects of an adjustable clamp system 1000c according to embodiments of the present invention. As shown here, clamp system 1000c includes a clamp assembly 1010c coupled with or in operative association with a base assembly 1020c. Clamp assembly 1010c has a first jaw mechanism 1030c, and base assembly 1020c has a first base mechanism 1050c. First jaw mechanism 1030c can be adjustably coupled with first base mechanism 1050c, optionally via a first rotational assembly 1040c. In some embodiments, one or more elements of first rotational assembly 1040c are part of or integral to first base mechanism 1050c. In some embodiments, one or more elements of first rotational assembly 1040c are part of or integral to first jaw mechanism 1030c. First jaw mechanism 1030c includes an internal jawbone 1032c that can rotate within a flexible boot 1034c. The flexible boot can be coupled with or fixed relative to base mechanism 1050c. Hence, internal jawbone 1032c can rotate relative to base mechanism 1050c as indicated by arrow A, while the boot and base mechanism remain rotationally stationary with regard to one another. The clamp system can include a moveable engagement mechanism 1060c, optionally as part of or coupled with base assembly 1020c or rotational assembly 1040c. Engagement mechanism 1060c includes one or more tangs 1062c, and jawbone 1032c includes one or more recesses (not shown) that are configured to receive or engage an engagement tang. In use, an operator may squeeze the engagement mechanism as indicated by arrow B, for example at activation area 1070c, which is located proximal to pivot boss 1066c. As a result of such actuation, a proximal spring portion 1061c bows outward or backward as indicated by arrow C, and tang 1062c is released from engagement with the jawbone, thus allowing the jawbone to rotate. According to some embodiments, proximal spring portion 1061c can provide a snag-free spring.

Tuning Fork Embodiments

Figure 11A:
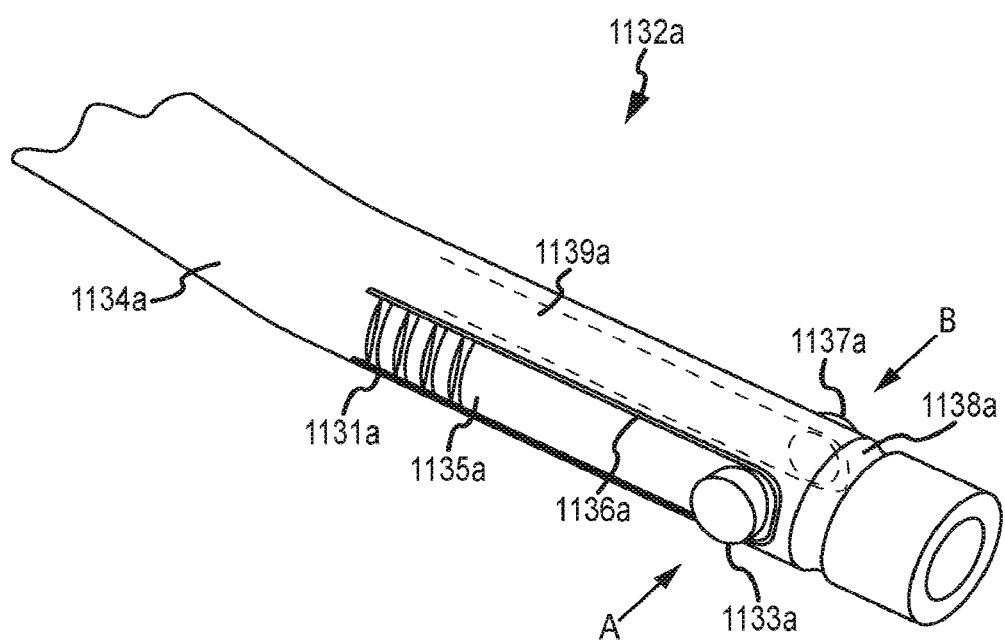
FIG. 11A illustrates aspects of treatment systems and methods according to embodiments of the present invention.

FIG. 11A illustrates aspects of a proximal portion of a jawbone 1132a according to embodiments of the present invention. Jawbone 1132a includes one or more protrusions or buttons 1133a, 1137a which are configured to releasably engage one or more recesses of an engagement mechanism or base assembly. Jawbone 1132a also includes a groove or annular track 1138a configured to cooperatively associate with one or more engagement mechanism or base assembly bosses. The axial securing groove can keep the jawbone from moving lengthwise, or otherwise locate the jawbone relative to the base, while at the same time allowing the jawbone to rotate relative to a base or boot. A pin or boss in the base, for example a pin or boss similar to that which is described in association with pins 1067b, 1069b or bosses 1066b, 1068b shown in FIG. 10B, can be positioned to intersect the groove. Optionally, the jawbone can be used in conjunction with an anchoring mechanism fixed relative to a base, such that the anchoring mechanism provides anchor elements that can be positioned or disposed tangentially through or radially into the side of the groove, thus allowing the jawbone to rotate while maintaining the jawbone in an axially stationary position. In this sense, a pin or boss can help to locate the jawbone, and keep it secured at an axial location relative to the base. As shown here, the protrusions or tangs 1133a, 1137a are disposed toward the ends of respective flexible fingers 1135a, 1139a of the jawbone. With regard to flexible finger 1135a, the finger can be formed by a "U" shaped cut 1136a in a side wall 1134a of the jawbone. Accordingly, the base of the fingers may be continuous with the body of the jawbone. Flexible finger 1135a may also include one or more flexibility slits or thin sections 1131a that allow the flexible finger to more easily flex or move with respect to the jawbone, for example when the operator or user squeezes against buttons or pins 1133a, 1137a, as indicated by arrows A and B, respectively. Hence, by squeezing the buttons, the operator can force the buttons toward the central longitudinal axis of the jawbone. The protrusions can act as rotationally locking mechanisms. The protrusions can also act as manual push buttons that can engage corresponding holes or apertures in a base or rotational assembly. Jawbone 1132c can be used in conjunction with other aspects of a treatment system, such as those shown in FIG. 9C. For example, jawbone 1132c can be placed in operative association with a collar similar to collar 942c of treatment system 900c. Likewise, buttons 1133a, 1137a can be compressed or relaxed so as to engage or disengage from the pockets or craters shown in FIG. 9C.

Figure 12A:
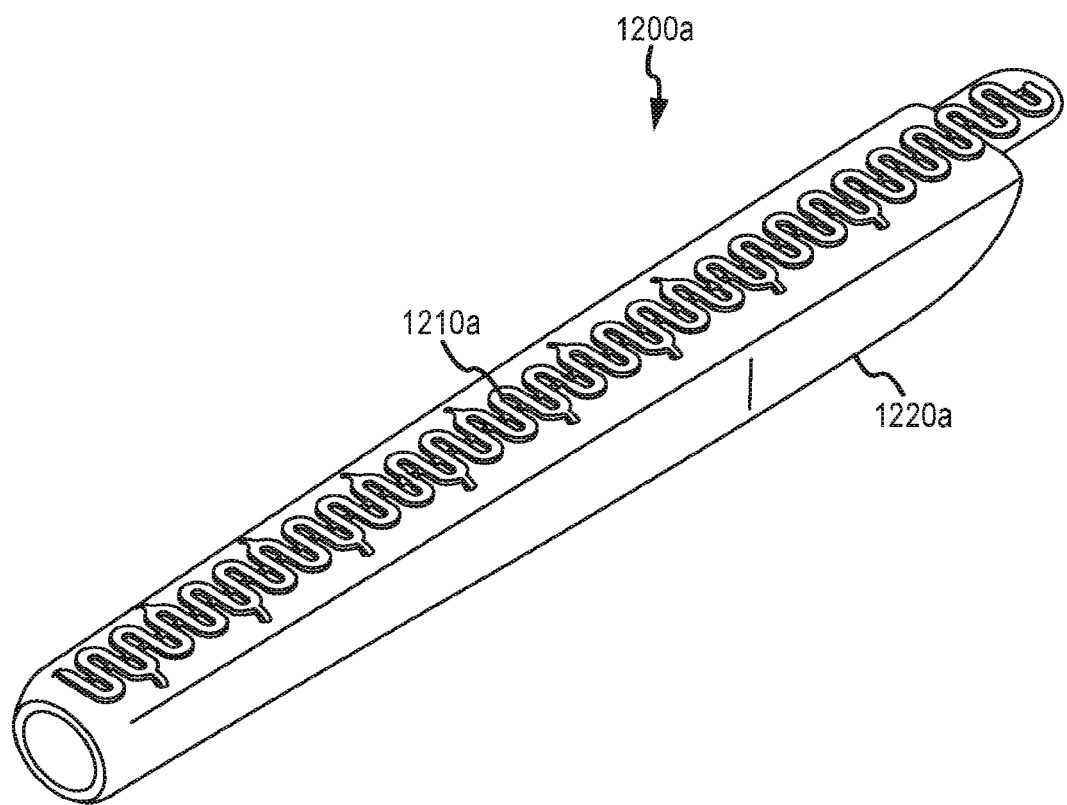
FIGS. 12A and 12B illustrate aspects of treatment systems and methods according to embodiments of the present invention.
Figure 12B:
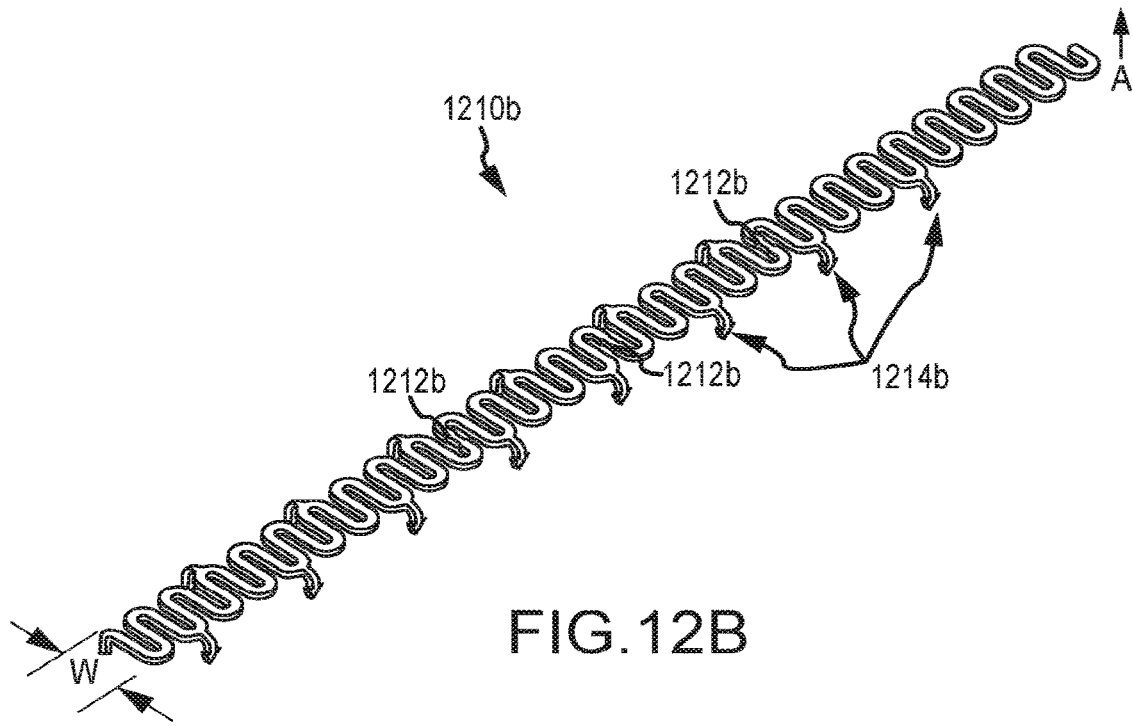

FIG. 12A depicts aspects of an ablation member or electrode assembly 1200a according to embodiments of the present invention. As shown here, ablation member assembly 1200a can include an ablation member 1210a such as an electrode, optionally in combination with a flexible support or boot 1220a. In some cases, boot 1220a includes a polymer sleeve, which may include urethane or another flexible material. The electrode assembly is flexible in three dimensions, and thus can accommodate rotational movement of a curved jawbone disposed within the interior of the boot. For example, the electrode assembly may flex relative to the x-axis, the y-axis, and the z-axis of a standard Cartesian coordinate system. The ablation member can be anchored or embedded into the flexible boot. Relatedly, FIG. 12B shows aspects of an ablation member 1210b according to embodiments of the present invention. In some cases, ablation member 1210b can include a flexible electrode. The electrode illustrated here provides a generally serpentine shape. In some cases, an electrode can present an accordionated or other repetitively shaped configuration. As shown here, ablation member 1210b includes a plurality of alternating looped or curved sections. In some cases, the ablation member assembly may provide one or more sections that more densely arranged loops, such that loops are present at a higher pitch or count per length. In some cases, the ablation member assembly may provide one or more sections that more loosely arranged loops, such that loops are present at a lower pitch or count per length. Ablation member 1210b can flex sideways, up and down, and in an S-curve configuration. As depicted here, ablation member 1210b can be a thin flexible element that bends without yielding. In some cases, an ablation member can include one or more break points 1212b that present structurally weakened sections. As shown here, the break points are configured in a hourglass shape. An operator may sharply bend the electrode at the break points, causing the electrode to break at the break point, so as to create multiple smaller electrode pieces. Optionally, sharp edges of broken break points can be ground away or otherwise smoothed prior to further use. As noted elsewhere herein, ablation member 1210b can include one or more tangs or barbed points 1214b According to some embodiments, tangs or anchoring pints 1214b can operate to help provide a mechanical connection between an ablation member 1210b and a flexible boot. In some cases, an adhesive can also be used to help provide a chemical connection or bond between an ablation member an a flexible boot. When the ablation member and boot are suitably secured with one another, a flexing motion of the boot creates a corresponding flexing motion in the ablation member. When operating as an indifferent electrode, ablation member 1210b may be coupled with a single wire. When operating as an active electrode, ablation member 1210b may be coupled with an RF wire, for example at a central portion of the ablation member, and two thermocouple pairs, for example at opposing end portions of the ablation member. In some cases, the ablation member can have a width W within a range from about 0.050 to about 0.150 inches.

Because a boot and an electrode can flex in unison, the ablation assembly can accommodate any of a variety of surgical situations, such as when the patient tissue presents surface irregularities, changes in surface density, changes in tissue density, changes in tissue thickness, and the like. Thus, two opposing jaw mechanisms can provide equilibrated or normalized pressure to both sides of the tissue, even where the tissue presents lumps or bumps between the jaw members. The boots and electrodes can bend, pivot, rotate, twist, or otherwise conform to accommodate the tissue that is being clamped. In some cases the boot and electrode assembly bends along the length of the assembly. In some cases, the boot and electrode assembly bends from side to side. Hence, the ablation assembly can maintain a maximal amount of contact with the surface of the tissue, while the electrode twists and conforms with the tissue surface irregularities. Relatedly, the ablation assembly provides a maximal amount of contact while minimizing high or extreme pressure points. For example, where the contact pressure would otherwise be higher, the electrode assembly can accommodate the tissue and therefore transmit a relatively lower amount or percentage of clamping force to that tissue point. Conversely, where the contact pressure would otherwise be lower, the electrode assembly can accommodate the tissue and therefore transmit a relatively higher amount or percentage of clamping force to that tissue point. Accordingly, the treatment system can provide improved surface contact and equalized pressure along the length of and across the sides of the ablation members or electrodes. In some cases the compliant nature of the jaw surface and electrode allows these elements to conform to tissue irregularities. In some cases, an electrode can have a length of about 70 mm.

Figure 13:
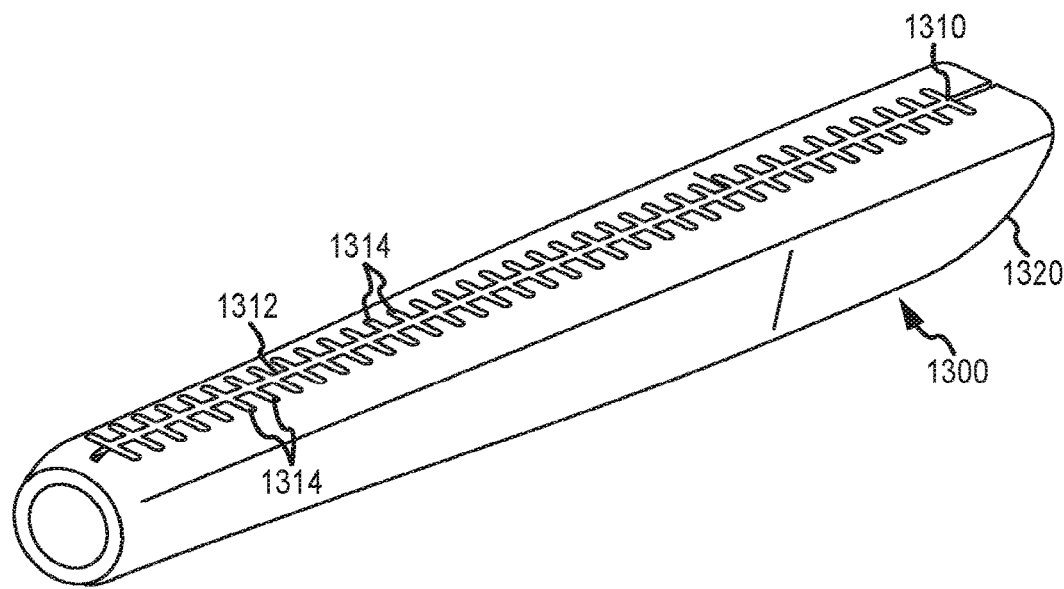
FIG. 13 illustrates aspects of treatment systems and methods according to embodiments of the present invention.

FIG. 13 depicts aspects of an ablation member or electrode assembly 1300 according to embodiments of the present invention. As shown here, ablation member assembly 1300 can include an ablation member 1310 such as an electrode, optionally in combination with a flexible support or boot 1320. The electrode illustrated here provides a generally fishbone shape, and includes a central rib 1312 and one or more laterally extending side ribs 1314. According to some embodiments, ablation member 1310 and boot 1320 are both pliant, and can flex in a coordinated manner. The ablation member assembly 1300 can flex as a unitary ensemble, such that the ablation member and boot move in a coordinated manner in three dimensions with respect to the x-axis, y-axis, and z-axis of a Cartesian coordinate system. In an exemplary embodiment, a treatment system includes two electrode assemblies, each of which is flexible in three dimensions, whereby the position of the respective electrodes is maintained such that an electrode of one assembly faces toward a corresponding electrode of the other assembly. Electrodes can include a thin metal material, and can bend without yielding. In some cases, an electrode can present a serpentine or accordionated shape. In some cases, an electrode can have a series of aligned elements situated along a central element or axis.

Flat Plate Electrode Embodiments

Figure 14A:
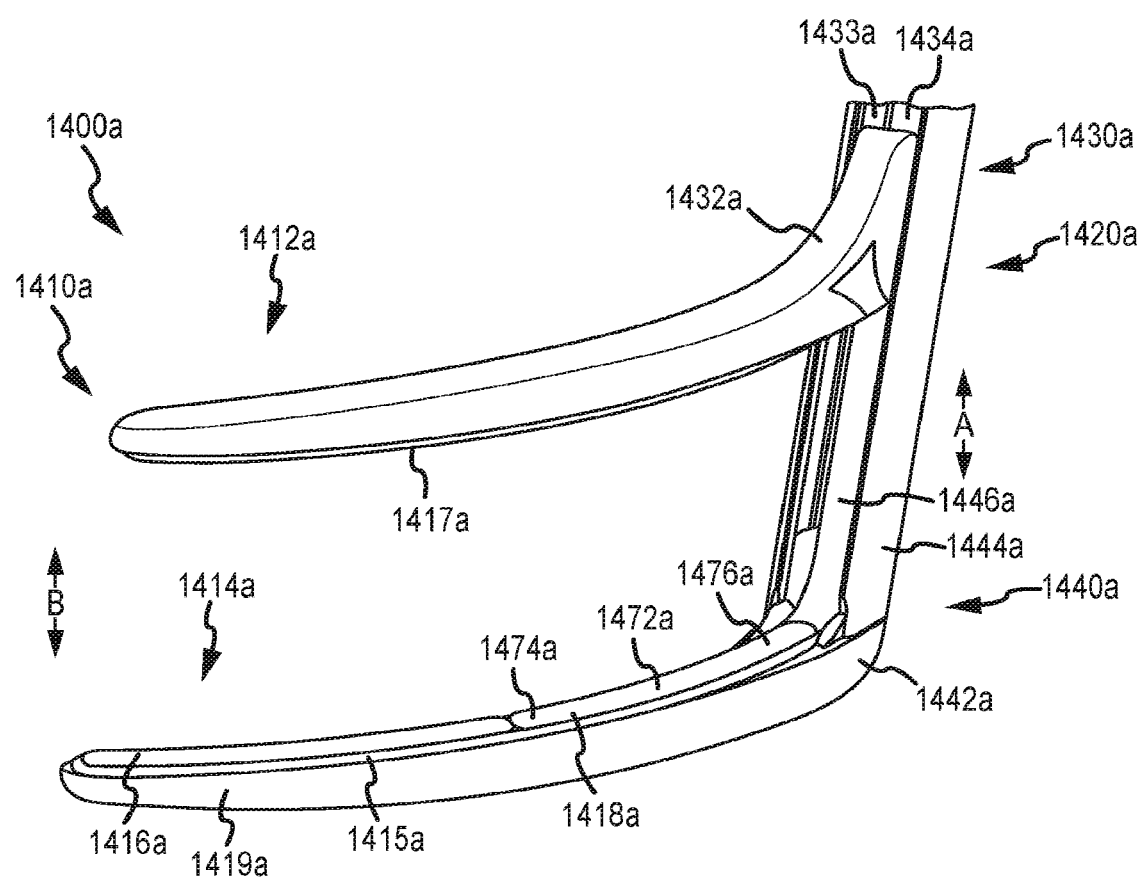
FIGS. 14A to 14D illustrate aspects of treatment systems and methods according to embodiments of the present invention.

FIG. 14A depicts aspects of an adjustable clamp system 1400a according to embodiments of the present invention. As shown here, clamp system 1400a includes a clamp assembly 1410a coupled with or in operative association with a base assembly 1420a. Clamp assembly 1410a has a first jaw mechanism 1412a and a second jaw mechanism 1414a, and base assembly 1420a has a first base mechanism 1430a and a second base mechanism 1440a. First jaw mechanism 1412a is coupled with first base mechanism 1430a, and second jaw mechanism 1414a is coupled with second base mechanism 1440a. In use, first and second base mechanisms 1430a, 1440a are translated relative to one another, as indicated by arrow A, which in turn causes first jaw mechanism 1412a and second jaw mechanism 1414a to move toward or away from one another, as indicated by arrow B. According to some embodiments, first base mechanism 1430a may include a first base 1432a coupled with a first base shaft element 1434a. Relatedly, second base mechanism 1440a can include a second base 1442a coupled with a second base shaft element 1444a. As depicted here, second base shaft element 1444a includes a channel or track 1446a that is configured to receive a tongue 1433a of first base 1432a. The jaw mechanisms 1412, 1414a may also include one or more ablation members or electrodes. For example, first jaw mechanism 1412a may include one or more ablation members 1417a and second jaw mechanism 1414a may include one or more ablation members 1416a, 1418a. Ablation members can be active or indifferent. Typically, an ablation member of one jaw mechanism faces toward an ablation member of the other jaw mechanism. In some cases, a jaw mechanism may include a base member in operative association with an electrode. For example, as shown here, jaw mechanism 1414a includes a base member 1415a coupled with ablation members 1416a, 1418a and a jaw mechanism support 1419a. First jaw mechanism 1412a may include a similar arrangement. In some cases, jaw mechanism support 1419a includes a metallic material such as steel, and base member 1415a includes a non-metallic material such as plastic. Base member may in some instances include a material that provides electrical insulation, thermal insulation, or both. Optionally, base member 1415a can include a flexible or deformable material, such as an elastomer. Hence, the electrodes can be isolated, either electrically, thermally, or both, from the base jaws which may be constructed of metal such as steel. Electrical isolation of the electrodes can prevent them from being ground. In some cases, a jaw mechanism may include any number of ablation members. For example, a jaw mechanism may include 10 or more ablation members. Accordingly, the jaw mechanism can present a flexible or conformable configuration, wherein multiple ablation members are disposed upon a flexible or deformable base member. In some cases, a series of multiple nonflexible ablation members may operate on the whole or collectively as a single flexible ribbon. The ablation members may include elements of a cooling apparatus. In use, the ablation members can absorb heat from tissue which is being ablated. Saline or other cooling fluid may be routed along the ablation members, or other elements of the jaw mechanism, so as to draw heat away from the ablation members. In some cases, ablation members may have connection points for coupling with other system features. For example, ablation member 1418a can have a connection point 1472a for coupling with an RF element, a connection point 1474a for coupling with a distal thermocouple pair, and a connection point 1476a for coupling with a proximal thermocouple pair. In some cases, ablation member 1417a can be configured as an indifferent electrode.

Figure 14B:
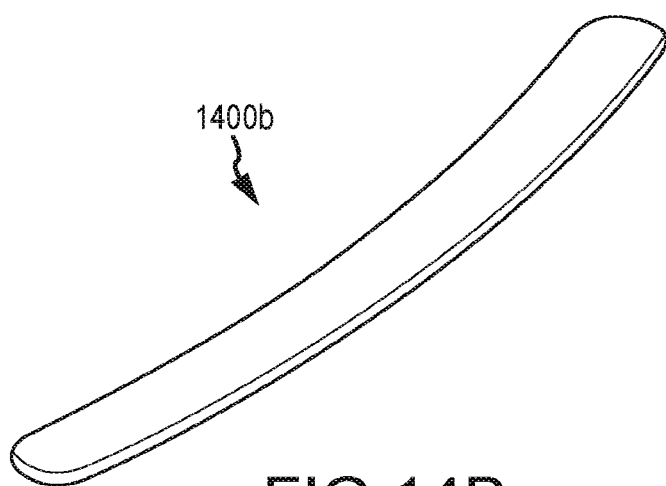
Figure 14C:
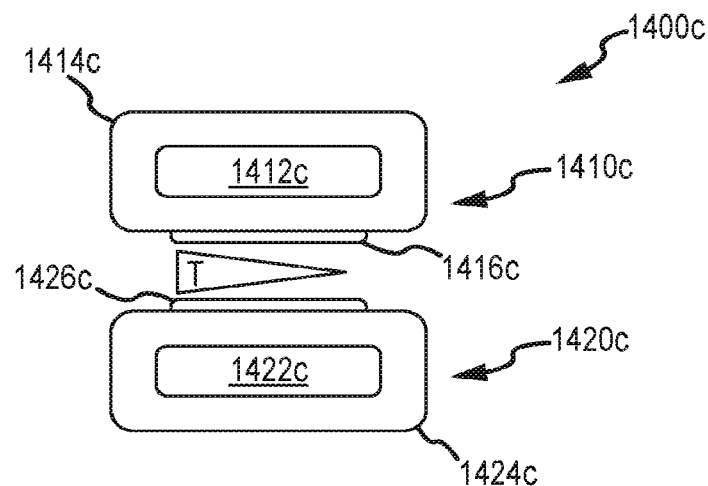
Figure 14D:
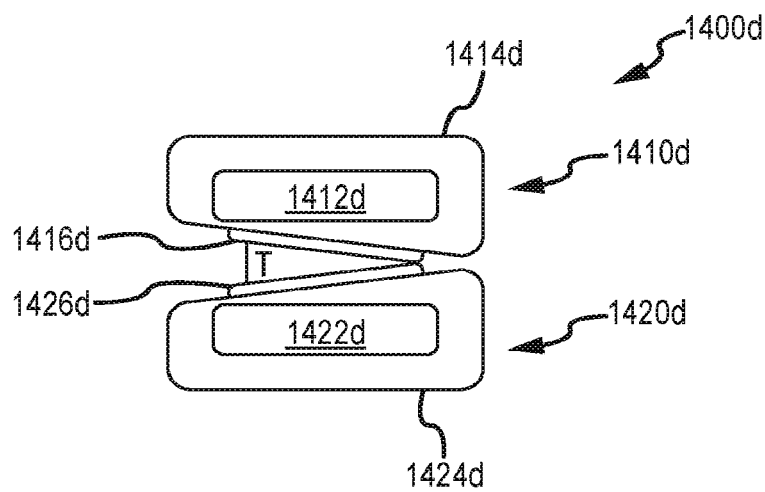

FIG. 14B illustrates an ablation member 1400b according to embodiments of the present invention. In some cases, ablation member 1400b includes a non-compliant or rigid material such as steel. In some cases, an ablation member can include a flexible material, or can otherwise be configured to present a flexible configuration. FIG. 14C shows an end view or cross-section of an exemplary clamp assembly 1400c. As shown here, the clamp assembly includes a first jaw mechanism 1410c and a second jaw mechanism 1420c. First jaw mechanism 1410c includes a jawbone 1412c disposed toward the interior of a boot 1414c, and an electrode 1416c disposed toward the exterior of boot 1414c. Second jaw mechanism 1420c includes a jawbone 1422c disposed toward the interior of a boot 1424c, and an electrode 1426c disposed toward the exterior of boot 1424c. The clamp assembly can provide compliance during a treatment, so as to accommodate tissue having various thicknesses, densities, irregularities, and the like. For example, as shown in FIG. 14D, the flexible boot and electrode can flex and conform with a patient tissue. Clamp assembly 1400d includes a first jaw mechanism 1410d and a second jaw mechanism 1420d that can engage a patient tissue T. First jaw mechanism 1410d includes a jawbone 1412d disposed toward the interior of a boot 1414d, and an electrode 1416d disposed toward the exterior of boot 1414d. Second jaw mechanism 1420d includes a jawbone 1422d disposed toward the interior of a boot 1424d, and an electrode 1426d disposed toward the exterior of boot 1424d. As shown here, flexible boots 1414d, 1424d and flexible electrodes 1416d, 1426d can bend or flex so as to conform with or accommodate the shape of tissue T, optionally while jawbones 1412d, 1422d do not bend or flex relative to one another. Such flexible clamp assemblies can be used to clamp tissue, while providing equalized or balanced clamping forces toward each clamp site on the tissue. A high degree of tissue contact can be maintained, without producing unwanted high or extreme pressure points on the tissue.

Cooling Apparatus Embodiments

In some cases, the thermal mass of the jaw construction can allow the device to operate effectively without a cooling mechanism for the electrodes. In some cases, a device includes thick urethane boots over the steel jawbone which insulates the electrode from the heat sink effect of the jawbone. In the cooled design herein described, the jawbone in one example is an active part of the cooling system.

Figure 15:
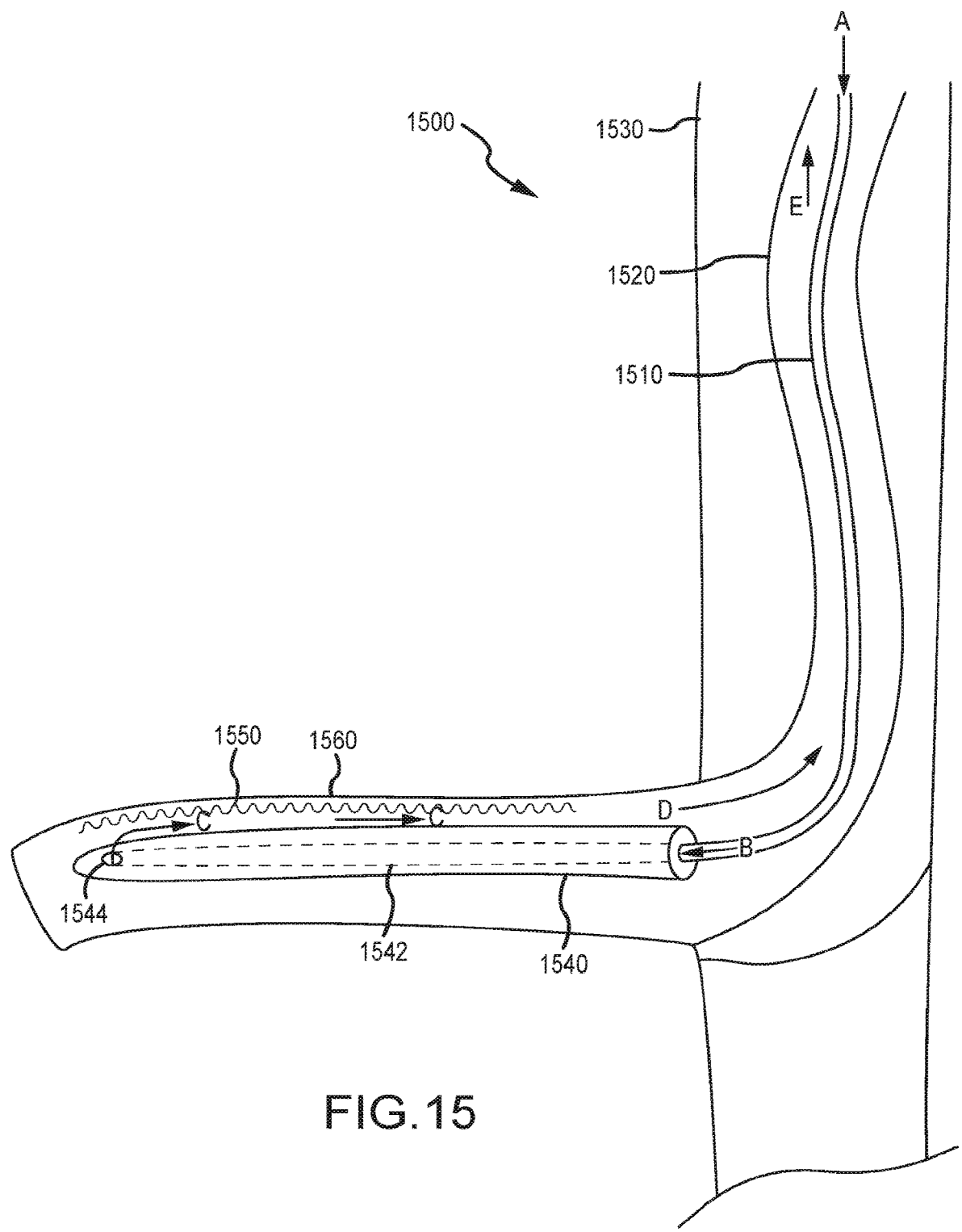
FIG. 15 illustrates aspects of treatment systems and methods according to embodiments of the present invention.

During the operation of an ablation system, applied RF energy can cause an increase in tissue temperature, which in turn causes an increase in temperature in the ablation system elements. If certain elements of the treatment system, such as the electrodes, become excessively hot, they may char or damage the surface of the tissue with which they are in contact. In a treatment system having rigid jaws, a cooling apparatus may include tubes or passages extending along the length of the device shaft. A fluid delivery tube can deliver cooling fluid through a clamp jaw, and across or near heated elements of the jaw so as to absorb heat from those elements. A fluid return tube can carry the heated fluid away from the clamp jaw. In this way, a cooling apparatus can operate as a heat sink, removing unwanted heat from electrodes or other elements of a treatment system. FIG. 15 shows aspects of a cooling system 1500 according to embodiments of the present invention. Cooling system 1500 includes two concentrically arranged tubes or passages. A smaller, narrower fluid delivery tube 1510 is disposed within a larger, wider fluid return tube 1520. As shown here, fluid delivery tube 1510 operates to deliver cooling fluid, such as saline, through a treatment system shaft 1530 in a distal direction as indicated by arrow A, and into an interior passage 1542 of a hollow jawbone 1540 as indicated by arrow B. Typically, fluid is delivered through delivery tube 1510 at a relatively high pressure. The cooling fluid passes distally through jawbone 1540, and exits a distal section of the jawbone at fluid port 1544. In some cases, the smaller tube carry the inflow water to a location close to the plugged distal end of the jawbone where the water exits the small tube and flows back inside the jawbone, thereby carrying away heat picked up by the jawbone. Optionally, tube 1520 can be connected distally to the jawbone to pick up the water, and not outside the jawbone as depicted in FIG. 15. The fluid then flows in a proximal direction as indicated by arrow C, across or near an electrode 1550 that is coupled with a boot 1560, and across or near the outside or exterior of the jawbone. In this way, the fluid can absorb heat from the electrode, the boot, or the jawbone, or any combination thereof. The fluid then continues to flow proximally into the shaft as indicated by arrow D, and through fluid return tube 1520 toward a fluid source or return depot, as indicated by arrow E. In some cases, a treatment system handle may include a manifold that is configured to fluidly couple with fluid delivery tube 1510 and fluid return tube 1520. In some embodiments, boot 1560 may include thermally transmissive materials or metallic-loaded plastics, such as carbon, graphite, or other additives, which operate to transmit thermal energy from the boot or electrode toward the jawbone. Although the jawbone may not directly contact the electrode, thermal energy can be transmitted from the electrode, through the boot, and to the jawbone. According to some embodiments, the boot can have a thickness of a few thousandths of an inch. In some cases, the thickness of the boot can be within a range of about 0.01 inch to about 0.1 inch.

Figure 16A:
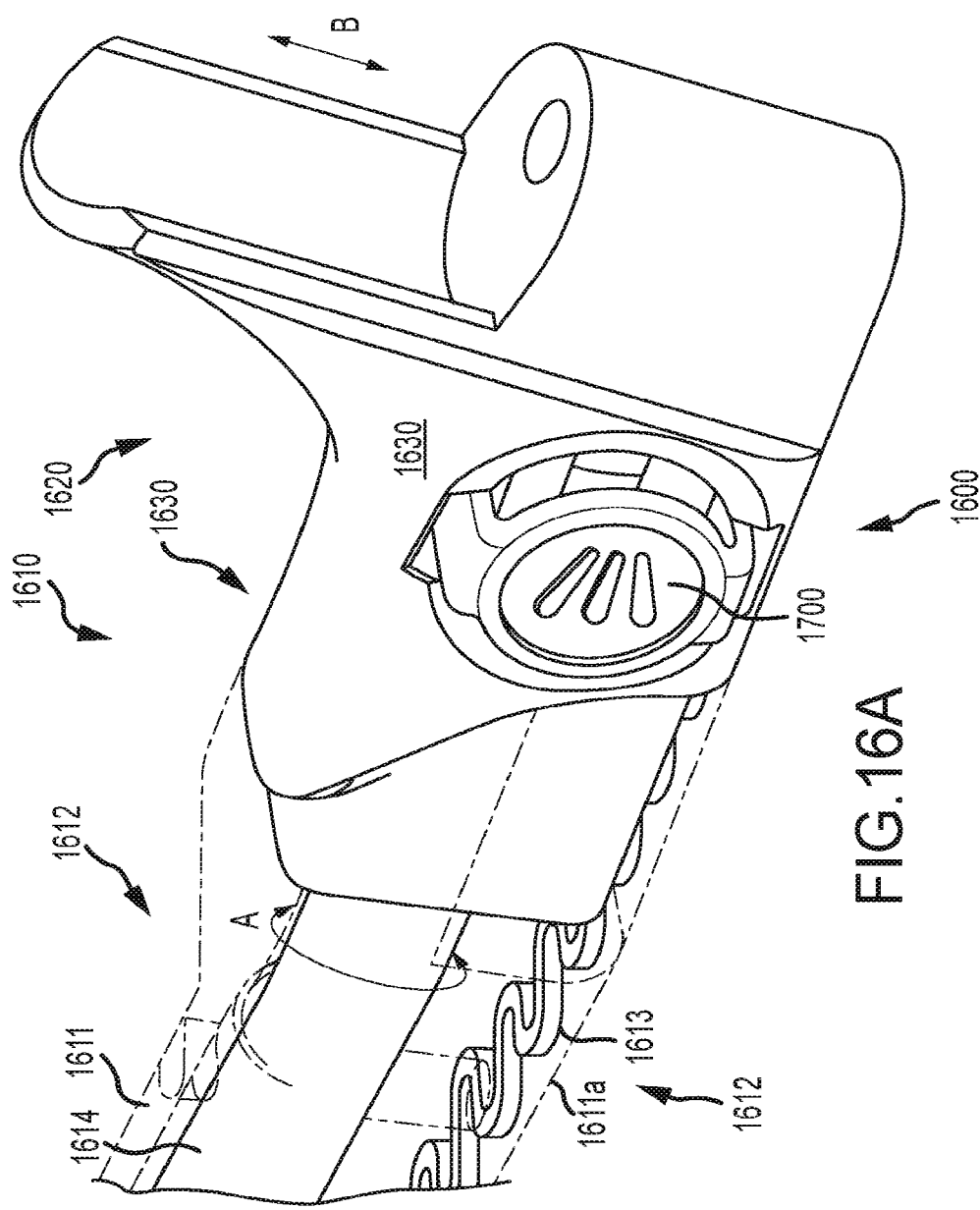
FIGS. 16A to 16S illustrate aspects of treatment systems and methods according to embodiments of the present invention.

In some embodiments, the end plugs can have either a cross hole or end hole through them or it, for example on the bottom jaw, for a suture or surgical tape to pass through providing a tension member for introduction that would help slip the bottom jaw into place without snagging tissue or vessels. The lower jaw can be the one not seen during insertion and it can be of help to surgeons if they knew that it would be guided into place automatically. For example, the tension member can be made slippery/atraumatic by sliding a rubber or polymer tube over it and clamping the distal end. An introducer system can be adapted for use with the clamp, including the use of a magnetic tipped introducer. Additionally the introducer tube or tape can be fitted with a distal pocket so that it can be placed with a straight or malleable or curved or curvable tipped instrument, which can also be used as a tissue dissector. In some embodiments, the clamp can include or be used with an introducer that is attached without means of detachment other than cutting it off with scissors or knife. If it is chosen to be cut, the tension member can stop functioning and the pieces can be removed and discarded at any time before, during, or after surgery.
Frame Button Embodiments Embodiments further encompass systems wherein the operator can push or activate a button or switch that rotates the jawbones. For example, a system can be configured so that the jaws will rotate 90° in one direction per push or "click" of the button. The surgeon can click the button in the jaw base until the jawbone is aligned as he or she desires. Hence, these embodiments provide a one-handed, intuitive operation to position the jawbone. Frame button configurations as described in relation to FIGS. 16A-16S provide an illustrative example of such embodiments. It is understood that although FIGS. 16A-16S do not show complete details of an entire adjustable clamp system, the embodiments depicted in FIGS. 16A-16S may include structural aspects or elements of other adjustable clamp system embodiments disclosed herein.

FIG. 16A depicts aspects of an adjustable clamp system 1600 according to embodiments of the present invention. Clamp system 1600 includes a clamp assembly 1610 coupled with or in operative association with a base assembly 1620. Clamp assembly 1610 has a first jaw mechanism 1612 and a second jaw mechanism (not shown), and base assembly 1620 has a first base mechanism 1630 and a second base mechanism (not shown). Clamping procedures involving relative translation between the base mechanisms and jaw mechanisms are similar to those described herein with reference to FIG. 9A, for example, and are not described in detail here to avoid prolixity. Further, each of the first and second jaw mechanisms may include a flexible boot coupled with a flexible ablation member, and optionally an end plug mechanism. For example, first jaw mechanism 1612 may include a flexible boot 1611 coupled with a flexible ablation member 1613 and an end plug mechanism (not shown). Boot 1611 may include or present an electrode mounting surface 1611a. According to exemplary embodiments, each of the jaw mechanisms may include a jawbone mechanism disposed at least partially within the flexible boot. For example, jaw mechanism 1612 may include a jawbone mechanism 1614 disposed at least partially within boot 1611. Such jawbone mechanisms may be configured to rotate or revolve within or relative to the respective boots, for example. Further, such jawbone mechanisms may be configured to rotate or revolve within or relative to the respective base mechanisms, for example. In some cases, the jawbones or jawbone mechanisms may rotate within the boots, while flexible electrode mounting surfaces of the boots remaining facing one another, or toward the tissue which is being ablated by the treatment system. As further discussed elsewhere herein, jawbone mechanisms can be alternately rotated or fixed manually by depressing or actuating a frame button mechanism 1700.

Figure 16B:
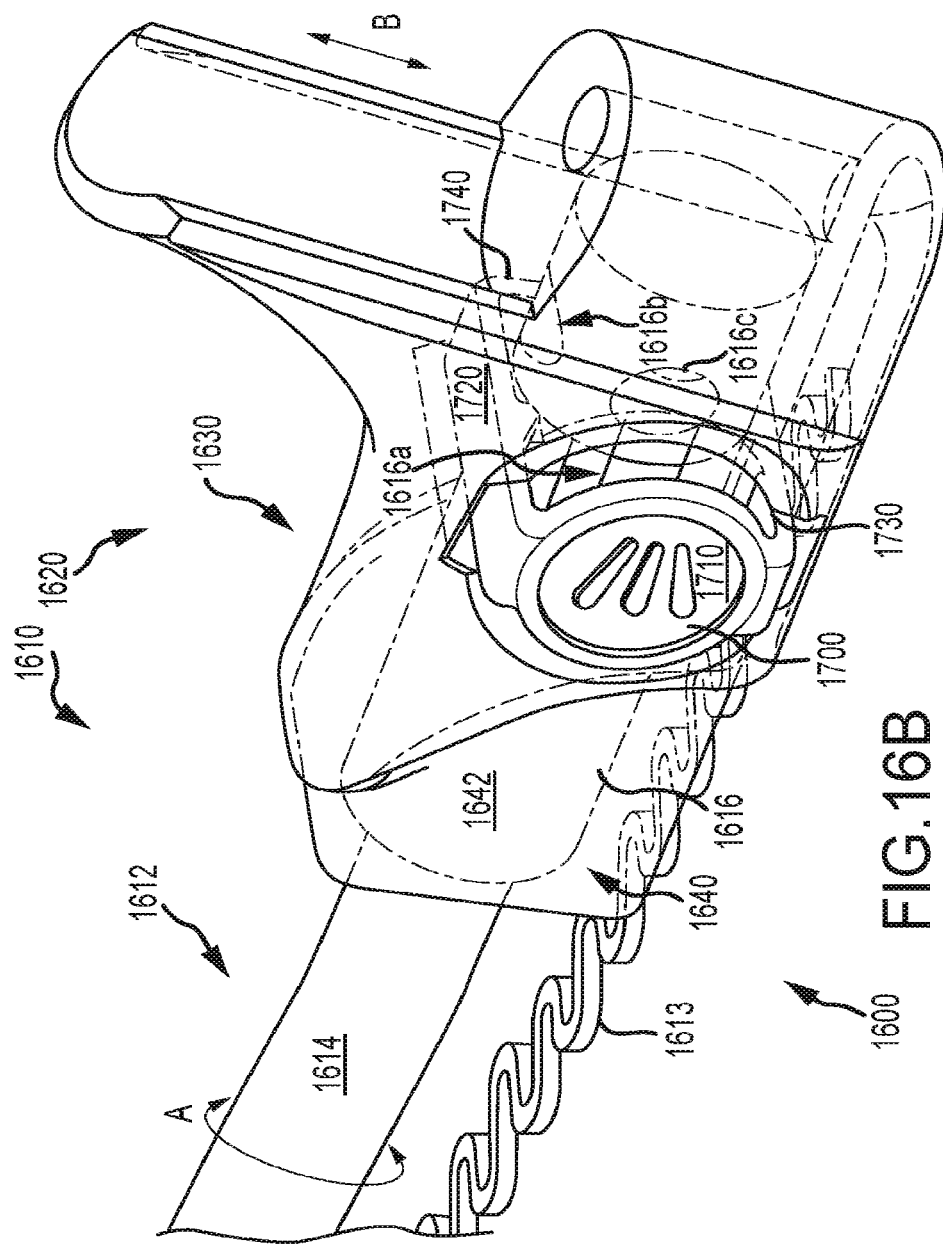

FIG. 16B depicts aspects of an adjustable clamp system 1600 according to embodiments of the present invention. FIG. 16B provides a more transparent view of aspects of system 1600, and does not show the flexible boot, as compared with FIG. 16A. Clamp system 1600 includes a clamp assembly 1610 coupled with or in operative association with a base assembly 1620. Clamp assembly 1610 has a first jaw mechanism 1612 and a second jaw mechanism (not shown), and base assembly 1620 has a first base mechanism 1630 and a second base mechanism (not shown). Each of the first and second jaw mechanisms may include a flexible boot coupled with a flexible ablation member, and optionally an end plug mechanism. For example, first jaw mechanism 1612 may include a flexible boot (not shown) coupled with a flexible ablation member 1613 and an end plug mechanism (not shown). Jaw mechanism 1612 may include a jawbone mechanism 1614 configured to rotate or revolve within or relative to the boot, for example. Further, such jawbone mechanisms may be configured to rotate or revolve within or relative to the respective base mechanisms, for example. In some cases, the jawbones or jawbone mechanisms may rotate within the boots, while flexible electrode mounting surfaces of the boots remaining facing one another, or toward the tissue which is being ablated by the treatment system. As further discussed elsewhere herein, jawbone mechanisms can be alternately rotated or fixed manually by depressing or actuating a frame button mechanism 1700.

Jaw mechanism 1612 can be adjustably coupled with base mechanism 1630, optionally via a rotational assembly 1640. In some embodiments, one or more elements of rotational assembly 1640 are part of or integral to base mechanism 1630. In some embodiments, one or more elements of rotational assembly 1640 are part of or integral to jaw mechanism 1612. Jaw mechanism 1612 includes an internal jawbone 1614 that can rotate within a flexible boot. The flexible boot can be coupled with base mechanism 1630. Hence, internal jawbone 1614 can rotate relative to base mechanism 1630, while the boot and base mechanism 1630 remain rotationally stationary with regard to one another. As shown here, rotational assembly 1640, base mechanism 1630, or jaw mechanism 1612 may include a jawbone collar 1642. Jawbone 1614 may adjustably revolve relative to base mechanism 1630 and boot 1611, as indicated by arrow A. For instance, an operator may rotate the jawbone without rotating the boot or electrode, by actuating frame button 1700. As further discussed elsewhere herein, a single actuation or push-and-release of button 1700 can cause jawbone 1614 to rotate 90 degrees. Two actuations or push-and-release cycles of button 1700 can cause jawbone to rotate 180 degrees, for example from a left curve configuration to a right curve configuration, or from a right curve configuration to a left curve configuration.

First jaw mechanism 1612 and first base mechanism 1630 can move in the upward and downward directions, relative to an elongate shaft (not shown) to which the base mechanism is slidably coupled, as indicated by arrow B. Although many of the features depicted in FIGS. 16A-16S may be discussed in terms of a first or upper clamp assembly 1610, it is understood that such features can also be incorporated into a second or lower clamp assembly of clamp system 1600. As viewed through the transparently illustrated base mechanism 1630, it can be seen that button 1700, which extends through jaw base mechanism 1630, includes a vertical engagement pad 1710, an upper horizontal arm 1720, a lower horizontal arm 1730, and a vertical arm 1740. Jawbone mechanism 1614 may include a jawbone base 1616 that can rotate within an inner bearing surface of jawbone collar 1642. As shown here, jawbone base 1616 is encircled by frame button 1700, and includes a set of gear teeth or indentations 1616a that are adapted to receive teeth of the frame button. Jawbone base 1616 also includes a first aperture 1616b, and a second aperture 1616c that intersects first aperture 1616b. These apertures can operate to engage with a leaf spring, as described elsewhere herein.

FIG. 16C shows an opposing side of first base mechanism 1630. Boot 1611 is depicted transparently, so that jawbone 1614 can be seen. Base assembly 1620 includes a leaf spring mechanism 1622 attached with jaw base 1630 via an attachment point 1621. The outer surfaces of the leaf spring mechanism and the nearby jaw base are flush, thus providing a narrow or thin profile. Leaf spring mechanism 1622 is shown here in an inward configuration, such that it fits within a horizontal groove 1631 of base mechanism 1630 and contacts vertical arm 1740 of the frame button. Accordingly, upward and downward movement of spring mechanism 1622 as indicated by arrow A is inhibited or prevented. In use, when the operator presses on the vertical engagement pad of the frame button, the vertical arm of the button extends through vertical groove 1633 of base 1630, and presses against leaf spring 1622. In this way, the button actuation causes the proximal outer surface of the leaf spring to protrude out of base mechanism groove 1631, while the distal section of the spring remains tight against base mechanism 1630 due to the connection at attachment point 1621. It is helpful for the operator to not press or hold leaf spring against base mechanism 1630 when actuating the button engagement pad, so as to allow leaf spring to flex away from apertures 1616b and 1616c, as described elsewhere herein. Hence, the operator's opposing finger can be placed on the base mechanism 1630 or boot 1611 during the button actuation.

FIG. 16D shows an alternative construction for the jaw base, as compared with FIG. 16C. As depicted in FIG. 16D, jaw base 1630' includes a protrusion or prominence 1634'. Hence, the proximal outer surface of the spring mechanism is set back from the outer surface of the nearby jaw base. Accordingly, during use, the operator may place the opposing finger on prominence 1634' when pressing against the engagement pad of the frame button. The deeper grooves 1631' and 1633' allow the vertical arm of the frame button, as well as the proximal section of the leaf spring 1622', to extend outward radially when the button is pushed, while the operator's actuating finger and opposing finger are located directly opposite one another on the jaw base 1630'. Hence, the leaf spring is buried in the bulging counter-button shape or prominence so that the leaf spring remains within the solid base envelope when flexed. The opposing finger can be placed on the counter-button shape to directly oppose the force applied by the actuating finger. The raised protuberance 1634' resembles a circular bump on the side of jaw base 1630' opposite the frame button engagement pad. This configuration allows the operator to apply a squeezing force on both sides of the jaw base with opposing fingers, pressing in against both sides. The presence of deeper grooves 1631' and 1633' prevent the operator's finger from limiting movement or flexion of leaf spring 1622' during the squeezing motion, thus accommodating a full range of motion for the frame button when pressed. Hence, the raised boss 1634' facilitates unrestricted flexing of the leaf spring and movement of the frame button.

Figure 16E:
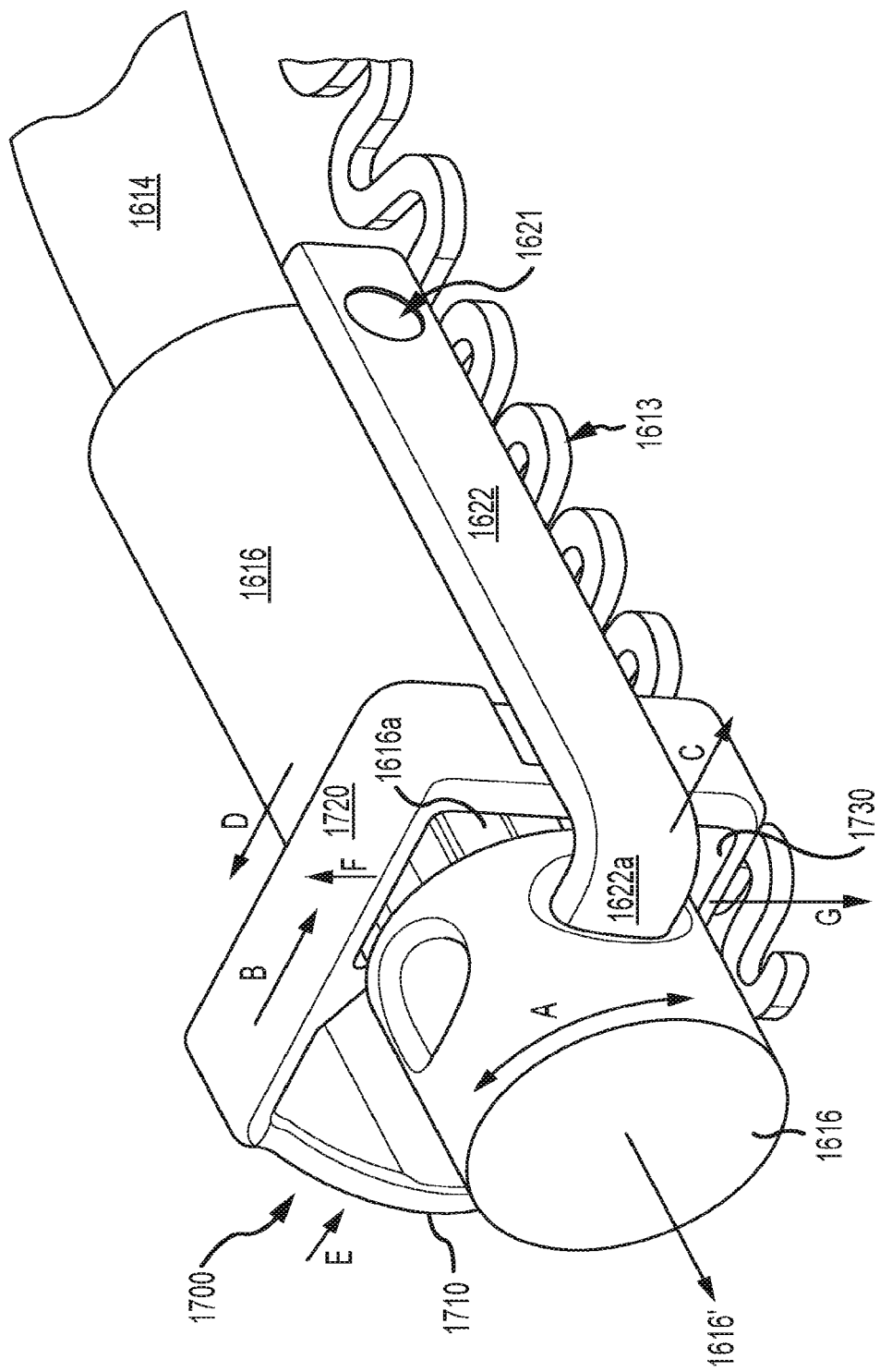

FIG. 16E shows aspects of the interaction between frame button 1700, leaf spring mechanism 1622, and jawbone base 1616 according to embodiments of the present invention. Leaf spring 1622 has a proximal section that includes a curved or hooked end 1622a that can engage apertures 1616b, 1616c of jawbone base 1616. When the leaf spring is on the relaxed or unflexed configuration, such as when it is not being pushed outward by the frame button, the tab 1622a is engaged with the jawbone base apertures, thus preventing or inhibiting the jawbone base from rotating about a longitudinal jawbone base axis 1616' as indicated by arrow A. In some instance, the proximal section of leaf spring 1622 is biased to press radially inward toward apertures 1616b, 1616c. Optionally, the leaf spring mechanism can be configured as a straight bar with no bias. Leaf spring mechanism 1622 can operate to constrain the rotation of jawbone base 1616. As noted elsewhere herein, leaf spring 1622 can be situated within a groove of the jaw base (not shown) when the leaf spring is in the unflexed configuration, thus preventing upward and downward movement of the leaf spring, which further constrains rotational movement of the jawbone base. Leaf spring mechanism 1622 includes a distal portion that is attached with the jaw base (not shown) at an anchor point 1621. This attachment point may include a spot weld, a screw, a pin, or the like. During use, the operator presses against engagement pad 1710 of button 1700, thus moving button 1700 in the direction indicated by arrow B. Accordingly, vertical arm 1740 of the frame button presses against the leaf spring mechanism, thus moving tab 1622a out of aperture 1616c in the direction indicated by arrow C, as the leaf spring pivots about attachment point 1621. The leaf spring may present some amount of resistance to this button movement, as the spring bends or flexes in this hinged manner. However, the force applied by the user's finger overcomes the leaf spring resistance. In this way, actuation of button 1700 can allow jawbone base 1616 to rotate in the direction indicated by arrow A. As further described elsewhere herein, in addition to allowing jawbone base rotation, actuation of button 1700 also forces rotation of the jawbone base due to engagement between teeth or pawl of the frame button and teeth or indentations of the jawbone base. When the finger pressure is released, the leaf spring returns toward an unflexed configuration, thus moving the button in the direction indicated by arrow D. It is also noted that the horizontal arms of the button may flex slightly during actuation. For example, when force is applied against engagement pad in the direction indicated by arrow E, a central portion of upper horizontal arm 1720 may flex upwardly in the direction indicated by arrow F. Similarly, when force is applied against engagement pad in the direction indicated by arrow E, a central portion of lower horizontal arm 1730 may flex downwardly in the direction indicated by arrow G. As further described elsewhere herein, such flex is directly caused by the back side of frame button engagement tooth, which is shaped like a ramp, as the tooth is forced backward over a jawbone base tooth. The flex allows the frame button tooth to ratchet into a new engagement position, for example from a position between jawbone base teeth 1616a(8) and 1616a(1) as shown in FIG. 16L, to a position between teeth 1616a(1) and 1616a(2) as shown in FIG. 16O, and to a position between teeth 1616a(2) and 1616a(3) as shown in FIG. 16P. Hence, the force applied to the button pad by the operator acts as an indirect cause, and the ramping force conferred by the jawbone base tooth acts as a direct cause, for the flexing of the horizontal button frame arm. Jawbone base 1616 includes grooves or indents 1616a that are adapted to engage teeth of the frame button. In some embodiments, jawbone base 1616 is constructed of a single piece of metal or other suitable material. In some instances, jawbone base 1616 may be machined or metal injection molded.

Figure 16F:
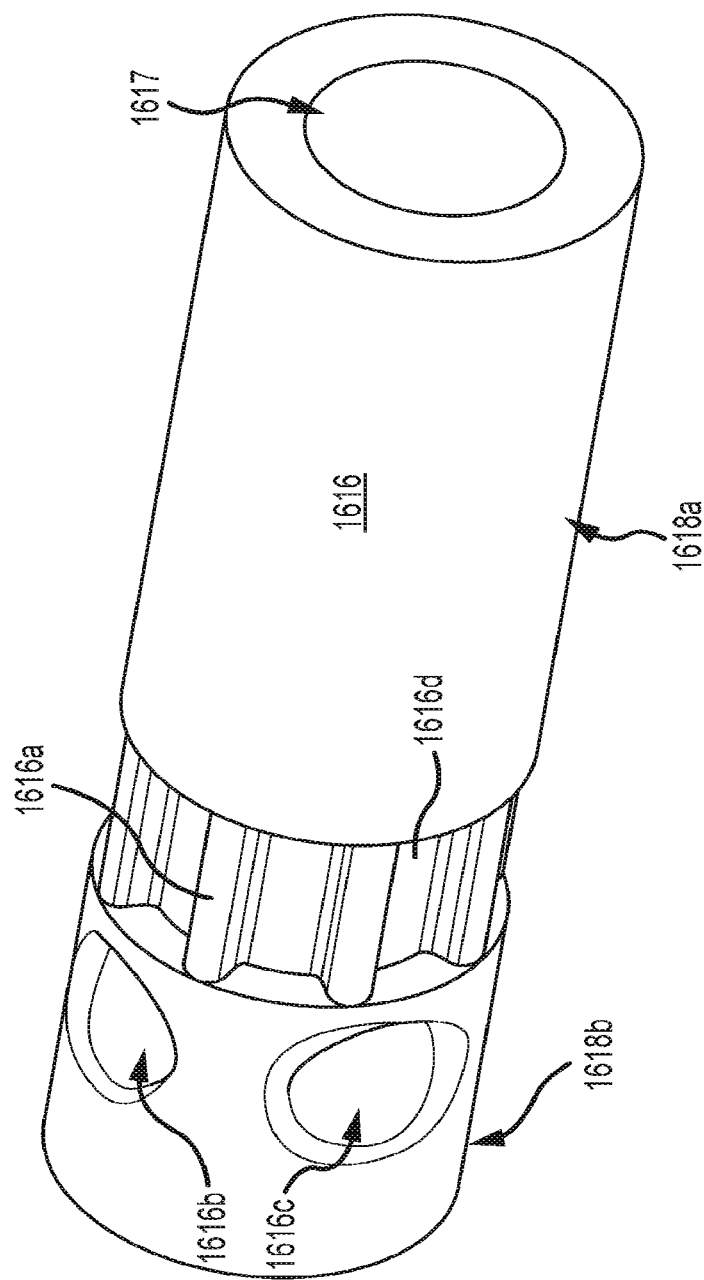

FIG. 16F shows aspects of jawbone base 1616 according to embodiments of the present invention. Jawbone base 1616 includes or defines an inner lumen or cylindrical passage 1617, which operates as a socket that receives a proximal section of a jawbone (not shown). Jawbone base 1616 also includes or defines distal and proximal outer rotary bearing surfaces 1618a, 1618b, that engage or are received within a corresponding inner bearing surface of a jaw base (not shown). As depicted here, jawbone base 1616 includes one or more jawbone base ratchet teeth 1616a, which may be formed by cutting or creating one or more indents or recesses 1616d in the body of the jawbone base. These grooves 1616d, which may be integral to and disposed annularly about the jawbone base, can be configured to engage teeth or pawls of a frame button (not shown). Jawbone base 1616 also includes leaf spring tooth engagement holes 1616*b*, 1616*c*, which may be located circumferentially about the jawbone base, for example so as to provide engagement locations at 90 degree intervals. Engagement holes can be constructed by drilling or forming two or more intersecting cylinders or bores through the body of the jawbone base.

Figure 16G:
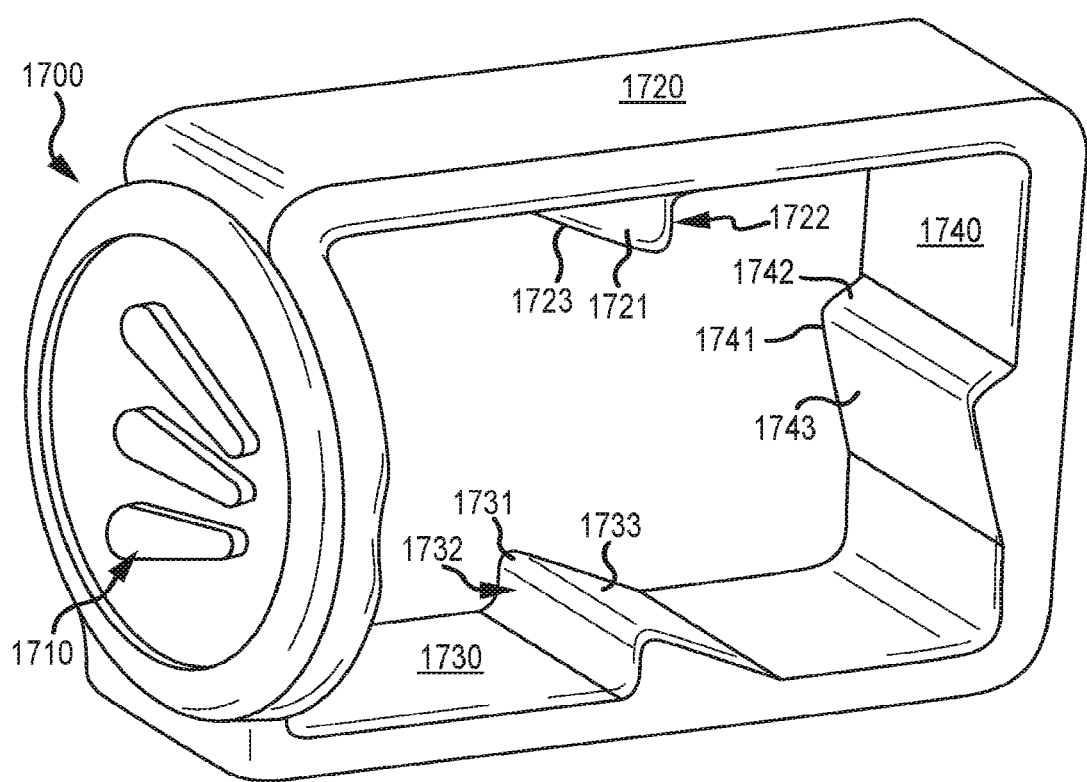
Figure 16H:
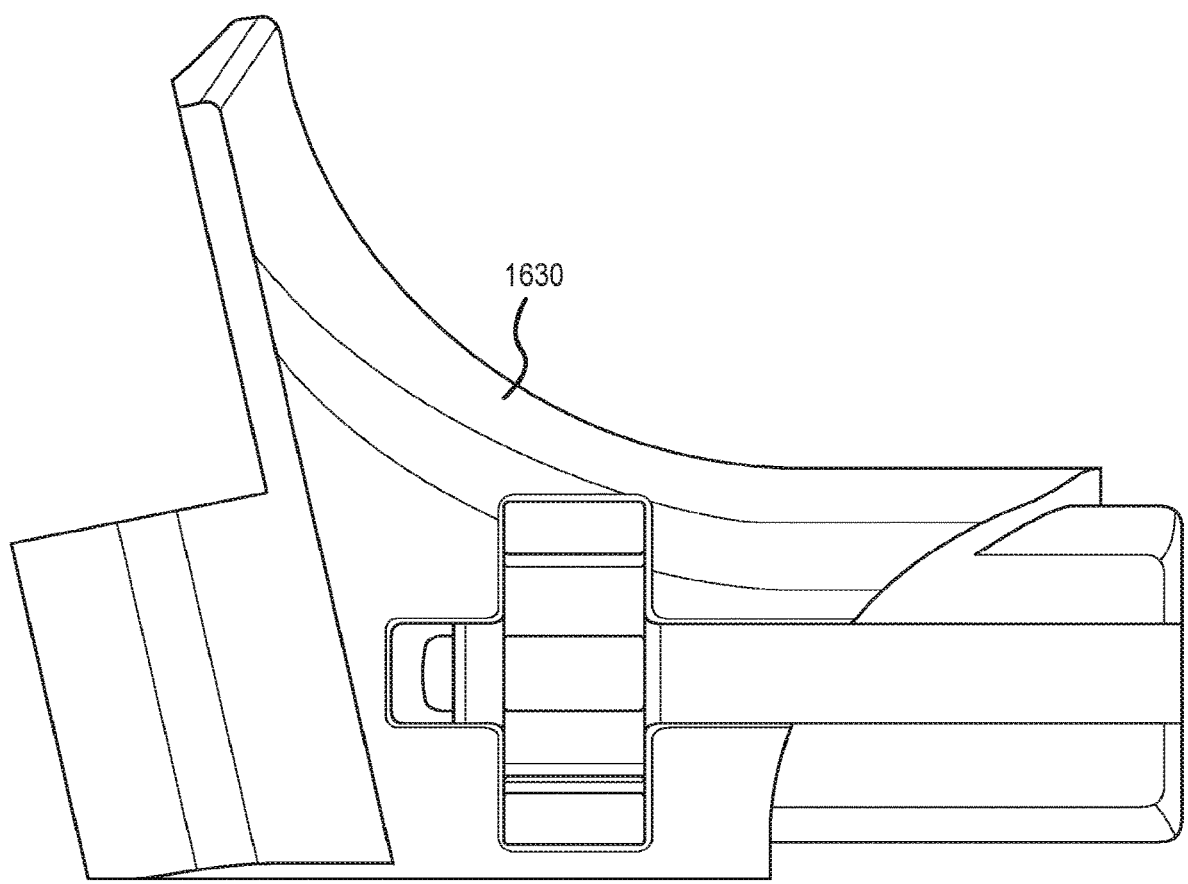
Figure 16I:
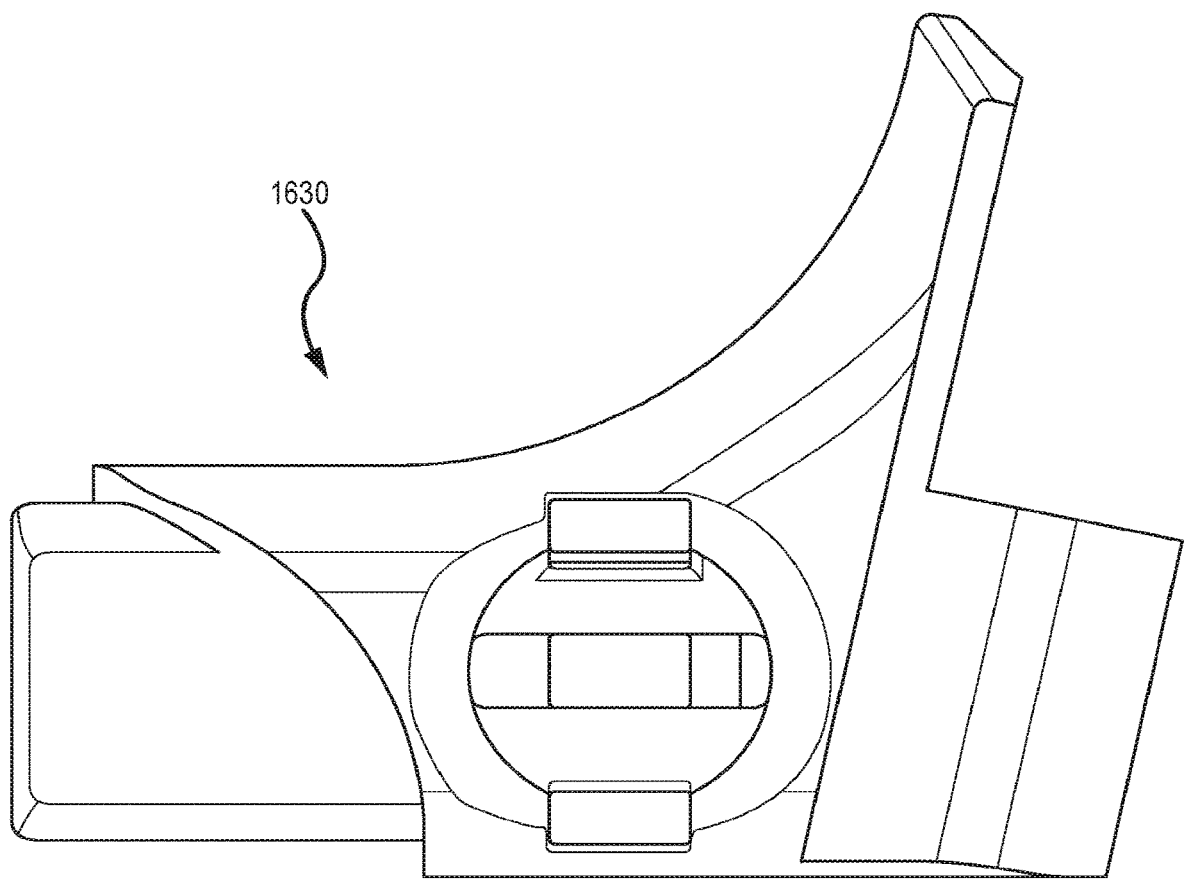
Figure 16J:
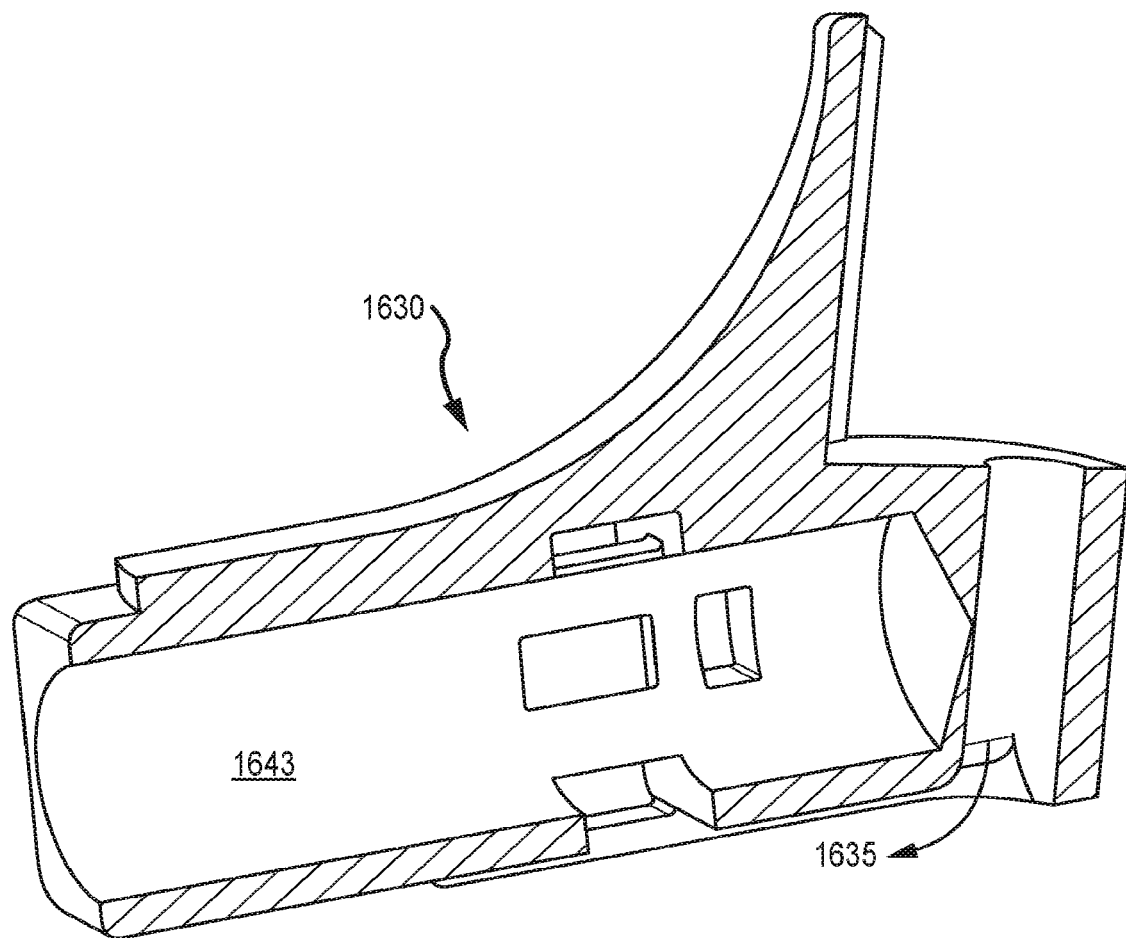
Figure 16K:
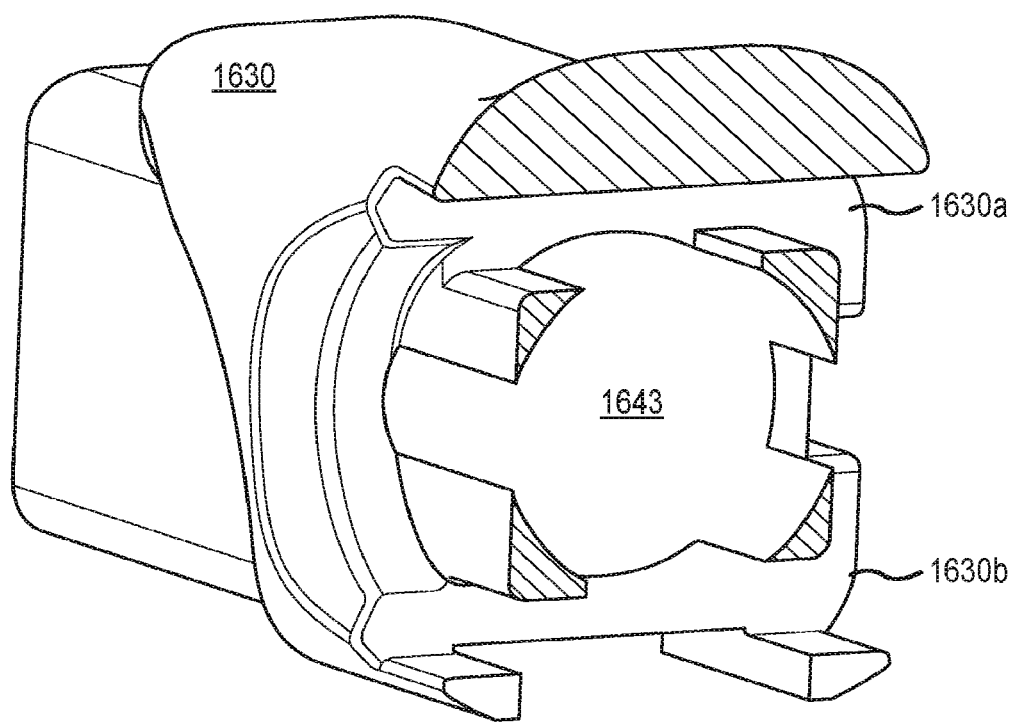

FIG. 16G illustrates aspects of a frame button 1700 according to embodiments of the present invention. As shown here, button 1700 includes an engagement pad 1710, an upper arm 1720 having an upper arm tooth 1721, a lower arm 1730 having a lower arm tooth 1731, and a vertical arm 1740 having a vertical arm tooth 1741. Upper and lower arms 1720, 1730 are configured to flex or bend during actuation of the frame button. The engagement pad can be circular in shape, and approximately the diameter of a ballpoint pen cap. As shown here, upper and lower teeth 1721, 1731 have opposing engagement faces 1722, 1732, respectively, which operate as drivers for urging the jawbone base (not shown) in a rotary manner. Vertical arm tooth 1741 may be shaped slightly different from the upper and lower teeth, and may operate as a stop for the jawbone base during actuation of the frame button. For example, as described elsewhere herein, when reaching the end of a throw movement or button stroke actuation, vertical tooth 1741 can engage a jawbone base tooth, thus stopping motion of the jawbone base in a precise orientation so that the leaf spring can engage with a leaf spring engagement hole of the jawbone base. As shown here, upper tooth 1721 includes an engagement face 1722 and an engagement ramp 1723. Lower tooth 1731 includes an engagement face 1732 and an engagement ramp 1733. Vertical tooth 1741 includes an upper engagement face 1742, that is angled, and a lower engagement ramp 1743. In use, ramps such as upper tooth engagement ramp 1723 and lower tooth engagement ramp 1733 can operate to slide over a jawbone base tooth when moving in a non-engaged direction.

Figure 16L:
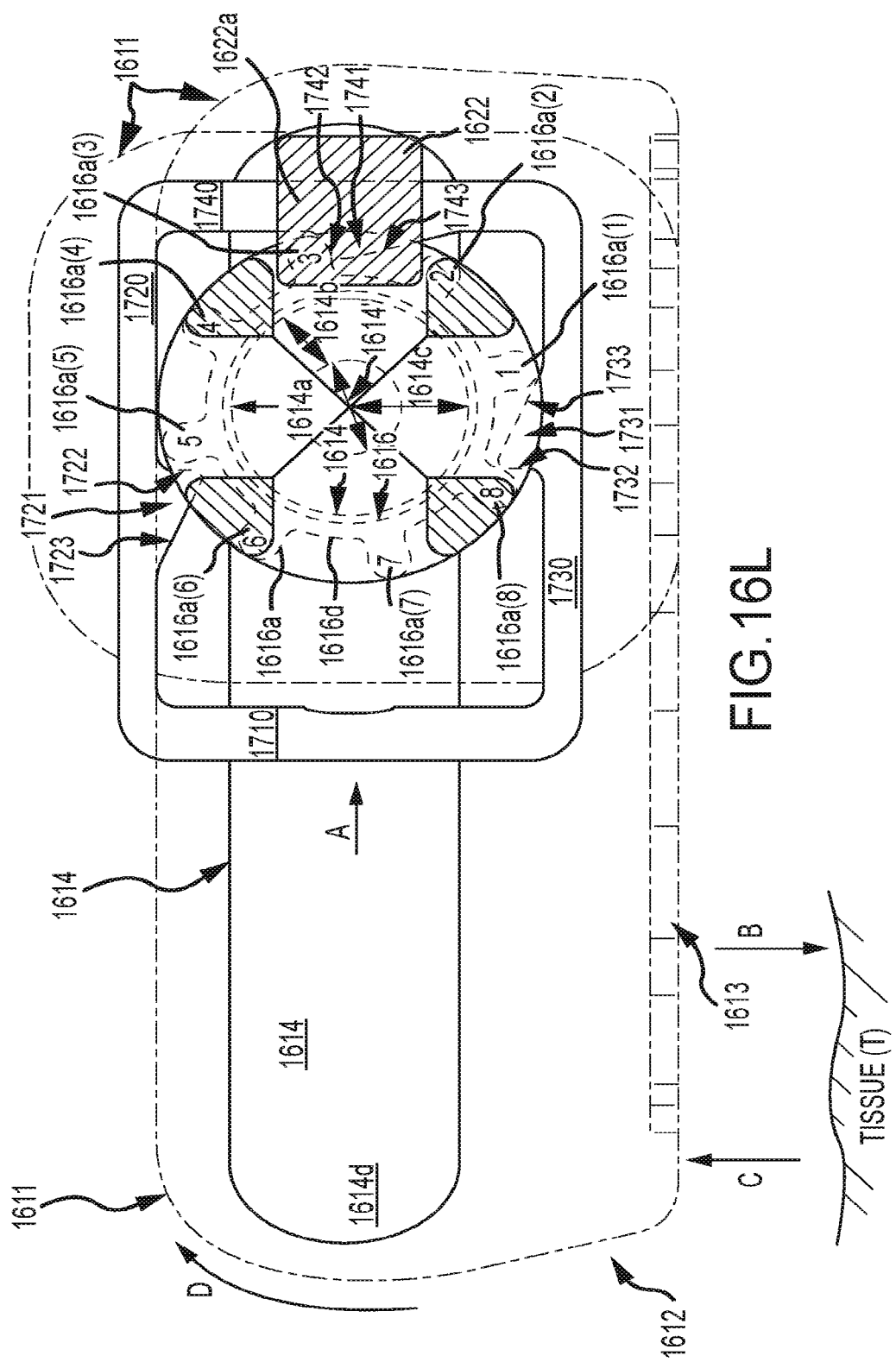
Figure 16M:
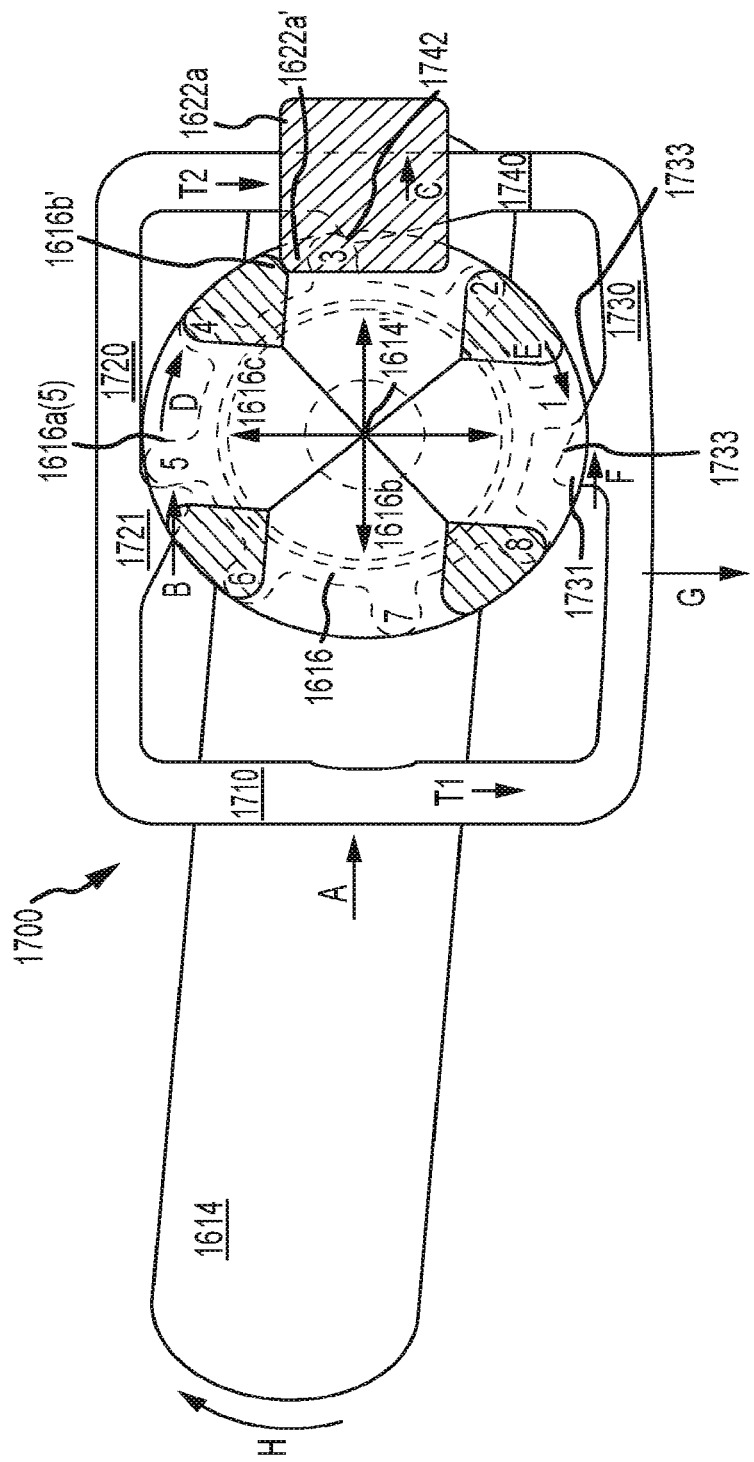
Figure 16N:
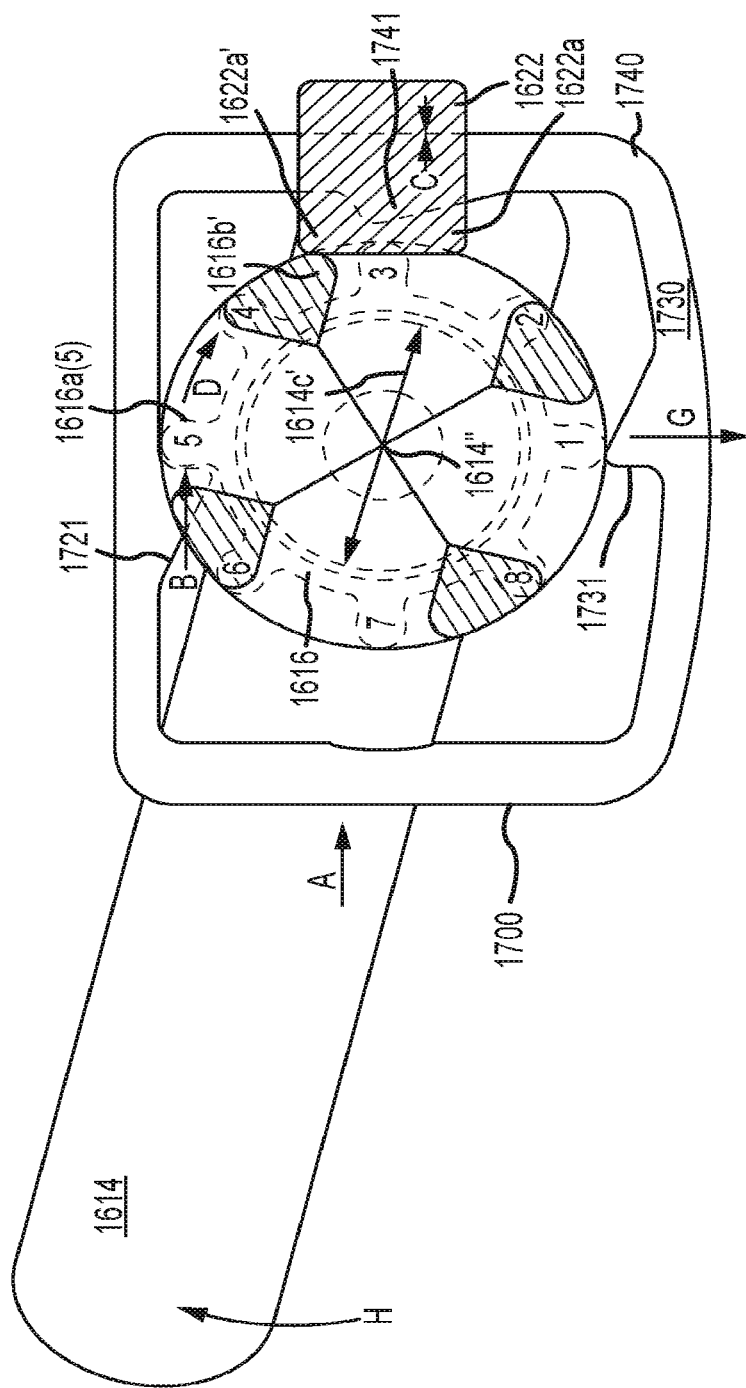
Figure 16O:
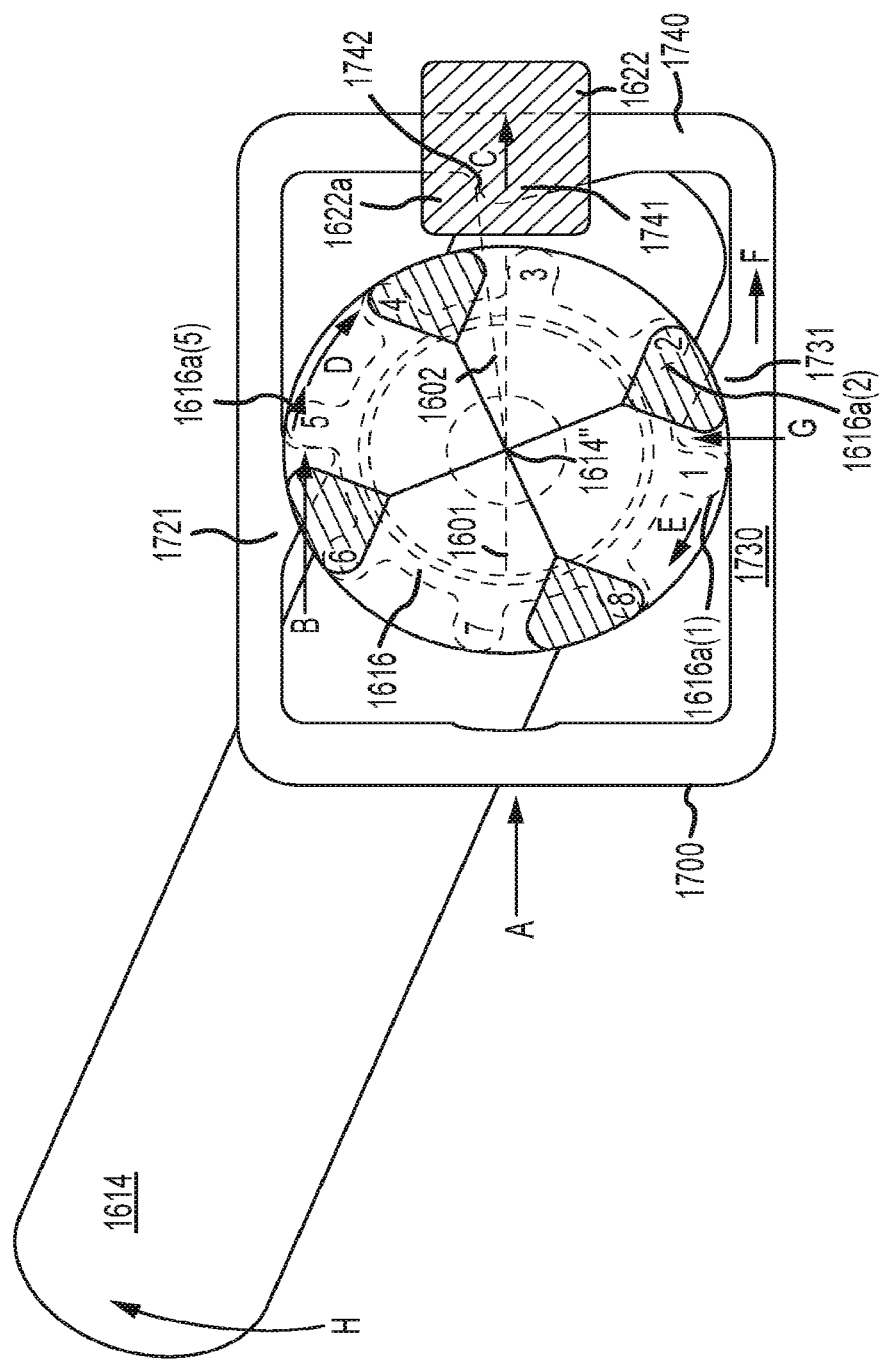
Figure 16P:
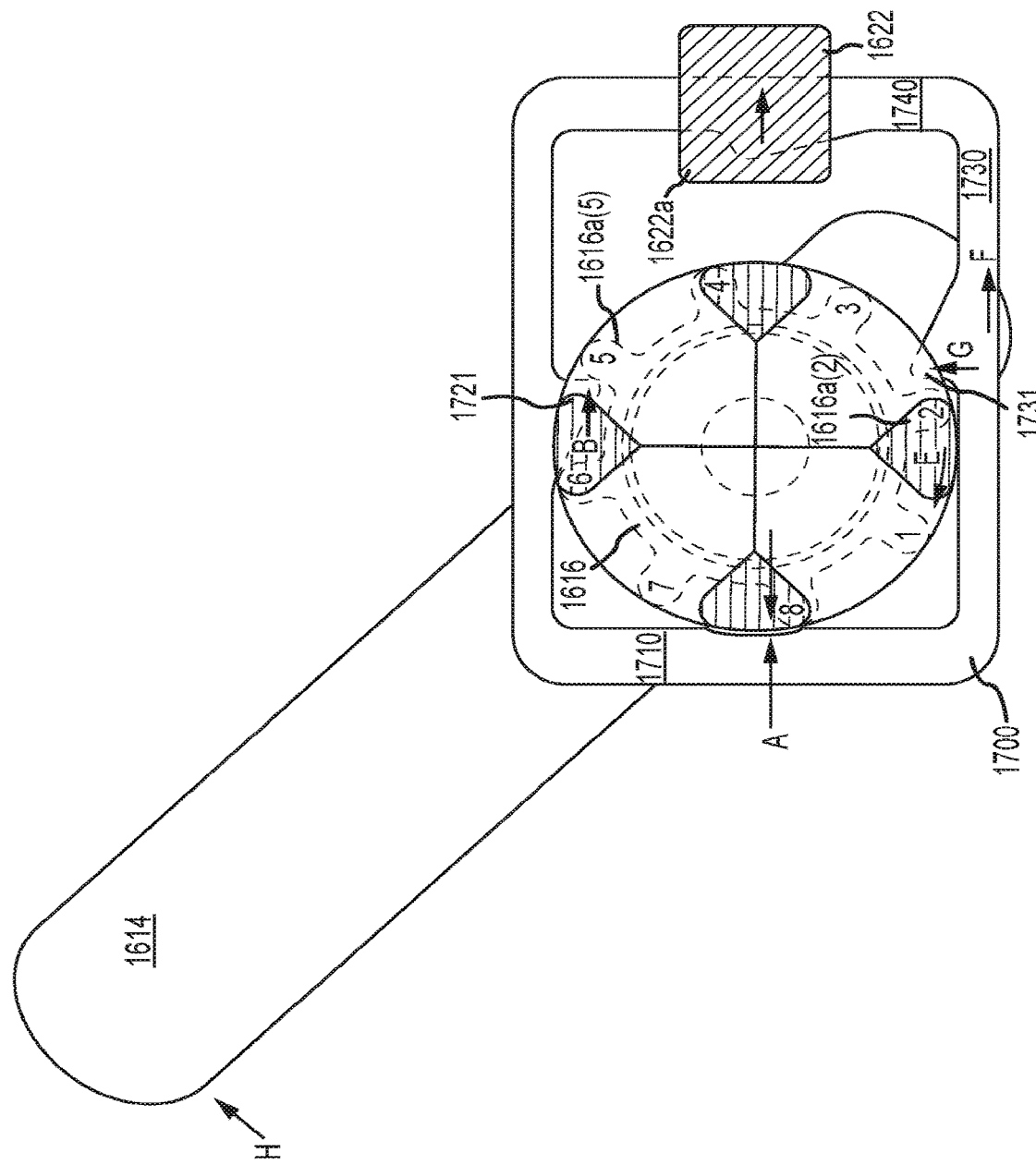
Figure 16Q:
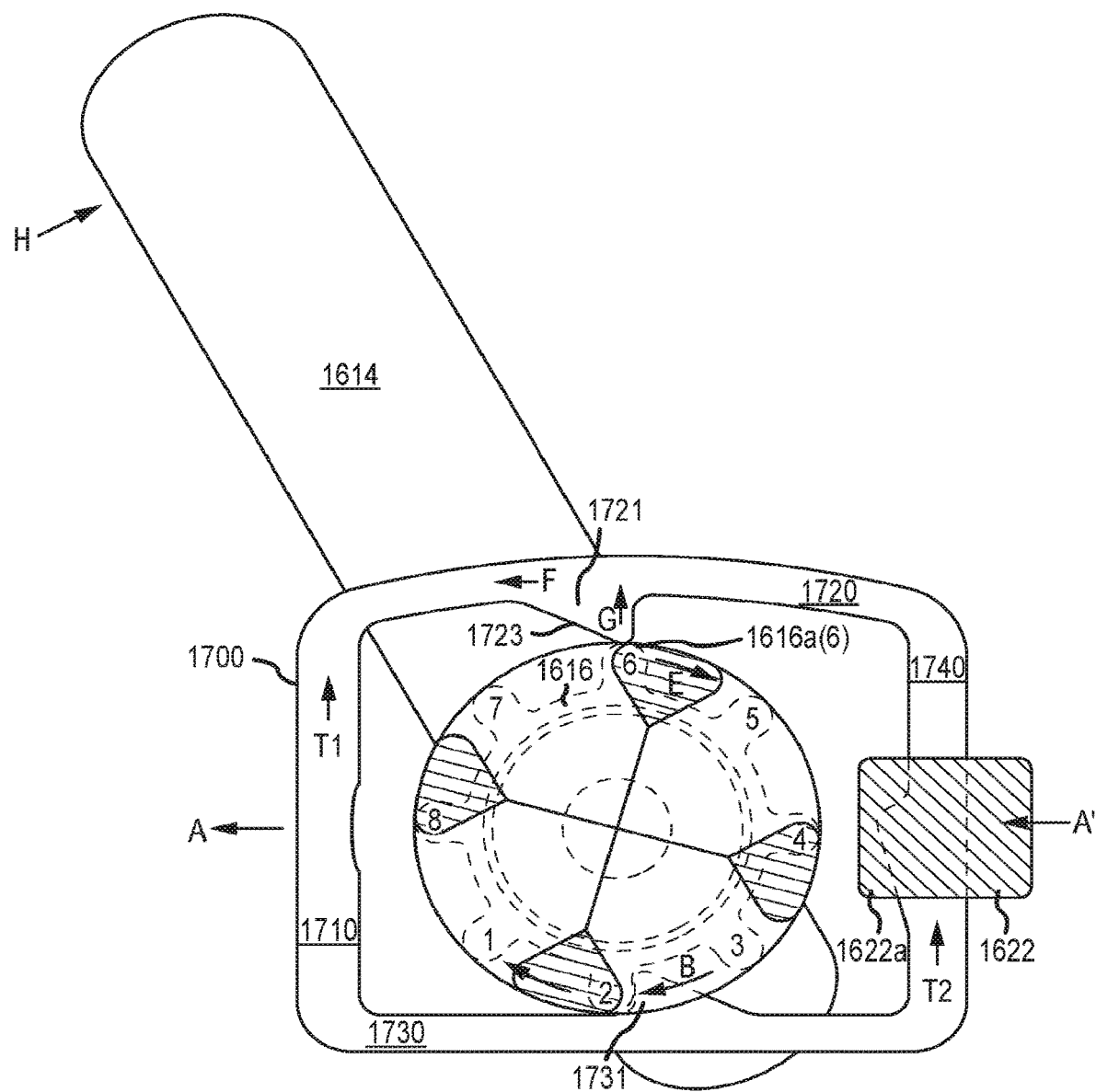
Figure 16R:
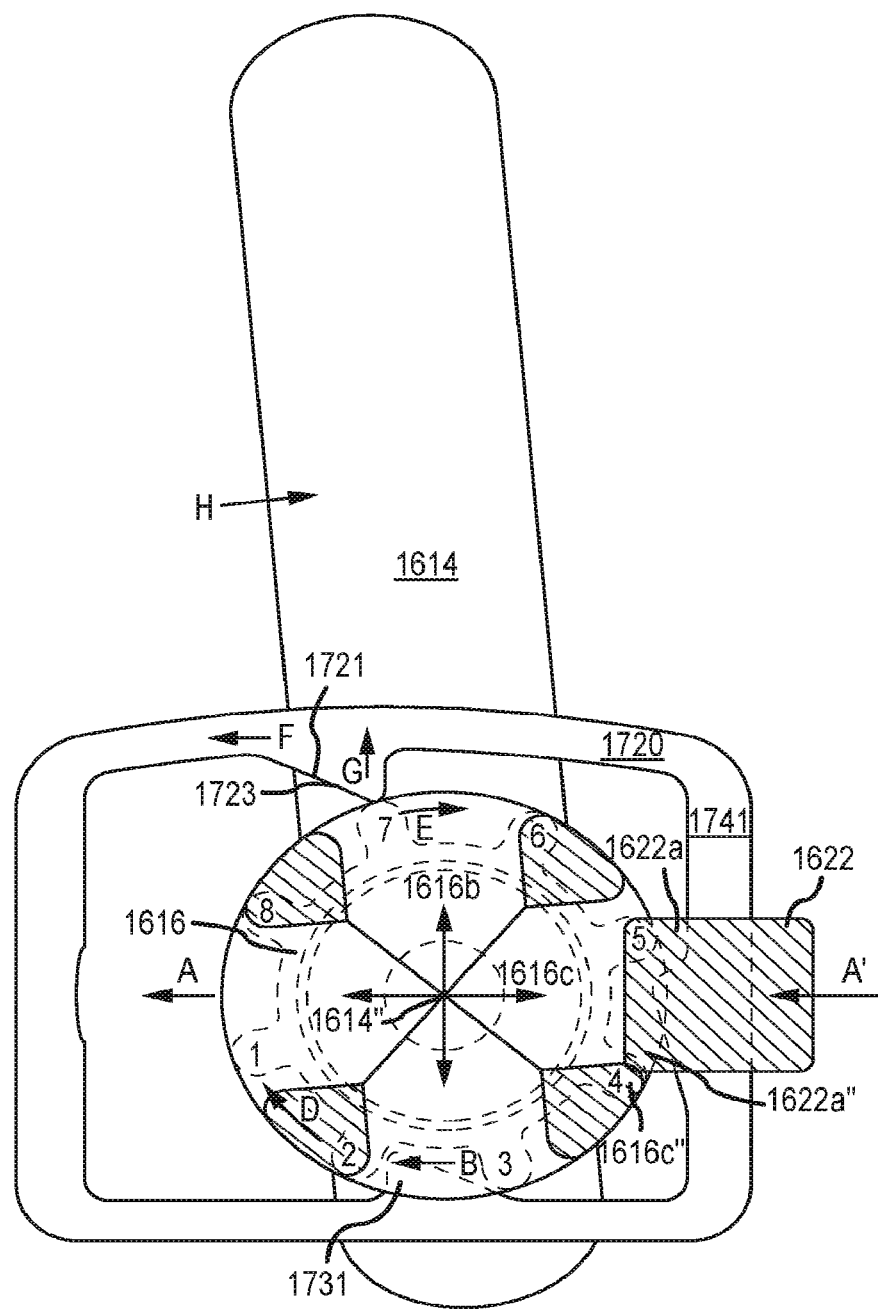
Figure 16S:
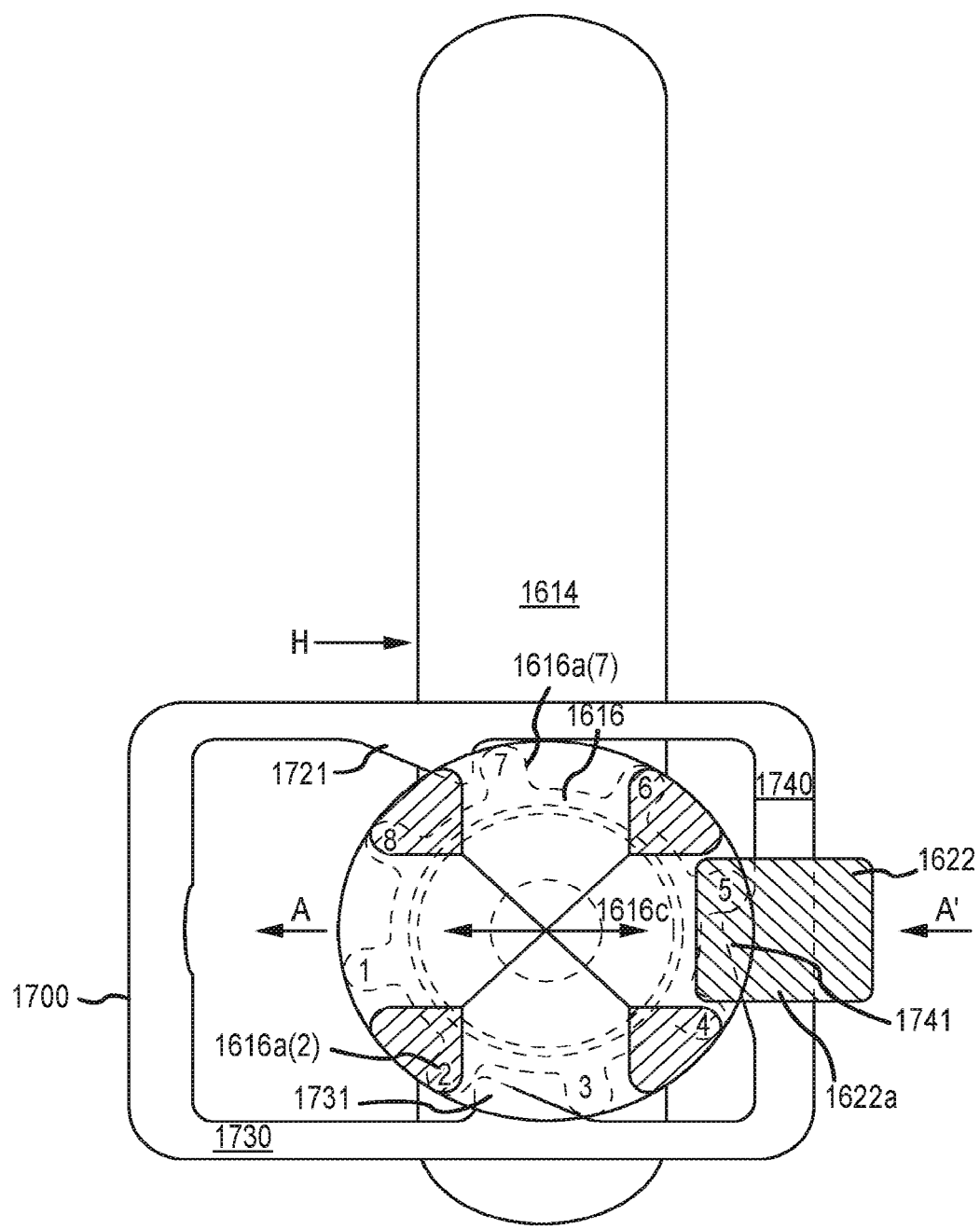

Upper engagement face 1742 provides an angled face that operates to act as an engagement point, for example as shown in FIGS. 16L, 16M, and 16S, with a jawbone base tooth. With reference to FIG. 16O, upper engagement face 1742 can provide an angled surface that engages a jawbone base tooth at a contact location disposed above a horizontal line 1601 that extends from a jawbone center of rotation 1614" to tooth 1741. To maintain parallel engagement with the jawbone base tooth, upper engagement face 1742 can be angled such that an extension of a plane 1602 of its face can cross through or intersect the center of rotation of the jawbone base 1614". In this way, upper engagement face 1742 may be radially lined up with jawbone base center 1614".

FIG. 16H illustrates aspects of a jaw base 1630 according to embodiments of the present invention. FIG. 16I shows a side view of jaw base 1630 opposing that of the view depicted in FIG. 16H. FIG. 16J shows a cross-section view of jaw base 1630 sectioned lengthwise. Jaw base 1630 includes a bore or inner bearing surface 1643 that can engage outer rotary bearing surfaces of a jawbone base (not shown). A good fit between the inner jaw base bore and the outer jawbone base bearing surface allows the jawbone base to rotate within the jaw base with minimal or no axial or translational wiggle or slop. FIG. 16K shows a cross-section view of jaw base 1630 sectioned crosswise. Each of FIGS. 16H to 16K illustrate cutouts or apertures in the jaw base which receive various systems components, such as the frame button, the leaf spring tab, and the like. For example, jaw base 1630 includes an upper track 1630*a* that slidingly receives an upper horizontal arm of a frame button, and a lower track 1630*b* that slidingly receives a lower horizontal arm of a frame button. As shown in FIG. 16J, jaw base 1630 may include a wire passage or track 1635 that receives a wire for delivering energy to an ablation electrode. In some cases, wires extend through a shaft in the treatment device, for delivering energy or electrical signals between an ESU and various jaw components such as a jaw electrode. Jaw base 1630 is well suited for fabrication by metal injection molding (MIM).

FIGS. 16L to 16S illustrate how a single push-and-release actuation of the frame button can rotate the jawbone by 90 degrees. That is, a push motion to move the button from an outward position to an inward position operates to rotate the jawbone by 45 degrees, and a release motion to allow the button to move from the inward position to the outward position operates to rotate the jawbone by an additional 45 degrees, thus resulting in a sum rotation of 90 degrees. Two push-and-release actuations can therefore rotate the jawbone by 180 degrees.

As depicted in FIG. 16L, prior to actuation, engagement face 1722 of upper button arm 1720 is disposed near tooth 1616*a*(5) of the jawbone base, between teeth 1616*a*(5) and 1616*a*(6), engagement face 1732 of lower button arm 1730 is disposed near tooth 1616*a*(8), between teeth 1616*a*(8) and 1616*a*(1), and upper engagement face 1742 of vertical arm 1740 is disposed near tooth 1616*a*(3), between teeth 1616*a*(3) and 1616*a*(2). In a general sense, each of the button teeth 1721, 1731, 1741 are engaged or nearly engaged with corresponding jawbone base teeth. Relatedly, leaf spring mechanism tab 1622*a* is engaged with an engagement aperture (e.g. 1616*b*, 1616*c* as shown in FIG. 16M), thus helping to rotationally lock or restrain the jawbone base and the jawbone. As depicted in this proximal cross-sectional area of the base assembly, jawbone 1614 defines an inner bore 1614*a*, a wall thickness 1614*b*, and an outer radius 1614*c* (e.g which corresponds to an outer diameter 1614*c'* as shown in FIG. 16N). The outer surface of jawbone 1614 interfaces with the inner surface of jawbone base 1616. In some cases, the jawbone is constructed as a tubular structure having an inner bore extending therethrough. The distal portion 1614*d* of jawbone 1614 is shows sweeping toward the left side of FIG. 16L.

When using the clamp device to squeeze or clamp a section of patient tissue T, the jaw mechanism 1612 presses against tissue T in the direction indicated by arrow B. Consequently, an opposing force from patient tissue acts upon the jaw mechanism in the direction indicated by arrow C. The clamping interaction between the jaw mechanism and the patient tissue tends to rotate jawbone 1614 about an axis (e.g. 1614") in the direction indicated by arrow D, thus creating a torque or moment. Various aspects of exemplary clamp systems, such as the frame button, jawbone base, and leaf spring, can operate to resist such rotation associated with the tissue clamping torque. For example, when squeezing tissue with the clamp, a flat surface of the leaf spring tab 1622*a* can press against a flat surface of the leaf spring engagement aperture (e.g. 1616*b*, 1616*c* as shown in FIG. 16M), thus constraining rotational movement of the jawbone. Hence, aspects of the jaw base can operate to resist rotation of the jawbone during a clamping procedure. In this way, a curved parallel relationship between jawbones, guides, ablation apparatuses, electrodes, and the like can be maintained during use. The three dimensional structural relationship between the respective jawbones, guides, ablation apparatuses, electrodes can withstand forces which would otherwise cause disalignment or splay between these elements.

As shown in this transparent view from the proximal section of the base assembly, the actuation is initiated by pressing against the frame button engagement pad 1710 in the direction indicated by arrow A. As a result, engagement face 1722 of upper tooth 1721 moves toward or engages tooth 1616a(5). Further, engagement face 1732 of lower tooth 1731 moves away from or disengages tooth 1616a(8), and engagement ramp 1733 moves toward or engages tooth 1616a(1). Relatedly, upper engagement face 1742 of vertical arm tooth 1741 moves away from or disengages tooth 1616a(3). Moreover, the outer face of vertical arm 1740 moves toward or engages the inner face of leaf spring 1622.

As shown in FIG. 16M, as the operator maintains an engagement force on the frame button engagement pad, button 1700 continues to move in a direction indicated by arrow A. At this step in the actuation process, upper horizontal frame tooth 1721 operates as the primary driver to rotate jawbone 1614, by pressing against jawbone base tooth 1616a(5) in the direction indicated by arrow B. As described previously, jawbone base 1616 includes two intersecting cylinders or bores 1616b, 1616c which provide engagement holes that receive a leaf spring tab 1622a. The cross-section view of the proximal portion of the base assembly shows the intersection between these two interior cylindrical surfaces or bores. When frame button shifts in the direction indicated by arrow A, an engagement point 1622a' of tab 1622a slips along a corresponding engagement point 1616b' of jawbone base aperture 1616b, as the button vertical arm 1740 pushes against leaf spring 1622 in the direction indicated by arrow C and as the upper arm tooth 1721 pushes against jawbone base tooth 1616a(5) to rotate jawbone base 1616 about axis 1614" in the direction indicated by arrow D. Engagement points 1616b' and 1622a' just begin to clear as the frame button moves toward the right and lifts the leaf spring out of the engagement hole. Similarly, upper ramp surface 1742 of vertical frame arm 1740 begins to clear jawbone base tooth 1616a(3) as frame button moves toward the right and tooth 1616a(3) rotates in the clockwise direction. Relatedly, ramp surface 1733 of lower arm tooth 1731 and jawbone base tooth 1616a(1) slide along each other, with tooth 1616a(1) moving in the direction indicated by arrow E and tooth 1731 moving in the opposing direction indicated by arrow F. Accordingly, a central portion of lower horizontal frame arm 1730 flexes or bows downwardly in the direction indicated by arrow G. Lower frame arm 1730 curves in this manner due to the lower frame tooth ramping away from the jawbone base tooth moving in the opposite direction.

In use, as a curvature develops in one horizontal arm, the opposing parallel horizontal arm may also develop a curvature due to the tension in the vertical members. For example, as lower horizontal frame arm 1730 flexes or bows downwardly in the direction indicated by arrow G, button vertical arm 1710 and frame button vertical arm 1740 are tensioned or pulled in a downward direction as indicated by arrows T1 and T2, respectively. This tension serves to create a bow or flex (not shown) in upper horizontal member 1720, and hence upper frame member tooth 1721 then engages more firmly or with more force the jawbone base tooth (e.g 1616a(5)) located opposite to the jawbone base tooth (e.g. 1616a(1)) which is slidingly engaging ramp surface 1733.

Rotation of jawbone base 1616 leads to a corresponding rotation of jawbone 1614 as indicated by arrow H. The central axis of rotation is aligned with the jawbone axis. Hence, FIG. 16M illustrates enhanced positive engagement between the upper arm pawl tooth and ratchet tooth 1616a(5), such that movement of the frame button drives rotation of the jawbone base. The leaf spring tab is being pushed out of the jawbone base engagement hole, optionally with a small amount of contact between the two during a slipping action, providing a tight tolerance such that the tab slightly resists rotation of the jawbone base. As the tab slips out of the engagement hole, this minor amount of interference may be further reduced. Due to the ramping or wedging action between the lower arm tooth and jawbone base tooth 1616a(1), the lower frame element is pushed or bowed downwardly in a flexing motion. The contact point between backside tooth 1616a(3) and vertical arm tooth 1741 also begin to escape engagement.

With continuing reference to the push motion of the actuation procedure, FIG. 16N shows that as the operator maintains an engagement force on the frame button engagement pad, button 1700 remains moving in a direction indicated by arrow A. At this step in the actuation process, upper horizontal frame tooth 1721 operates as the primary driver to rotate jawbone 1614, by pressing against jawbone base tooth 1616a(5) in the direction indicated by arrow B. Engagement point 1622a' of tab 1622a and corresponding engagement point 1616b' of jawbone base aperture 1616b have now slipped past each other, as the button vertical arm 1740 continues to push against leaf spring 1622 in the direction indicated by arrow C and as the upper arm tooth 1721 pushes against jawbone base tooth 1616a(5) to rotate jawbone base 1616 about axis 1614" in the direction indicated by arrow D. Leaf spring tab is now lifted clear of the engagement hole. Similarly, tooth 1741 of vertical frame arm 1740 is now clear of jawbone base tooth 1616a(3) as frame button moves toward the right and tooth 1616a(3) rotates in the clockwise direction. As ramp surface 1733 of lower arm tooth 1731 and jawbone base tooth 1616a(1) slide along each other, with tooth 1616a(1) moving in the direction indicated by arrow E and tooth 1731 moving in the opposing direction indicated by arrow F, maximal interference has been reached and lower horizontal frame arm 1730 is fully flexed or curved downwardly in the direction indicated by arrow G. Rotation of jawbone base 1616 continues to lead to a corresponding rotation of jawbone 1614 as indicated by arrow H. The central axis of rotation is aligned with the jawbone axis. Hence, as depicted in FIG. 16N, the upper frame tooth 1721 is deeply engaged with jawbone base tooth 1616a(5), actively driving rotation of the jawbone base. The leaf spring tab has completely escaped engagement with the jawbone base engagement aperture, and the vertical arm tooth has escaped engagement or lost contact with jawbone base tooth 1616a(3). With leaf spring tab removed, free rotation of the jawbone base is allowed.

With further reference to the push motion of the actuation procedure, FIG. 16O shows that as the operator continues to maintain an engagement force on the frame button engagement pad, button 1700 remains moving in a direction indicated by arrow A. At this step in the actuation process, upper horizontal frame tooth 1721 continued to operate as the primary driver to rotate jawbone 1614, by pressing against jawbone base tooth 1616a(5) in the direction indicated by arrow B. Engagement tab 1622a is now distanced from of the jawbone base aperture, as the button vertical arm 1740 continues to push against leaf spring 1622 in the direction indicated by arrow C and as the upper arm tooth 1721 pushes against jawbone base tooth 1616a(5) to rotate jawbone base 1616 about axis 1614" in the direction indicated by arrow D. Leaf spring tab 1622a is now lifted well clear of the engagement hole, and as the operator continues to press against frame button 1700, leaf spring 1622 continues to load up with potential energy. Lower arm tooth 1731 and jawbone base tooth 1616*a*(1) have slid sufficiently along each other, with tooth 1616*a*(1) moving in the direction indicated by arrow E and tooth 1731 moving in the opposing direction indicated by arrow F, such that frame tooth 1731 has now dropped back behind jawbone base tooth 1616*a*(1) as lower horizontal frame arm 1730 returns to an unflexed or straightened configuration as indicated by arrow G. Thus, tooth 1616*a*(1) has escaped ramped engagement, and tooth 1731 is disposed between tooth 1616*a*(1) and 1616*a*(2). Rotation of jawbone base 1616 continues to cause a corresponding rotation of jawbone 1614 as indicated by arrow H. The central axis of rotation is aligned with the jawbone axis. As depicted in FIG. 16O, the upper frame tooth 1721 is deeply engaged with jawbone base tooth 1616*a*(5), actively driving rotation of the jawbone base. Due to a flat engagement surface or interface between tooth 1721 and tooth 1616*a*(5), which is substantially perpendicular to the upper horizontal frame member, there is little or no moment arm which would lead to flexing or bowing of the upper horizontal frame member as a result of engagement between tooth 1721 and tooth 1616*a*(5). However, as explained with reference to FIG. 16M, as a curvature develops in one horizontal arm, the opposing parallel horizontal arm may also develop a curvature due to the tension in the vertical members. Hence, as depicted in FIG. 16Q, a bowing in upper horizontal arm 1720 may lead to a bowing in lower horizontal arm 1730, due to tension generated in vertical arms 1710 and 1740.

With yet further reference to the push motion of the actuation procedure, FIG. 16P shows that as the operator continues to maintain an engagement force on the frame button engagement pad, button 1700 remains moving in a direction indicated by arrow A, until frame button can move no further. As shown here, the backside of engagement pad is contacting the outer cylindrical surface of jawbone base 1616. Hence, the end of the first stroke or actuation is reached, and the jawbone has rotated 45 degrees in the direction indicated by arrow H. At this step in the actuation process, upper horizontal frame tooth 1721 jawbone base tooth 1616*a*(5) in the direction indicated by arrow B substantially as far as possible. Engagement tab 1622*a* remains distanced from of the jawbone base aperture, as the button vertical arm 1740 has pushed leaf spring 1622 to a maximal extent in the direction indicated by arrow C thus fully loading leaf spring 1622 with potential energy. Lower arm tooth 1731 and jawbone base tooth 1616*a*(2) have slid sufficiently along each other, with tooth 1616*a*(2) moving in the direction indicated by arrow E and tooth 1731 moving in the opposing direction indicated by arrow F, such that lower horizontal frame has flexed again during ramped engagement (not shown) between tooth 1731 and tooth 1616*a*(2), and subsequently frame tooth 1731 has now dropped back behind jawbone base tooth 1616*a*(2) as lower horizontal frame arm 1730 returns to an unflexed or straightened configuration as indicated by arrow G.

Hence, as discussed above, FIGS. 16L-16P illustrate the push phase of a push-and-release actuation. As discussed below, FIGS. 16Q-16S illustrate the release phase of the push-and-release actuation.

As shown in FIG. 16Q, as the operator releases the engagement force on the frame button engagement pad, button 1700 begins to move in a direction indicated by arrow A. Leaf spring 1622, now loaded with potential energy, provides force in the direction indicated by arrow A' to press against button vertical frame member 1740. At this step in the actuation process, lower horizontal frame tooth 1731 operates as the primary driver to rotate jawbone 1614, by pressing against jawbone base tooth 1616*a*(2) in the direction indicated by arrow B. Relatedly, ramp surface 1723 of upper arm tooth 1721 and jawbone base tooth 1616*a*(6) slide along each other, with tooth 1616*a*(6) moving in the direction indicated by arrow E and tooth 1721 moving in the opposing direction indicated by arrow F. Accordingly, a central portion of upper horizontal frame arm 1720 flexes or bows upwardly in the direction indicated by arrow G. Upper frame arm 1720 curves in this manner due to the upper frame tooth ramping away from the jawbone base tooth moving in the opposite direction. Rotation of jawbone base 1616 leads to a corresponding rotation of jawbone 1614 as indicated by arrow H.

As explained with reference to FIG. 16M, as a curvature develops in one horizontal arm, the opposing parallel horizontal arm may also develop a curvature due to the tension in the vertical members. Hence, as depicted in FIG. 16Q, a bowing in upper horizontal arm 1720 may lead to a bowing in lower horizontal arm 1730, due to tension generated in vertical arms 1710 and 1740. For example, as upper horizontal frame arm 1720 flexes or bows upwardly in the direction indicated by arrow G, button vertical arm 1710 and frame button vertical arm 1740 are tensioned or pulled in an upward direction as indicated by arrows T1 and T2, respectively. This tension serves to create a bow or flex (not shown) in lower horizontal member 1730, and hence lower frame member tooth 1731 then engages more firmly or with more force the jawbone base tooth (e.g 1616*a*(2)) located opposite to the jawbone base tooth (e.g. 1616*a*(6)) which is slidingly engaging ramp surface 1723.

As shown in FIG. 16R, as leaf spring 1622 continues to maintain an engagement force on frame button vertical member as indicated by arrow A', button 1700 continues to move in a direction indicated by arrow A. Lower horizontal frame tooth 1731 remains the primary driver to rotate jawbone 1614, by pressing against jawbone base tooth 1616*a*(2) in the direction indicated by arrow B. As described previously, jawbone base 1616 includes two intersecting cylinders or bores 1616*b*, 1616*c* which provide engagement holes that receive a leaf spring tab 1622*a*. The cross-section view of the proximal portion of the base assembly shows the intersection between these two interior cylindrical surfaces or bores. When frame button shifts in the direction indicated by arrow A, an engagement point 1622*a*" of tab 1622*a* slips along a corresponding engagement point 1616*c*" of jawbone base aperture 1616*c*, as leaf spring 1622 pushes against the button vertical arm 1740 in the direction indicated by arrow A' and as the lower arm tooth 1731 pushes against jawbone base tooth 1616*a*(2) to rotate jawbone base 1616 about axis 1614" in the direction indicated by arrow D. Relatedly, ramp surface 1723 of upper arm tooth 1721 and jawbone base tooth 1616*a*(7) slide along each other, with tooth 1616*a*(7) moving in the direction indicated by arrow E and tooth 1721 moving in the opposing direction indicated by arrow F. Accordingly, a central portion of upper horizontal frame arm 1720 flexes or bows upwardly in the direction indicated by arrow G. Upper frame arm 1720 curves in this manner due to the upper frame tooth ramping away from the jawbone base tooth moving in the opposite direction. As explained with reference to FIG. 16Q, bowing in upper horizontal arm 1720 may lead to a bowing in lower horizontal arm 1730, due to tension generated in vertical arms 1710 and 1740, thus providing enhanced engagement between lower horizontal arm tooth 1731 and jawbone base tooth 1616*a*(2). Rotation of jawbone base 1616 leads to a corresponding rotation of jawbone 1614 as indicated by arrow H. Spring tooth 1622a begins to enter jawbone base engagement hole 1616c.

With further reference to the release motion of the actuation procedure, FIG. 16S shows that as the operator continues allowing leaf spring 1622 to maintain an engagement force on the frame button vertical member 1740 as indicated by arrow A', button 1700 remains moving in a direction indicated by arrow A. Tooth 1731 of lower horizontal frame member 1730 has driven jawbone base tooth 1616a(2) to the end of the stroke position. Hence, the pawl frame can fully return to the starting position, driven by the leaf spring. At this step in the actuation process, upper horizontal frame tooth 1721 is now positioned adjacent jawbone base tooth 1616a(7), and poised to engage tooth 1616a(7) during the next actuation of the frame button 1700. Engagement tab 1622a is positioned within engagement aperture 1616c of jawbone base 1616, and vertical frame member tooth 1741 is positioned between jawbone base teeth 1616a(5) and 1616a(4). Hence, spring tooth 1741 is situated for fully engaging the jawbone base teeth to take rotational loads. As shown here, jawbone 1614 has been rotated in the direction indicated by arrow H to a ninety degree angle relative to the position shown in FIG. 16L, and the button frame is now in the original position shown in FIG. 16L. By cycling through another push-and-release actuation, it is possible to rotate the jawbone an additional ninety degrees.

In some cases, a three (or multiple) segment electrode, double-(multiple) hinged pair of jaws can have hinges allowing sideways movement in each jaw. Such configurations allow the implementation of a left or right curve of variable radii or an S-curve, which may or may not be smooth curves, optionally including straight segments. In some cases, the entire shaft and jaw can be detached just distal to the handle, for example instead of midway on the body or more one body inside the other, with a connector for the electronics. There can be different jaw sets for right and left curves, and the like.

A mono/bi-polar convertible device can include coupling for electrical and water lines, or an electrical connector and mechanical guide features to connect the two body parts. Systems may also include external folding or hinging features to lock them into place. A convertible bi/monopolar couple mechanism can include a hinge mechanism to temporarily straighten a jaw at a crux to allow insertion of a monopolar assembly into a jaw. A convertible bi/monopolar couple mechanism can also include an enclosed jaw channel, such as a tunnel in the jaw for an electrode to pass within, with features to increase surface contact between an electrode and a tunnel roof or tissue contacting energy transmission member. Such configurations can guide a malleable monopolar electrode while recoupling the devices back into a bipolar position where an active or monopolar electrode is positioned parallel with the opposed indifferent electrode. In some cases, systems can include discrete bands or snap-in "over-center" electrode constraint features, or a continuous mesh over top or tunnel roof that is fixed or retractable and that contains an ablation member or electrode. Embodiments may also include a hinge at the shaft and jaw interface for coaxial orientation and port access introduction. Further, embodiments may include an introducer attachment to a jawbone having articulation and/or steerability, using magnets, with an integrated light/camera. Embodiments also encompass closed loop lasso introduction systems and methods.

According to some embodiments, the treatment systems and methods described herein may be used in conjunction or combined with aspects of introducer systems and methods such as those described in U.S. patent application No. 60/337,070 filed Dec. 4, 2001; Ser. No. 10/272,446 filed Oct. 15, 2002; Ser. No. 10/310,675 filed Dec. 4, 2002; Ser. No. 10/410,618 filed Apr. 8, 2003; Ser. No. 11/148,611 filed Jun. 8, 2005; 60/939,201 filed May 21, 2007; 61/015,472 filed Dec. 20, 2007; 61/051,975, filed May 9, 2008; Ser. No. 12/124,743 filed May 21, 2008; Ser. No. 12/124,766 filed May 21, 2008; Ser. No. 12/255,076 filed Oct. 21, 2008; Ser. No. 12/273,938 filed Nov. 19, 2008; Ser. No. 12/339,331 filed Dec. 19, 2008; Ser. No. 12/463,760 filed May 11, 2009; 61/179,564 filed May 19, 2009; 61/231,613 filed Aug. 5, 2009; and 61/241,297 filed Sep. 10, 2009. The entire content of each of these filings is incorporated herein by reference for all purposes.

Relatedly, in some instances, the treatment systems and methods described herein may include elements or aspects of the medical systems and methods discussed in U.S. Patent Application No. 60/337,070 filed Dec. 4, 2001; Ser. No. 10/080,374 filed Feb. 19, 2002; Ser. No. 10/255,025 filed Sep. 24, 2002; Ser. No. 10/272,446 filed Oct. 15, 2002; Ser. No. 10/310,675 filed Dec. 4, 2002; Ser. No. 10/410,618 filed Apr. 8, 2003; Ser. No. 11/067,535 filed Feb. 25, 2005; Ser. No. 11/148,611 filed Jun. 8, 2005; 60/939,201 filed May 21, 2007; 61/015,472 filed Dec. 20, 2007; 61/051,975, filed May 9, 2008; Ser. No. 12/124,743 filed May 21, 2008; Ser. No. 12/124,766 filed May 21, 2008; Ser. No. 12/255,076 filed Oct. 21, 2008; Ser. No. 12/273,938 filed Nov. 19, 2008; Ser. No. 12/339,331 filed Dec. 19, 2008; Ser. No. 12/463,760 filed May 11, 2009; 61/179,564 filed May 19, 2009; 61/231,613 filed Aug. 5, 2009; and 61/241,297 filed Sep. 10, 2009. The entire content of each of these filings is incorporated herein by reference for all purposes.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A treatment system for forming a lesion on a tissue of a patient, comprising:
    an actuator handle assembly; and
    a slidable clamp assembly coupled with the actuator handle assembly, wherein the slidable clamp assembly is configured to be translatable along a first axis, the slidable clamp assembly having a first jaw mechanism and a second jaw mechanism,
    wherein the first jaw mechanism comprises a first rotatable guide, and a first flexible ablation member in operative association with the first rotatable guide,
    wherein the second jaw mechanism comprises a second rotatable guide, and a second flexible ablation member in operative association with the second rotatable guide,
    wherein the first jaw mechanism is configured to adjustably revolve within a first collar, wherein the second jaw mechanism is configured to adjustably revolve within a second collar, and
    wherein the first jaw mechanism and the second jaw mechanism are both rotatable about a second axis, wherein the second axis is substantially perpendicular to the first axis.

2. The treatment system of claim 1, wherein the first jaw mechanism and the second jaw mechanism can be independently rotatably adjusted.

3. The treatment system of claim 1, further comprising a first push and release rotational assembly coupling the actuator handle assembly with the first jaw mechanism; and a second push and release rotational assembly coupling the actuator handle assembly with the second jaw mechanism.

4. The treatment system of claim 3, wherein the first push and release rotational assembly comprises a first frame button and a first leaf spring.

5. The treatment system of claim 4, wherein the first frame button comprises an engagement button, an upper horizontal arm having an upper tooth, a lower horizontal arm having a lower tooth, and a vertical arm having a vertical tooth.

6. The treatment system of claim 5, wherein the first leaf spring comprises an engagement tab, and the first push and release rotational assembly further comprises a jawbone base having an engagement aperture that receives the engagement tab.

7. The treatment system of claim 5, wherein the first push and release rotational assembly further comprises a jawbone base having a jawbone base tooth that engages at least one of the upper tooth, the lower tooth, or the vertical tooth of the first frame button.

8. The treatment system of claim 1, further comprising a first ablation member and a second ablation member coupled to the slidable clamp assembly;
    wherein the first ablation member is supported by the first jaw mechanism and has one or more electrodes, and
    wherein the second ablation member is supported by the second jaw mechanism and has one or more electrodes.

9. The treatment system of claim 8, wherein the first ablation member includes an active electrode, and the second ablation member includes a ground electrode.

10. The treatment system of claim 8, wherein the first ablation member includes a proximal electrode and a distal electrode coupled by a support assembly.

11. The treatment system of claim 8, wherein the second ablation member includes a proximal electrode and a distal electrode coupled by a support assembly.

\* \* \* \* \*